US012391669B2

(12) United States Patent
Backes et al.

(10) Patent No.: US 12,391,669 B2
(45) Date of Patent: Aug. 19, 2025

(54) SUBSTITUTED PYRIMIDINES AS IRE1 KINASE INHIBITORS

(71) Applicants: THE REGENTS OF THE UNIVERSITY OF CALIFORNIA, Oakland, CA (US); UNIVERSITY OF WASHINGTON THROUGH ITS CENTER FOR COMMERCIALIZATION, Seattle, WA (US)

(72) Inventors: Bradley Backes, San Francisco, CA (US); Feroz R. Papa, San Francisco, CA (US); Scott Andre Oakes, San Francisco, CA (US); Dustin J. Maly, Seattle, WA (US)

(73) Assignee: The Regents of the University of California et al., Oakland, CA (US)

( * ) Notice: Subject to any disclaimer, the term of this patent is extended or adjusted under 35 U.S.C. 154(b) by 1088 days.

(21) Appl. No.: 17/271,363

(22) PCT Filed: Aug. 30, 2019

(86) PCT No.: PCT/US2019/049238
§ 371 (c)(1),
(2) Date: Feb. 25, 2021

(87) PCT Pub. No.: WO2020/047518
PCT Pub. Date: Mar. 5, 2020

(65) Prior Publication Data
US 2021/0198238 A1    Jul. 1, 2021

Related U.S. Application Data

(60) Provisional application No. 62/725,177, filed on Aug. 30, 2018.

(51) Int. Cl.
| | | |
|---|---|---|
| *A61K 31/506* | (2006.01) | |
| *C07D 239/12* | (2006.01) | |
| *C07D 401/14* | (2006.01) | |
| *C07D 417/14* | (2006.01) | |

(52) U.S. Cl.
CPC ......... *C07D 401/14* (2013.01); *C07D 417/14* (2013.01)

(58) Field of Classification Search
CPC ........................... A61K 31/506; C07D 239/12
USPC ........................................... 514/275; 544/297
See application file for complete search history.

(56) References Cited

U.S. PATENT DOCUMENTS

| | | |
|---|---|---|
| 6,046,208 A | 4/2000 | Adams et al. |
| 2006/0009453 A1 | 1/2006 | Geuns-Meyer et al. |
| 2007/0213325 A1* | 9/2007 | Cee et al. ............... A61K 3/54 |
| | | 514/227.5 |

FOREIGN PATENT DOCUMENTS

| | | | | |
|---|---|---|---|---|
| CA | 2974788 A1 * | 8/2016 | .......... | C07D 401/14 |
| WO | WO-2005/113494 A2 | 12/2005 | | |
| WO | WO-2005/113494 A3 | 12/2005 | | |
| WO | WO-2018/166528 A1 | 9/2018 | | |
| WO | WO-2020047518 A1 * | 3/2020 | .............. | A61P 25/28 |

OTHER PUBLICATIONS

PubChemCID 57507169 , US National Library of Medicine, Aug. 8, 2012, p. 1-15; p. 2, https://pubchem.ncbi.nim.nih.gov/compound/57507169) (Year: 2012).*
Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag Gmbh & Co. KGaA, 2005, Preface.*
Harrington, P.E. et al. (Sep. 24, 2014). "Unfolded Protein Response in Cancer: IRE1α Inhibition by Selective Kinase Ligands Does Not Impair Tumor Cell Viability," *ACS Medicinal Chemistry Letters* 6(1):68-72.
International Search Report mailed on Nov. 26, 2019, for PCT Application No. PCT/US2019/049238, filed Aug. 30, 2019, 2 pages.
Partial Supplementary European Search Report mailed on Jun. 3, 2022, for EP Application No. 19854296.1, 11 pages.
PubChem CID 57507169, "4-(4-Methoxy-2-Methyl-1,3-Thiazol-5-yl)-N-Phenylpyrimidin-2-Amine," Aug. 8, 2012, 15 pages.
Ramirez-Montagut, et al. (May 19, 2003). Immunity to melanoma: unraveling the relation of tumor immunity and autoimmunity, *Oncogene* 22(20):3180-3187.
Sawaya, G.F. et al. (Oct. 16, 2003). "Risk of cervical cancer associated with extending the interval between cervical-cancer screenings," *New Engl. J. Med.* 349(16):1501-1509.
Written Opinion mailed on Nov. 26, 2019, for PCT Application No. PCT/US2019/049238, filed Aug. 30, 2019, 3 pages.

* cited by examiner

*Primary Examiner* — Douglas M Willis
(74) *Attorney, Agent, or Firm* — Mintz, Levin, Cohn, Ferris, Glovsky and Popeo, P.C.

(57) ABSTRACT

Disclosed herein are, inter alia, compounds modulating Inositol-Requiring Enzyme 1α (IRE1α) and IRE1β activity and methods of use thereof for treating IRE1α-mediated and IRE1β-mediated disorders.

18 Claims, No Drawings

SUBSTITUTED PYRIMIDINES AS IRE1 KINASE INHIBITORS

CROSS-REFERENCES TO RELATED APPLICATIONS

This application is the national stage filing under USC 371 of international application PCT/US2019/049238, filed Aug. 30, 2019, which claims the benefit of U.S. provisional application No. 62/725,177, filed Aug. 30, 2018, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. P01 HL108794 and R01 DK100623 awarded by the National Institutes of Health. The government has certain rights in the invention.

BACKGROUND

The IRE1α/β kinase/endoribonuclease is a critical regulator of the unfolded protein response (UPR) that promotes adaptation or apoptosis depending on the level of upstream 00000—
+endoplasmic reticulum stress (ERS). IRE1α/β kinase inhibitors can allosterically inhibit IRE1α/β's RNase activity to prevent over-activation and its subsequent apoptotic outputs that result.

IRE1α/β dysregulation/hyperactivity has been implicated in a range of disease states including, but not limited to, diabetes, cancer, fibrosis, and retinitis pigmentosa. In fibrotic disorders, for example, chronic endoplasmic reticulum stress leads to deposition of extracellular matrix components including collagen type I. Using IRE1α kinase inhibitors in two distinct murine models resulted in reduction of pro-fibrotic signaling associated with the UPR in lung epithelium. In these models, collagen levels were decreased and the pulmonary fibrosis reversed. This antifibrotic activity is important for treating fibrotic diseases of liver, kidney, and cardiac fibroses as well as scleroderma and psoriasis.

There is currently no cure for fibrotic diseases. Specifically, idiopathic pulmonary fibrosis (IPF) is lethal in 50% of patients within three years of diagnosis.

The drugs approved for IPF are OFEV® (nentedanib) and Esbriet® (pirfenidone). OFEV® was originally developed as a kinase inhibitor to treat cancer, and is known to hit a number of kinases. Esbriet® was developed as an anti-inflammatory drug. Both drugs have poor efficacy with significant rates of discontinuation.

Therefore, there is an unmet need for compounds capable of reversing the detrimental effects of unremediated ER stress. The proposed compounds have the potential to deliver potent, selective and drug-like oral inhibitors.

BRIEF SUMMARY

Provided herein, inter alia, are small molecule inositol-requiring enzyme 1α (Ire1α) kinase inhibitors that allosterically inhibit catalytic RNase domain via serine/threonine kinase domain, pharmaceutical compositions comprising these compounds, and the use of these compounds for the treatment of kinase-induced diseases. Also provided herein, inter alia, are small molecule inositol-requiring enzyme 1β (Ire1β) kinase inhibitors that allosterically inhibit catalytic RNase domain via serine/threonine kinase domain, pharmaceutical compositions comprising these compounds, and the use of these compounds for the treatment of kinase-induced diseases.

In an aspect, provided is a compound of structural formulae (Ia) and (Ib):

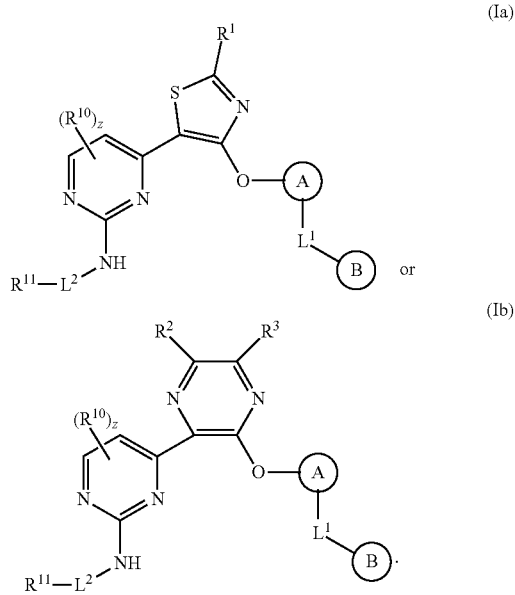

$L^1$ is independently a bond, —O—, —S—, —SO—, —S(O)$_2$—, —NR$^{12}$—, —C(O)—, —C(O)NR$^{12}$—, —C(O)O—, —S(O)$_2$NR$^{12}$—, —NR$^{12}$C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ is independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. Ring A is independently a substituted or unsubstituted aryl or substituted or unsubstituted heteroaryl. Ring B is independently a substituted or unsubstituted cycloalkyl, substituted or unsubstituted heterocycloalkyl, substituted or unsubstituted aryl or substituted or unsubstituted heteroaryl. $R^1$ is independently hydrogen, halogen, —CX$^1_3$, —CHX$^1_2$, —CH$_2$X$^1$, —OCX$^1_3$, —OCHX$^1_2$, —OCH$_2$X$^1$, —CN, —S(O)$_2$R$^{1A}$, —SR$^{1A}$, —S(O)R$^{1A}$, —SO$_2$NR$^{1A}$R$^{1B}$, —NHC(O)NR$^{1A}$R$^{1B}$, —N(O)$_2$, —NR$^{1A}$R$^{1B}$, —NHNR$^{1A}$R$^{1B}$, —C(O)R$^{1A}$, —C(O)—OR$^{1A}$, —C(O)NR$^{1A}$R$^{1B}$, —C(O)NHNR$^{1A}$R$^{1B}$, —OR$^{1A}$, —NR$^{1A}$SO$_2$R$^{1B}$, —NR$^{1A}$C(O)R$^{1B}$, —NR$^{1A}$C(O)OR$^{1B}$, —NR$^{1A}$OR$^{1B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, —CX$^2_3$, —CHX$^2_2$, —CH$_2$X$^2$, —OCX$^2_3$, —OCHX$^2_2$, —OCH$_2$X$^2$, —CN, —S(O)$_2$R$^{2A}$, —SR$^{2A}$, —S(O)R$^{2A}$, —SO$_2$NR$^{2A}$R$^{2B}$, —NHC(O)NR$^{2A}$R$^{2B}$, —N(O)$_2$, —NR$^{2A}$R$^{2B}$, —NHNR$^{2A}$R$^{2B}$, —C(O)R$^{2A}$, —C(O)—OR$^{2A}$, —C(O)NR$^{2A}$R$^{2B}$, —C(O)NHNR$^{2A}$R$^{2B}$, —OR$^{2A}$, —NR$^{2A}$SO$_2$R$^{2B}$, —NR$^{2A}$C(O)R$^{2B}$, —NR$^{2A}$C(O)OR$^{2B}$, —NR$^{2A}$OR$^{2B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is hydrogen, halogen, —CX$^3{}_3$, —CHX$^3{}_2$, —CH$_2$X$^3$, —OCX$^3{}_3$, —OCHX$^3{}_2$, —OCH$_2$X$^3$, —CN, —S(O)$_2$R$^{3A}$, —SR$^{3A}$, —S(O)R$^{3A}$, —SO$_2$NR$^{3A}$R$^{3B}$, —NHC(O)NR$^{3A}$R$^{3B}$, —N(O)$_2$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —C(O)NHNR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{10}$ is independently —CX$^{10}{}_3$, —CHX$^{10}{}_2$, —CH$_2$X$^{10}$, —OCX$^{10}{}_3$, —OCHX$^{10}{}_2$, —OCH$_2$X$^{10}$, —S(O)$_2$R$^{10A}$, —SR$^{10A}$, —S(O)R$^{10A}$, —SO$_2$NR$^{10A}$R$^{10B}$, —NHC(O)NR$^{10A}$R$^{10B}$, —NR$^{10A}$R$^{10B}$, —NHNR$^{10A}$R$^{10B}$, —C(O)R$^{10A}$, —C(O)—OR$^{10A}$, —C(O)NR$^{10A}$R$^{10B}$, —C(O)NHNR$^{10A}$R$^{10B}$, —OR$^{10A}$, —NR$^{10A}$SO$_2$R$^{10B}$, —NR$^{10A}$C(O)R$^{10B}$, —NR$^{10A}$C(O)OR$^{10B}$, —NR$^{10A}$OR$^{10B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{11}$ is independently —N(R$^{14}$)$_2$ or a substituted or unsubstituted nitrogen-containing heterocycloalkyl. R$^{12}$ is independently hydrogen, —CX$^{12}{}_3$, —CHX$^{12}{}_2$, —CH$_2$X$^{12}$, —OCX$^{12}{}_3$, —OCHX$^{12}{}_2$, —OCH$_2$X$^{12}$, —S(O)$_2$R$^{12A}$, —SR$^{12A}$, —S(O)R$^{12A}$, —SO$_2$NR$^{12A}$R$^{12B}$, —NHC(O)NR$^{12A}$R$^{12B}$, —NR$^{12A}$R$^{12B}$, —NHNR$^{12A}$R$^{12B}$, —C(O)R$^{12A}$, —C(O)—OR$^{12A}$, —C(O)NR$^{12A}$R$^{12B}$, —C(O)NHNR$^{12A}$R$^{12B}$, —OR$^{12A}$, —NR$^{12A}$SO$_2$R$^{12B}$, —NR$^{12A}$C(O)R$^{12B}$, —NR$^{12A}$C(O)OR$^{12B}$, —NR$^{12A}$OR$^{12B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{14}$ are independently hydrogen, —CX$^{14}{}_3$, —CHX$^{14}{}_2$, —CH$_2$X$^{14}$, —OCX$^{14}{}_3$, —OCHX$^{14}{}_2$, —OCH$_2$X$^{14}$, —S(O)$_2$R$^{14A}$, —SR$^{14A}$, —S(O)R$^{14A}$, —SO$_2$NR$^{14A}$R$^{14B}$, —NHC(O)NR$^{14A}$R$^{14B}$, —NR$^{14A}$R$^{14B}$, —NHNR$^{14A}$R$^{14B}$, —C(O)R$^{14A}$, —C(O)—OR$^{14A}$, —C(O)NR$^{14A}$R$^{14B}$, —C(O)NHNR$^{14A}$R$^{14B}$, —OR$^{14A}$, —NR$^{14A}$SO$_2$R$^{14B}$, —NR$^{14A}$C(O)R$^{14B}$, —NR$^{14A}$C(O)OR$^{14B}$, —NR$^{14A}$OR$^{14B}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{1A}$, R$^{1B}$, R$^{2A}$, R$^{2B}$, R$^{3A}$, R$^{3B}$, R$^{1A}$, R$^{10B}$, R$^{12A}$, R$^{12B}$, R$^{14A}$, and R$^{14B}$ are independently hydrogen, —CX$_3$, —CHX$_2$, —CH$_2$X, —C(O)OH, —C(O)NH$_2$, —OH, —NH$_2$, —COOH, —CONH$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{10A}$ and R$^{10B}$ substituents bonded to the same nitrogen atom may optionally be joined to form a substituted or unsubstituted heterocycloalkyl or substituted or unsubstituted heteroaryl; R$^{12A}$ and R$^{12B}$ substituents bonded to the same nitrogen atom may optionally be joined to form a substituted or unsubstituted heterocycloalkyl or substituted or unsubstituted heteroaryl; R$^{14A}$ and R$^{14B}$ substituents bonded to the same nitrogen atom may optionally be joined to form a substituted or unsubstituted heterocycloalkyl or substituted or unsubstituted heteroaryl. X, X$^1$, X$^2$, X$^3$, X$^{10}$, X$^{12}$ and X$^4$ are independently halogen. Symbol z is 0, 1 or 2.

In another aspect, provided is a pharmaceutical composition including a pharmaceutically acceptable excipient and a compound, as described herein.

In another aspect, provided is a method of treating a inositol-requiring enzyme 1α (Ire1α) modulated disease or disorder in a subject in need of the treatment, the method including administering an effective amount of a compound described herein, to the subject. In another aspect, provided is a method of treating a inositol-requiring enzyme 1β (Ire1β) modulated disease or disorder in a subject in need of the treatment, the method including administering an effective amount of a compound described herein, to the subject.

Further provided is a method of treating a general gastrointestinal tract inflammation in a subject in need of the treatment, the method including administering an effective amount of a compound described herein, to the subject.

Further provided is a method of treating a chronic inflammatory lung disease in a subject in need of the treatment, the method including administering an effective amount of a compound described herein, to the subject.

Further provided is a method of treating a neurodegenerative disease or disorder in a subject in need of the treatment, the method including administering an effective amount of a compound described herein, to the subject.

Further provided is a method of treating a posterior eye indication in a subject in need of the treatment, the method including administering an effective amount of a compound described herein, to the subject.

Further provided is a method of treating diabetes mellitus in a subject in need of the treatment, the method including administering an effective amount of a compound described herein, to the subject.

Further provided is a method of treating a fibrotic disorder in a subject in need of the treatment, the method including administering an effective amount of a compound described herein, to the subject.

Further provided is a method of treating a demyelinating disorder in a subject in need of the treatment, the method including administering an effective amount of a compound described herein, to the subject.

Further provided is a method of treating a peripheral neuropathy in a subject in need of the treatment, the method including administering an effective amount of a compound described herein, to the subject.

Further provided is a method of treating a dermatologic disorder in a subject in need of the treatment, the method including administering an effective amount of a compound described herein, to the subject.

Further provided is a method of treating a rheumatologic/autoimmune disorder in a subject in need of the treatment, the method including administering an effective amount of a compound described herein, to the subject.

DETAILED DESCRIPTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in additional to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—S—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2] nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⟶" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

The term "alkylarylene" as an arylene moiety covalently bonded to an alkylene moiety (also referred to herein as an alkylene linker). In embodiments, the alkylarylene group has the formula:

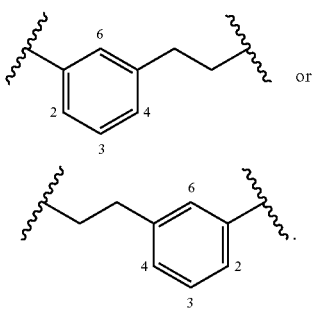

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C'''R''R''')$_d$—, where s and d are independently integers of from 0 to 3, and X is —O—, —NR'—, —S—, —S(O)—, —S(O)$_2$—, or —S(O)$_2$NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC (O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_5$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —$CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "disease" or "condition" refer to a state of being or health status of a patient or subject capable of being treated with the compounds or methods provided herein. The disease may be a cancer. The disease may be an autoimmune disease. The disease may be an inflammatory disease. The disease may be an infectious disease.

In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "general gastro-intestinal tract inflammation" refers to chronic inflammation of the gastrointestinal tract which primarily includes ulcerative colitis and Crohn's disease. Ulcerative colitis is characterized by inflammation occurring in the innermost lining of the large intestine (colon). Crohn's disease is characterized by inflammation occurring anywhere along the lining of the digestive tract.

As used herein, the term "chronic inflammatory lung disease" refers to chronic inflammation of lung tissue. Exemplary disorders include, but are not limited to, bronchial asthma, chronic obstructive pulmonary disease (COPD), and bronchiectasis or cystic fibrosis (CF).

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Stemberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifori carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "cutaneous metastasis" or "skin metastasis" refer to secondary malignant cell growths in the skin, wherein the malignant cells originate from a primary cancer site (e.g., breast). In cutaneous metastasis, cancerous cells from a primary cancer site may migrate to the skin where they divide and cause lesions. Cutaneous metastasis may result from the migration of cancer cells from breast cancer tumors to the skin.

The term "visceral metastasis" refer to secondary malignant cell growths in the internal organs (e.g., heart, lungs, liver, pancreas, intestines) or body cavities (e.g., pleura, peritoneum), wherein the malignant cells originate from a primary cancer site (e.g., head and neck, liver, breast). In visceral metastasis, cancerous cells from a primary cancer site may migrate to the internal organs where they divide and cause lesions. Visceral metastasis may result from the migration of cancer cells from liver cancer tumors or head and neck tumors to internal organs.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA). In certain instances, the autoimmune disease is rheumatoid arthritis, Grave's disease, Hashimoto disease, Addison's disease, lupus, ankylosing spondylitis, and sarcoidosis.

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis. In certain instances, the inflammatory disease is psoriasis.

As used herein, the term "diabetes mellitus" refers to a group of metabolic disorders characterized by high blood sugar levels over a prolonged period of time. In certain instances, diabetes mellitus is represented by type 1 diabetes, type 2 diabetes, monogenic (MODY) syndrome, and recessive genetic disorders (Wolcott Rallisson syndrome and Wolfram syndrome).

As used herein, the term "neurodegenerative disorder" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, chronic fatigue syndrome, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, myalgic encephalomyelitis, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes dorsalis. In certain instances, the neurodegenerative disorder is amyotrophic lateral sclerosis (ALS), Parkinson's disease, Alzheimer's disease, Prion diseases, and frontotemporal dementia.

As used herein, the term "peripheral neuropathy" refers to a damaged neuron, a condition caused by trauma, injury, local compression, prolonged pressure, or inflammation of a nerve or group of nerves. Peripheral neuropathy can be primary, such as Charcot-Marie Tooth (CMT), or secondary, caused by diabetes mellitus.

As used herein, the term "demyelinating disorder" refers to a disorder of the nervous system in which the myelin sheath of neurons is damaged. In certain instance, the demyelinating disorder is multiple sclerosis (MS), GUillan-Barre syndrome, adrenoleukodystrophy, adrenomyeloneuropathy, optic neuritis, and transverse myelitis.

As used herein, the term "fibrosing disorder" refers to a condition characterized by lesions of circumscribed fibrotic areas involving different levels of the dermis, subcutis, and, sometimes, underlying soft tissue abd bone. In certain instances, fibrosing disorder is idiopathic pulmonary fibrosis (IPF), familial pulmonary fibrosis (FPF), scleroderma (systemic sclerosis), renal fibrosis, and hepatic fibrosis.

As used herein, the terms "posterior eye indication" or "anterior eye indication" refer to eye conditions caused by changes in the anterior hyaloid membrane of the eye and the optical structures behind it. In certain instances, posterior eye indication is retinal degeneration represented by retinitis pigmentosa, Stargardt's disease, wet AMD, and dry AMD. In certain instances, anterior eye indication is glaucoma and Fuch's dystrophy.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of an Ire1α-mediated or Ire1β-mediated disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

"Selective" or "selectivity" or the like of a compound refers to the compound's ability to discriminate between molecular targets (e.g. a compound having selectivity toward HMT SUV39H1 and/or HMT G9a).

"Specific", "specifically", "specificity", or the like of a compound refers to the compound's ability to cause a particular action, such as inhibition, to a particular molecular target with minimal or no action to other proteins in the cell (e.g. a compound having specificity towards HMT SUV39H1 and/or HMT G9a displays inhibition of the activity of those HMTs whereas the same compound displays little-to-no inhibition of other HMTs such as DOT1, EZH1, EZH2, GLP, MLL1, MLL2, MLL3, MLL4, NSD2, SET1b, SET7/9, SET8, SETMAR, SMYD2, SUV39H2).

The "serine/threonine-protein kinase/endoribonuclease inositol-requiring enzyme 1 (Ire1)", as used herein, refers to an enzyme that in humans is encoded by the ERN1 gene. The protein encoded by this gene is the endoplasmic reticulum (ER) to nucleus signalling 1 protein, a human homologue of the yeast Ire1 gene product. This protein possesses intrinsic kinase activity and an endoribonuclease activity and it is important in altering gene expression as a response to endoplasmic reticulum-based stress signals (mainly the unfolded protein response). Two alternatively spliced transcript variants encoding different isoforms have been found for this gene. Ire1α possesses two functional enzymatic domains, an endonuclease and a trans-autophosphorylation kinase domain. Upon activation, Ire1α oligomerizes and carries out an unconventional RNA splicing activity, removing an intron from the X-box binding protein 1 (XBP1) mRNA, and allowing it to become translated into a functional transcription factor, XBP1s. XBP1s upregulates ER chaperones and endoplasmic reticulum associated degradation (ERAD) genes that facilitate recovery from endoplasmic reticulum (ER) stress. IRE1β is specifically expressed in intestinal epithelial cells, and is thought to be involved in translational repression on the ER membrane. This selective repression depends on the RNase activity of IRE1β.

"Unfolded protein response (UPR)", as used herein, refers to a cellular stress response related to the endoplasmic reticulum (ER) stress. It is a stress response that has been found to be conserved between all mammalian species, as well as yeast and worm organisms. The UPR is activated in response to an accumulation of unfolded or misfolded proteins in the lumen of the endoplasmic reticulum. The UPR performs three major functions in a cell: restoring normal function of the cell by halting protein translation, degrading misfolded proteins, and activating signalling pathways that lead to increasing production of molecular chaperones involved in protein folding. If these objectives are not achieved within a certain time span or the disruption is prolonged, the UPR aims towards apoptosis. Sustained overactivation of the UPR has been implicated in several neurodegenerative diseases, such as Creutzfeldt-Jakob disease, Alzheimer's disease, Parkinson's disease, and Huntington's disease.

"Endoplasmic reticulum (ER) stress", as used herein, refers to a situation within a cell when the protein synthesis requirements of the cell exceed the protein folding capacity of the ER. Improperly folded proteins accumulate in the ER, which triggers the unfolded protein response (UPR) to restore ER homeostasis.

II. Compounds

In an aspect, provided herein is a compound having the formula:

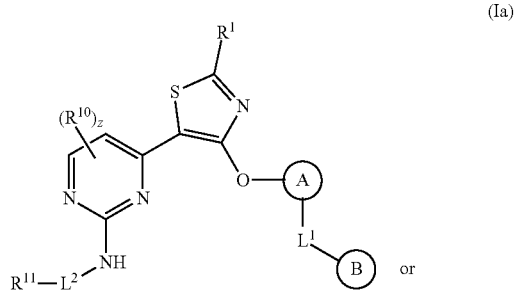

(Ia)

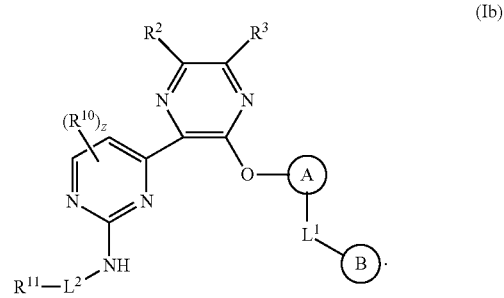

(Ib)

$L^1$ is independently a bond, —O—, —S—, —SO—, —S(O)$_2$—, —NR$^{12}$—, —C(O)—, —C(O)NR$^{12}$—, —C(O)O—, —S(O)$_2$NR$^{12}$—, —NR$^{12}$C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^2$ is independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. Ring A is independently a substituted or unsubstituted aryl or substituted or unsubstituted heteroaryl. Ring B is independently a substituted or unsubstituted cycloalkyl, substituted or unsubstituted heterocycloalkyl, substituted or unsubstituted aryl or substituted or unsubstituted heteroaryl.

$R^1$ is independently hydrogen, halogen, $-CX^1_3$, $-CHX^1_2$, $-CH_2X^1$, $-OCX^1_3$, $-OCHX^1_2$, $-OCH_2X^1$, $-CN$, $-S(O)_zR^{1A}$, $-SR^{1A}$, $-S(O)R^{1A}$, $-SO_2NR^{1A}R^{1B}$, $-NHC(O)NR^{1A}R^{1B}$, $-N(O)_2$, $-NR^{1A}R^{1B}$, $-NHNR^{1A}R^{1B}$, $-C(O)R^{1A}$, $-C(O)-OR^{1A}$, $-C(O)NR^{1A}R^{1B}$, $-C(O)NHNR^{1A}R^{1B}$, $-OR^{1A}$, $-NR^{1A}SO_2R^{1B}$, $-NR^{1A}C(O)R^{1B}$, $-NR^{1A}C(O)OR^{1B}$, $-NR^{1A}OR^{1B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently hydrogen, halogen, $-CX^2_3$, $-CHX^2_2$, $-CH_2X^2$, $-OCX^2_3$, $-OCHX^2_2$, $-OCH_2X^2$, $-CN$, $-S(O)_zR^{2A}$, $-SR^{2A}$, $-S(O)R^{2A}$, $-SO_2NR^{2A}R^{2B}$, $-NHC(O)NR^{2A}R^{2B}$, $-N(O)_2$, $-NR^{2A}R^{2B}$, $-NHNR^{2A}R^{2B}$, $-C(O)R^{2A}$, $-C(O)-OR^{2A}$, $-C(O)NR^{2A}R^{2B}$, $-C(O)NHNR^{2A}R^{2B}$, $-OR^{2A}$, $-NR^{2A}SO_2R^{2B}$, $-NR^{2A}C(O)R^{2B}$, $-NR^{2A}C(O)OR^{2B}$, $-NR^{2A}OR^{2B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently hydrogen, halogen, $-CX^3_3$, $-CHX^3_2$, $-CH_2X^3$, $-OCX^3_3$, $-OCHX^3_2$, $-OCH_2X^3$, $-CN$, $-S(O)_zR^{3A}$, $-SR^{3A}$, $-S(O)R^{3A}$, $-SO_2NR^{3A}R^{3B}$, $-NHC(O)NR^{3A}R^{3B}$, $-N(O)_2$, $-NR^{3A}R^{3B}$, $-NHNR^{3A}R^{3B}$, $-C(O)R^{3A}$, $-C(O)-OR^{3A}$, $-C(O)NR^{3A}R^{3B}$, $-C(O)NHNR^{3A}R^{3B}$, $-OR^{3A}$, $-NR^{3A}SO_2R^{3B}$, $-NR^{3A}C(O)R^{3B}$, $-NR^{3A}C(O)OR^{3B}$, $-NR^{3A}OR^{3B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10}$ is independently $-CX^{10}_3$, $-CHX^{10}_2$, $-CH_2X^{10}$, $-OCX^{10}_3$, $-OCHX^{10}_2$, $-OCH_2X^{10}$, $-S(O)_zR^{10A}$, $-SR^{10A}$, $-S(O)R^{10A}$, $-SO_2NR^{10A}R^{10B}$, $-NHC(O)NR^{10A}R^{10B}$, $-NR^{10A}R^{10B}$, $-NHNR^{10A}R^{10B}$, $-C(O)R^{10A}$, $-C(O)-OR^{10A}$, $-C(O)NR^{10A}R^{10B}$, $-C(O)NHNR^{10A}R^{10B}$, $-OR^{10A}$, $-NR^{10A}SO_2R^{10B}$, $-NR^{10A}C(O)R^{10B}$, $-NR^{10A}C(O)OR^{10B}$, $-NR^{10A}OR^{10B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Symbol z is 0, 1 or 2. $R^{11}$ is independently $-N(R^{14})_2$ or a substituted or unsubstituted nitrogen-containing heterocycloalkyl. $R^{12}$ is independently hydrogen, $-CX^{12}_3$, $-CHX^{12}_2$, $-CH_2X^{12}$, $OCX^{12}_3$, $-OCHX^{12}_2$, $-OCH_2X^{12}$, $-S(O)_zR^{12A}$, $-SR^{12A}$, $-S(O)R^{12A}$, $-SO_2NR^{12A}R^{12B}$, $-NHC(O)NR^{12A}R^{12B}$, $-NR^{12A}R^{12B}$, $-NHNR^{12A}R^{12B}$, $-C(O)R^{12A}$, $-C(O)-OR^{12A}$, $-C(O)NR^{12A}R^{12B}$, $-C(O)NHNR^{12A}R^{12B}$, $-OR^{12A}$, $-NR^{12A}SO_2R^{12B}$, $-NR^{12A}C(O)R^{12B}$, $-NR^{12A}C(O)OR^{12B}$, $-NR^{12A}OR^{12B}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{14}$ is independently hydrogen, $-CX^{14}_3$, $-CHX^{14}_2$, $-CH_2X^{14}$, $-OCX^{14}_3$, $-OCHX^{14}_2$, $-OCH_2X^{14}$, $-S(O)_zR^{14A}$, $-SR^{14A}$, $-S(O)R^{14A}$, $-SO_2NR^{14A}R^{14B}$, $-NHC(O)NR^{14A}R^{14B}$, $-NR^{14A}R^{14B}$, $-NHNR^{14A}R^{14B}$, $-C(O)R^{14A}$, $-C(O)-OR^{14A}$, $-C(O)NR^{14A}R^{14B}$, $-C(O)NHNR^{14A}R^{14B}$, $-OR^{14A}$, $-NR^{14A}SO_2R^{14B}$, $-NR^{14A}C(O)R^{14B}$, $-NR^{14A}C(O)OR^{14B}$, $-NR^{14A}OR^{14B}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, $R^{2A}$, $R^{2B}$, $R^{3A}$, $R^{3B}$, $R^{10A}$, $R^{10B}$, $R^{12A}$, $R^{12B}$, $R^{14A}$ and $R^{14B}$ are independently hydrogen, $-CX_3$, $-CHX_2$, $-CH_2X$, $-C(O)OH$, $-C(O)NH_2$, $-OH$, $-NH_2$, $-COOH$, $-CONH_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX_3$, $-OCHX_2$, $-OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{10A}$ and $R^{10B}$ substituents bonded to the same nitrogen atom may optionally be joined to form a substituted or unsubstituted heterocycloalkyl or substituted or unsubstituted heteroaryl; $R^{12A}$ and $R^{12B}$ substituents bonded to the same nitrogen atom may optionally be joined to form a substituted or unsubstituted heterocycloalkyl or substituted or unsubstituted heteroaryl; and $R^{14A}$ and $R^{14B}$ substituents bonded to the same nitrogen atom may optionally be joined to form a substituted or unsubstituted heterocycloalkyl or substituted or unsubstituted heteroaryl.

$X$, $X^1$, $X^2$, $X^3$, $X^{10}$, $X^1_2$, and $X^{14}$ are independently halogen.

z is 0, 1, or 2.

In embodiments, $L^1$ is independently a bond, $-O-$, $-S-$, $-SO-$, $-S(O)_2-$, $-NR^{12}-$, $-C(O)-$, $-C(O)NR^{12}-$, $-C(O)O-$, $-S(O)_2NR^{12}-$, $-NR^{12}C(O)O-$, substituted (e.g., substituted with a substituent group, a size-limited substituent group, or lower substituent group) or unsubstituted alkylene (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkylene (e.g., 2 to 8 membered, 2 to 6 membered, or 2 to 4 membered), substituted (e.g., substituted with a substituent group, a size-limited substituent group, or lower substituent group) or unsubstituted cycloalkylene (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkylene (e.g., 3 to 8 membered, 3 to 6 membered, or 5 to 6 membered), substituted (e.g., substituted with a substituent group, a size-limited substituent group, or lower substituent group) or unsubstituted arylene (e.g., $C_6$-$C_{10}$, $C_6$, or phenyl), or substituted (e.g., substituted with a substituent group, a size-limited substituent group, or lower substituent group) or unsubstituted heteroarylene (e.g., 5 to 10 membered, 5 to 9 membered, or 5 to 6 membered).

In embodiments, $L^1$ is -$L^{1A}$-$L^{1B}$-$L^{1C}$-, wherein $L^{1A}$ and $L^{1C}$ are independently a bond or a substituted (e.g., substituted with a substituent group, a size-limited substituent group, or lower substituent group) or unsubstituted alkylene (e.g., $C_1$-$C_8$, $C_1$-$C_6$, or $C_1$-$C_4$). In embodiments, $L^{1A}$ and $L^{1C}$ are a bond. In embodiments, $L^{1A}$ and $L^{1C}$ are independently a substituted (e.g., substituted with a substituent group, a size-limited substituent group, or lower substituent group) or unsubstituted alkylene (e.g., $C_1$-$C_8$, $C_1$-$C_6$, or $C_1$-$C_4$). In embodiments, $L^{1A}$ and $L^{1C}$ are independently a substituted (e.g., substituted with a substituent group, a size-limited substituent group, or lower substituent group) or unsubstituted methylene or substituted (e.g., substituted with a substituent group, a size-limited substituent group, or lower substituent group) or unsubstituted ethylene. In embodiments, $L^{1B}$ is —O—, —S—, —SO—, —S(O)$_2$—, —NR$^{12}$—, —C(O)—, —C(O)NR$^{12}$—, —C(O)O—, —S(O)$_2$NR$^{12}$—, or —NR$^{12}$C(O)O—. In embodiments, -L$^{1A}$-L$^{1B}$-L$^{1C}$- is —C(O)N(CH$_3$)CH$_2$—, —C(O)NHCH$_2$—, —C(O)NH—, —NHSO$_2$—, —NHSO$_2$CH$_2$—, or —CH$_2$NHSO$_2$—.

In embodiments, $L^2$ is independently a bond, substituted (e.g., substituted with a substituent group, a size-limited substituent group, or lower substituent group) or unsubstituted alkylene (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkylene (e.g., 2 to 8 membered, 2 to 6 membered, or 2 to 4 membered), substituted (e.g., substituted with a substituent group, a size-limited substituent group, or lower substituent group) or unsubstituted cycloalkylene (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkylene (e.g., 3 to 8 membered, 3 to 6 membered, or 5 to 6 membered), substituted (e.g., substituted with a substituent group, a size-limited substituent group, or lower substituent group) or unsubstituted arylene (e.g., $C_6$-$C_{10}$, $C_6$, or phenyl), or substituted (e.g., substituted with a substituent group, a size-limited substituent group, or lower substituent group) or unsubstituted heteroarylene (e.g., 5 to 10 membered, 5 to 9 membered, or 5 to 6 membered).

In embodiments, ring A is a substituted or unsubstituted aryl (e.g., $C_6$-$C_{10}$ aryl, $C_{10}$ aryl, or phenyl) or substituted or unsubstituted heteroaryl (e.g., 5 to 10 membered heteroaryl, 5 to 9 membered heteroaryl, or 5 to 6 membered heteroaryl). In embodiments, ring A is $R^8$-substituted or unsubstituted aryl (e.g., $C_6$-$C_{10}$ aryl, $C_{10}$ aryl, or phenyl) or $R^8$-substituted or unsubstituted heteroaryl (e.g., 5 to 10 membered heteroaryl, 5 to 9 membered heteroaryl, or 5 to 6 membered heteroaryl).

In embodiments, ring A is $R^8$-substituted or unsubstituted aryl (e.g., $C_6$-$C_{10}$ aryl, $C_{10}$ aryl, or phenyl). In embodiments, ring A is $R^8$-substituted or unsubstituted phenyl or $R^8$-substituted or unsubstituted naphthyl.

In embodiments, ring A is $R^8$-substituted or unsubstituted heteroaryl (e.g., 5 to 10 membered heteroaryl, 5 to 9 membered heteroaryl, or 5 to 6 membered heteroaryl). In embodiments, ring A is $R^8$-substituted or unsubstituted pyrrolyl. In embodiments, ring A is $R^8$-substituted or unsubstituted pyrazolyl. In embodiments, ring A is $R^8$-substituted or unsubstituted pyridazinyl. In embodiments, ring A is $R^8$-substituted or unsubstituted triazinyl. In embodiments, ring A is $R^8$-substituted or unsubstituted pyrimidinyl. In embodiments, ring A is $R^8$-substituted or unsubstituted imidazolyl. In embodiments, ring A is $R^8$-substituted or unsubstituted pyrazinyl. In embodiments, ring A is $R^8$-substituted or unsubstituted purinyl. In embodiments, ring A is $R^8$-substituted or unsubstituted purinyl. In embodiments, ring A is $R^8$-substituted or unsubstituted oxazolyl. In embodiments, ring A is $R^8$-substituted or unsubstituted isoxazolyl. In embodiments, ring A is $R^8$-substituted or unsubstituted thiazolyl. In embodiments, ring A is $R^8$-substituted or unsubstituted furyl. In embodiments, ring A is $R^8$-substituted or unsubstituted thienyl. In embodiments, ring A is $R^8$-substituted or unsubstituted pyridyl. In embodiments, ring A is $R^8$-substituted or unsubstituted pyrimidyl.

In embodiments, ring A is $R^8$-substituted or unsubstituted benzothiazolyl. In embodiments, ring A is $R^8$-substituted or unsubstituted benzoxazoyl. In embodiments, ring A is $R^8$-substituted or unsubstituted benzimidazolyl. In embodiments, ring A is $R^8$-substituted or unsubstituted benzofuranyl. In embodiments, ring A is $R^8$-substituted or unsubstituted isobenzofuranyl. In embodiments, ring A is $R^8$-substituted or unsubstituted indolyl. In embodiments, ring A is $R^8$-substituted or unsubstituted isoindolyl. In embodiments, ring A is $R^8$-substituted or unsubstituted benzothiophenyl. In embodiments, ring A is $R^8$-substituted or unsubstituted isoquinolyl. In embodiments, ring A is $R^8$-substituted or unsubstituted quinoxalinyl. In embodiments, ring A is $R^8$-substituted or unsubstituted quinolyl. In embodiments, ring A is $R^8$-substituted or unsubstituted 1-naphthyl. In embodiments, ring A is $R^8$-substituted or unsubstituted 2-naphthyl. In embodiments, ring A is $R^8$-substituted or unsubstituted 4-biphenyl. In embodiments, ring A is $R^8$-substituted or unsubstituted 1-pyrrolyl. In embodiments, ring A is $R^8$-substituted or unsubstituted 2-pyrrolyl. In embodiments, ring A is $R^8$-substituted or unsubstituted 3-pyrrolyl. In embodiments, ring A is $R^8$-substituted or unsubstituted 3-pyrazolyl. In embodiments, ring A is $R^8$-substituted or unsubstituted 2-imidazolyl. In embodiments, ring A is $R^8$-substituted or unsubstituted 4-imidazolyl. In embodiments, ring A is $R^8$-substituted or unsubstituted pyrazinyl. In embodiments, ring A is $R^8$-substituted or unsubstituted 2-oxazolyl. In embodiments, ring A is $R^8$-substituted or unsubstituted 4-oxazolyl. In embodiments, ring A is $R^8$-substituted or unsubstituted 2-phenyl-4-oxazolyl. In embodiments, ring A is $R^8$-substituted or unsubstituted 5-oxazolyl. In embodiments, ring A is $R^8$-substituted or unsubstituted 3-isoxazolyl. In embodiments, ring A is $R^8$-substituted or unsubstituted 4-isoxazolyl. In embodiments, ring A is $R^8$-substituted or unsubstituted 5-isoxazolyl. In embodiments, ring A is $R^8$-substituted or unsubstituted 2-thiazolyl. In embodiments, ring A is $R^8$-substituted or unsubstituted 4-thiazolyl. In embodiments, ring A is $R^8$-substituted or unsubstituted 5-thiazolyl. In embodiments, ring A is $R^8$-substituted or unsubstituted 2-furyl. In embodiments, ring A is $R^8$-substituted or unsubstituted 3-furyl. In embodiments, ring A is $R^8$-substituted or unsubstituted 2-thienyl. In embodiments, ring A is $R^8$-substituted or unsubstituted 3-thienyl. In embodiments, ring A is $R^8$-substituted or unsubstituted 2-pyridyl. In embodiments, ring A is $R^8$-substituted or unsubstituted 3-pyridyl. In embodiments, ring A is $R^8$-substituted or unsubstituted 4-pyridyl. In embodiments, ring A is $R^8$-substituted or unsubstituted 2-pyrimidyl. In embodiments, ring A is $R^8$-substituted or unsubstituted 4-pyrimidyl. In embodiments, ring A is $R^8$-substituted or unsubstituted 5-benzothiazolyl. In embodiments, ring A is $R^8$-substituted or unsubstituted 5-benzothiazolyl. In embodiments, ring A is $R^8$-substituted or unsubstituted purinyl. In embodiments, ring A is $R^8$-substituted or unsubstituted 2-benzimidazolyl. In embodiments, ring A is $R^8$-substituted or unsubstituted 5-indolyl. In embodiments, ring A is $R^8$-substituted or unsubstituted 1-isoquinolyl. In embodiments, ring A is $R^8$-substituted or unsubstituted 5-isoquinolyl. In embodiments, ring A is $R^8$-substituted or unsubstituted 2-quinoxalinyl. In embodiments, ring A is $R^8$-substituted or unsubstituted 5-quinoxalinyl. In embodiments, ring A is $R^8$-substituted or unsubstituted 3-quinolyl. In embodiments, ring A is $R^8$-substituted or unsubstituted 6-quinolyl.

$R^8$ is independently hydrogen, halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{5A}$-substituted or unsubstituted alkyl (e.g., C$_1$-C$_8$ alkyl, C$_1$-C$_6$ alkyl, or C$_1$-C$_4$ alkyl), R$^{8A}$-substituted or unsubstituted heteroalkyl (e.g., 2 to 8 membered heteroalkyl, 2 to 6 membered heteroalkyl, or 2 to 4 membered heteroalkyl), R$^{8A}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{8A}$-substituted or unsubstituted heterocycloalkyl (e.g., 3 to 8 membered heterocycloalkyl, 3 to 6 membered heterocycloalkyl, or 5 to 6 membered heterocycloalkyl), R$^{8A}$-substituted or unsubstituted aryl (e.g., C$_6$-C$_{10}$ aryl, C$_{10}$ aryl, or phenyl), or R$^{8A}$-substituted or unsubstituted heteroaryl (e.g., 5 to 10 membered heteroaryl, 5 to 9 membered heteroaryl, or 5 to 6 membered heteroaryl).

In embodiments, R$^8$ is independently hydrogen, halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^8$ is R$^{8A}$-substituted or unsubstituted alkyl (e.g., C$_1$-C$_5$ alkyl, C$_1$-C$_6$ alkyl, or C$_1$-C$_4$ alkyl). In embodiments, R$^8$ is R$^{8A}$-substituted alkyl (e.g., C$_1$-C$_8$ alkyl, C$_1$-C$_6$ alkyl, or C$_1$-C$_4$ alkyl). In embodiments, R$^8$ is an unsubstituted alkyl (e.g., C$_1$-C$_5$ alkyl, C$_1$-C$_6$ alkyl, or C$_1$-C$_4$ alkyl). In embodiments, R$^8$ is R$^{8A}$-substituted or unsubstituted heteroalkyl (e.g., 2 to 8 membered heteroalkyl, 2 to 6 membered heteroalkyl, or 2 to 4 membered heteroalkyl). In embodiments, R$^8$ is R$^{8A}$-substituted heteroalkyl (e.g., 2 to 8 membered heteroalkyl, 2 to 6 membered heteroalkyl, or 2 to 4 membered heteroalkyl). In embodiments, R$^8$ is an unsubstituted heteroalkyl (e.g., 2 to 8 membered heteroalkyl, 2 to 6 membered heteroalkyl, or 2 to 4 membered heteroalkyl). In embodiments, R$^8$ is R$^{8A}$-substituted or unsubstituted cycloalkyl (e.g., C$_3$-C$_8$ cycloalkyl, C$_3$-C$_6$ cycloalkyl, or C$_5$-C$_6$ cycloalkyl 1). In embodiments, R$^8$ is R$^{8A}$-substituted cycloalkyl (e.g., C$_3$-C$_8$ cycloalkyl, C$_3$-C$_6$ cycloalkyl, or C$_5$-C$_6$ cycloalkyl). In embodiments, R$^8$ is an unsubstituted cycloalkyl (e.g., C$_3$-C$_8$ cycloalkyl, C$_3$-C$_6$ cycloalkyl, or C$_5$-C$_6$ cycloalkyl). In embodiments, R$^8$ is R$^{8A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^8$ is R$^{8A}$-substituted heterocycloalkyl (e.g., 3 to 8 membered heterocycloalkyl, 3 to 6 membered heterocycloalkyl, or 5 to 6 membered heterocycloalkyl). In embodiments, R$^8$ is an unsubstituted heterocycloalkyl (e.g., 3 to 8 membered heterocycloalkyl, 3 to 6 membered heterocycloalkyl, or 5 to 6 membered heterocycloalkyl). In embodiments, R$^8$ is R$^{8A}$-substituted or unsubstituted aryl (e.g., C$_6$-C$_{10}$ aryl, C$_{10}$ aryl, or phenyl). In embodiments, R$^8$ is R$^{8A}$-substituted aryl (e.g., C$_6$-C$_{10}$ aryl, C$_{10}$ aryl, or phenyl). In embodiments, R$^8$ is an unsubstituted aryl (e.g., C$_6$-C$_{10}$ aryl, C$_{10}$ aryl, or phenyl). In embodiments, R$^8$ is R$^{8A}$-substituted or unsubstituted heteroaryl (e.g., 5 to 10 membered heteroaryl, 5 to 9 membered heteroaryl, or 5 to 6 membered heteroaryl). In embodiments, R$^8$ is R$^{8A}$-substituted heteroaryl (e.g., 5 to 10 membered heteroaryl, 5 to 9 membered heteroaryl, or 5 to 6 membered heteroaryl). In embodiments, R$^8$ is an unsubstituted heteroaryl (e.g., 5 to 10 membered heteroaryl, 5 to 9 membered heteroaryl, or 5 to 6 membered heteroaryl).

In embodiments, R$^8$ is halogen. In embodiments, R$^8$ is —F. In embodiments, R$^8$ is unsubstituted C$_1$-C$_4$ alkyl. In embodiments, R$^8$ is methyl. In embodiments, R$^8$ is unsubstituted C$_6$-C$_{10}$ aryl. In embodiments, R$^8$ is phenyl.

R$^{8A}$ is independently —CX$^5_3$, —CHX$^5_2$, —CH$_2$X$^5$, —C(O)OH, —C(O)NH$_2$, —OH, —NH$_2$, —COOH, —CONH$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, R$^{8B}$-substituted or unsubstituted alkyl (e.g., C$_1$-C$_8$ alkyl, C$_1$-C$_6$ alkyl, or C$_1$-C$_4$ alkyl), R$^{8B}$-substituted or unsubstituted heteroalkyl (e.g., 2 to 8 membered heteroalkyl, 2 to 6 membered heteroalkyl, or 2 to 4 membered heteroalkyl), R$^{8B}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{8B}$-substituted or unsubstituted heterocycloalkyl (e.g., 3 to 8 membered heterocycloalkyl, 3 to 6 membered heterocycloalkyl, or 5 to 6 membered heterocycloalkyl), R$^{8B}$-substituted or unsubstituted aryl (e.g., C$_6$-C$_{10}$ aryl, C$_{10}$ aryl, or phenyl), or R$^{8B}$-substituted or unsubstituted heteroaryl (e.g., 5 to 10 membered heteroaryl, 5 to 9 membered heteroaryl, or 5 to 6 membered heteroaryl).

In embodiments, R$^{8A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{8A}$ is R$^{8B}$-substituted or unsubstituted alkyl (e.g., C$_1$-C$_8$ alkyl, C$_1$-C$_6$ alkyl, or C$_1$-C$_4$ alkyl). In embodiments, R$^{8A}$ is R$^{8B}$-substituted (e.g., C$_1$-C$_8$ alkyl, C$_1$-C$_6$ alkyl, or C$_1$-C$_4$ alkyl). In embodiments, R$^{8A}$ is unsubstituted alkyl (e.g., C$_1$-C$_8$ alkyl, C$_1$-C$_6$ alkyl, or C$_1$-C$_4$ alkyl). In embodiments, R$^{8A}$ is R$^{8B}$-substituted or unsubstituted heteroalkyl (e.g., 2 to 8 membered heteroalkyl, 2 to 6 membered heteroalkyl, or 2 to 4 membered heteroalkyl). In embodiments, R$^{8A}$ is R$^{8B}$-substituted heteroalkyl (e.g., 2 to 8 membered heteroalkyl, 2 to 6 membered heteroalkyl, or 2 to 4 membered heteroalkyl). In embodiments, R$^{8A}$ is unsubstituted heteroalkyl (e.g., 2 to 8 membered heteroalkyl, 2 to 6 membered heteroalkyl, or 2 to 4 membered heteroalkyl). In embodiments, R$^{8A}$ is R$^{8B}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{8A}$ is R$^{8B}$-substituted cycloalkyl (e.g., C$_3$-C$_8$ cycloalkyl, C$_3$-C$_6$ cycloalkyl, or C$_5$-C$_6$ cycloalkyl). In embodiments, R$^{8A}$ is unsubstituted cycloalkyl (e.g., C$_3$-C$_8$ cycloalkyl, C$_3$-C$_6$ cycloalkyl, or C$_5$-C$_6$ cycloalkyl). In embodiments, R$^{8A}$ is R$^{8B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{8A}$ is R$^{8B}$-substituted heterocycloalkyl (e.g., 3 to 8 membered heterocycloalkyl, 3 to 6 membered heterocycloalkyl, or 5 to 6 membered heterocycloalkyl). In embodiments, R$^{8A}$ is unsubstituted heterocycloalkyl (e.g., 3 to 8 membered heterocycloalkyl, 3 to 6 membered heterocycloalkyl, or 5 to 6 membered heterocycloalkyl). In embodiments, R$^{8A}$ is R$^{8B}$-substituted or unsubstituted aryl (e.g., C$_6$-C$_{10}$ aryl, C$_{10}$ aryl, or phenyl). In embodiments, R$^{8A}$ is R$^{8B}$-substituted aryl (e.g., C$_6$-C$_{10}$ aryl, C$_{10}$ aryl, or phenyl). In embodiments, R$^{8A}$ is unsubstituted aryl (e.g., C$_6$-C$_{10}$ aryl, C$_{10}$ aryl, or phenyl). In embodiments, R$^{8A}$ is R$^{8B}$-substituted or unsubstituted heteroaryl (e.g., 5 to 10 membered heteroaryl, 5 to 9 membered heteroaryl, or 5 to 6 membered heteroaryl). In embodiments, $R^{8A}$ is $R^{8B}$-substituted heteroaryl (e.g., 5 to 10 membered heteroaryl, 5 to 9 membered heteroaryl, or 5 to 6 membered heteroaryl). In embodiments, $R^{8A}$ is unsubstituted heteroaryl (e.g., 5 to 10 membered heteroaryl, 5 to 9 membered heteroaryl, or 5 to 6 membered heteroaryl).

$R^{8B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{8B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{8B}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g.$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, ring B is independently a substituted or unsubstituted cycloalkyl, substituted or unsubstituted heterocycloalkyl, substituted or unsubstituted aryl or substituted or unsubstituted heteroaryl. In embodiments, ring B is $R^6$-substituted or unsubstituted cycloalkyl, $R^6$-substituted or unsubstituted heterocycloalkyl, $R^6$-substituted or unsubstituted aryl, or $R^6$-substituted or unsubstituted heteroaryl.

In embodiments, ring B is $R^6$-substituted or unsubstituted cycloalkyl (e.g., $C_3$-$C_8$ cycloalkyl, $C_3$-$C_6$ cycloalkyl, or $C_5$-$C_6$ cycloalkyl), $R^6$-substituted or unsubstituted heterocycloalkyl (e.g., 3 to 8 membered heterocycloalkyl, 3 to 6 membered heterocycloalkyl, or 5 to 6 membered heterocycloalkyl), $R^6$-substituted or unsubstituted aryl (e.g., $C_6$-$C_{10}$ aryl, $C_{10}$ aryl, or phenyl), or $R^6$-substituted or unsubstituted heteroaryl (e.g., 5 to 10 membered heteroaryl, 5 to 9 membered heteroaryl, or 5 to 6 membered heteroaryl).

In embodiments, ring B is $R^6$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, ring B is $R^6$-substituted or unsubstituted cyclopropyl. In embodiments, ring B is $R^6$-substituted cyclopropyl. In embodiments, ring B is unsubstituted cyclopropyl. In embodiments, ring B is $R^6$-substituted or unsubstituted cyclobutyl. In embodiments, ring B is $R^6$-substituted cyclobutyl. In embodiments, ring B is unsubstituted cyclobutyl. In embodiments, ring B is $R^6$-substituted or unsubstituted cyclopentyl. In embodiments, ring B is $R^6$-substituted cyclopentyl. In embodiments, ring B is unsubstituted cyclopentyl. In embodiments, ring B is $R^6$-substituted or unsubstituted cyclohexyl. In embodiments, ring B is $R^6$-substituted cyclohexyl. In embodiments, ring B is unsubstituted cyclohexyl. In embodiments, ring B is $R^6$-substituted or unsubstituted 1-cyclohexenyl. In embodiments, ring B is $R^6$-substituted 1-cyclohexenyl In embodiments, ring B is unsubstituted 1-cyclohexenyl. In embodiments, ring B is $R^6$-substituted or unsubstituted 3-cyclohexenyl. In embodiments, ring B is $R^6$-substituted 3-cyclohexenyl. In embodiments, ring B is unsubstituted 3-cyclohexenyl.

In embodiments, ring B is $R^6$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, ring B is $R^6$-substituted or unsubstituted aziridinyl. In embodiments, ring B is $R^6$-substituted or unsubstituted oxiranyl. In embodiments, ring B is $R^6$-substituted or unsubstituted azetidinyl. In embodiments, ring B is $R^6$-substituted or unsubstituted oxetanyl. In embodiments, ring B is $R^6$-substituted or unsubstituted pyrrolidinyl. In embodiments, ring B is $R^6$-substituted or unsubstituted tetrahydrofuran-2-yl. In embodiments, ring B is $R^6$-substituted or unsubstituted tetrahydrofuran-3-yl. In embodiments, ring B is $R^6$-substituted or unsubstituted 1-piperidinyl. In embodiments, ring B is $R^6$-substituted or unsubstituted 2-piperidinyl. In embodiments, ring B is $R^6$-substituted or unsubstituted 3-piperidinyl. In embodiments, ring B is $R^6$-substituted or unsubstituted tetrahydropyranyl. In embodiments, ring B is $R^6$-substituted or unsubstituted 1-piperazinyl. In embodiments, ring B is $R^6$-substituted or unsubstituted 2-piperazinyl. In embodiments, ring B is $R^6$-substituted or unsubstituted dioxanyl. In embodiments, ring B is $R^6$-substituted or unsubstituted 4-morpholinyl. In embodiments, ring B is $R^6$-substituted or unsubstituted 3-morpholinyl. In embodiments, ring B is $R^6$-substituted or unsubstituted 1-(1,2,5,6-tetrahydropyridyl). In embodiments, ring B is $R^6$-substituted or unsubstituted tetrahydrothien-2-yl. In embodiments, ring B is $R^6$-substituted or unsubstituted tetrahydrothien-3-yl. In embodiments, ring B is $R^6$-substituted or unsubstituted azepanyl. In embodiments, ring B is $R^6$-substituted or unsubstituted diazepanyl. In embodiments, ring B is $R^6$-substituted or unsubstituted 1,3-dioxanyl.

In embodiments, ring B is $R^6$-substituted or unsubstituted 1,3-dioxolanyl. In embodiments, ring B is $R^6$-substituted or unsubstituted 1,3-dithiolanyl. In embodiments, ring B is $R^6$-substituted or unsubstituted 1,3-dithianyl. In embodiments, ring B is $R^6$-substituted or unsubstituted imidazolinyl. In embodiments, ring B is $R^6$-substituted or unsubstituted imidazolidinyl. In embodiments, ring B is $R^6$-substituted or unsubstituted isothiazolinyl. In embodiments, ring B is $R^6$-substituted or unsubstituted isothiazolidinyl. In embodiments, ring B is $R^6$-substituted or unsubstituted isoxazolinyl. In embodiments, ring B is $R^6$-substituted or unsubstituted isoxazolinyl. In embodiments, ring B is $R^6$-substituted or unsubstituted isoxazolinyl. In embodiments, ring B is $R^6$-substituted or unsubstituted isoxazolidinyl. In embodiments, ring B is $R^6$-substituted or unsubstituted morpholinyl. In embodiments, ring B is $R^6$-substituted or unsubstituted oxadiazolinyl. In embodiments, ring B is $R^6$-substituted or unsubstituted oxadiazolidinyl. In embodiments, ring B is $R^6$-substituted or unsubstituted oxazolinyl. In embodiments, ring B is $R^6$-substituted or unsubstituted oxazolidinyl. In embodiments, ring B is $R^6$-substituted or unsubstituted pyranyl. In embodiments, ring B is $R^6$-substituted or unsubstituted pyrazolinyl. In embodiments, ring B is $R^6$-substituted or unsubstituted pyrazolidinyl. In embodiments, ring B is $R^6$-substituted or unsubstituted pyrrolinyl. In embodiments, ring B is $R^6$-substituted or unsubstituted thiadiazolinyl. In embodiments, ring B is $R^6$-substituted or unsubstituted thiazolinyl. In embodiments, ring B is $R^6$-substituted or unsubstituted thiazolidinyl. In embodiments, ring B is $R^6$-substituted or unsubstituted thiomorpholinyl. In embodiments, ring B is $R^6$-substituted or unsubstituted 1,1-dioxidothiomorpholinyl. In embodiments, ring B is $R^6$-substituted or unsubstituted thiopyranyl. In embodiments, ring B is $R^6$-substituted or unsubstituted trithianyl.

In embodiments, ring B is $R^6$-substituted or unsubstituted aryl (e.g., $C_6$-$C_{10}$ aryl, $C_{10}$ aryl, or phenyl). In embodiments, ring B is $R^6$-substituted or unsubstituted phenyl. In embodiments, ring B is $R^6$-substituted phenyl. In embodiments, ring B is unsubstituted phenyl. In embodiments, $R^6$ is halogen. In embodiments, $R^6$ is —Cl.

In embodiments, ring B is $R^6$-substituted or unsubstituted heteroaryl (e.g., 5 to 10 membered heteroaryl, 5 to 9 membered heteroaryl, or 5 to 6 membered heteroaryl). In embodiments, ring B is $R^6$-substituted or unsubstituted pyrrolyl. In embodiments, ring B is $R^6$-substituted or unsubstituted pyrazolyl. In embodiments, ring B is $R^6$-substituted or unsubstituted pyridazinyl. In embodiments, ring B is $R^6$-substituted or unsubstituted triazinyl. In embodiments, ring B is $R^6$-substituted or unsubstituted pyrimidinyl. In embodiments, ring B is $R^6$-substituted or unsubstituted imidazolyl. In embodiments, ring B is $R^6$-substituted or unsubstituted pyrazinyl. In embodiments, ring B is $R^6$-substituted or unsubstituted purinyl. In embodiments, ring B is $R^6$-substituted or unsubstituted purinyl. In embodiments, ring B is $R^6$-substituted or unsubstituted oxazolyl. In embodiments, ring B is $R^6$-substituted or unsubstituted isoxazolyl. In embodiments, ring B is $R^6$-substituted or unsubstituted thiazolyl. In embodiments, ring B is $R^6$-substituted or unsubstituted furyl. In embodiments, ring B is $R^6$-substituted or unsubstituted thienyl. In embodiments, ring B is $R^6$-substituted or unsubstituted pyridyl. In embodiments, ring B is $R^6$-substituted or unsubstituted pyrimidyl. In embodiments, ring B is $R^6$-substituted or unsubstituted benzothiazolyl. In embodiments, ring B is $R^6$-substituted or unsubstituted benzoxazoyl. In embodiments, ring B is $R^6$-substituted or unsubstituted benzimidazolyl. In embodiments, ring B is $R^6$-substituted or unsubstituted benzofuranyl. In embodiments, ring B is $R^6$-substituted or unsubstituted isobenzofuranyl. In embodiments, ring B is $R^6$-substituted or unsubstituted indolyl. In embodiments, ring B is $R^6$-substituted or unsubstituted isoindolyl. In embodiments, ring B is $R^6$-substituted or unsubstituted benzothiophenyl. In embodiments, ring B is $R^6$-substituted or unsubstituted isoquinolyl. In embodiments, ring B is $R^6$-substituted or unsubstituted quinoxalinyl. In embodiments, ring B is $R^6$-substituted or unsubstituted quinolyl. In embodiments, ring B is $R^6$-substituted or unsubstituted 1-naphthyl. In embodiments, ring B is $R^6$-substituted or unsubstituted 2-naphthyl. In embodiments, ring B is $R^6$-substituted or unsubstituted 4-biphenyl. In embodiments, ring B is $R^6$-substituted or unsubstituted 1-pyrrolyl. In embodiments, ring B is $R^6$-substituted or unsubstituted 2-pyrrolyl. In embodiments, ring B is $R^6$-substituted or unsubstituted 3-pyrrolyl. In embodiments, ring B is $R^6$-substituted or unsubstituted 3-pyrrolyl. In embodiments, ring B is $R^6$-substituted or unsubstituted 2-imidazolyl. In embodiments, ring B is $R^6$-substituted or unsubstituted 4-imidazolyl. In embodiments, ring B is $R^6$-substituted or unsubstituted pyrazinyl. In embodiments, ring B is $R^6$-substituted or unsubstituted 2-oxazolyl. In embodiments, ring B is $R^6$-substituted or unsubstituted 4-oxazolyl. In embodiments, ring B is $R^6$-substituted or unsubstituted 2-phenyl-4-oxazolyl. In embodiments, ring B is $R^6$-substituted or unsubstituted 5-oxazolyl. In embodiments, ring B is $R^6$-substituted or unsubstituted 3-isoxazolyl. In embodiments, ring B is $R^6$-substituted or unsubstituted 4-isoxazolyl. In embodiments, ring B is $R^6$-substituted or unsubstituted 5-isoxazolyl. In embodiments, ring B is $R^6$-substituted or unsubstituted 2-thiazolyl. In embodiments, ring B is $R^6$-substituted or unsubstituted 4-thiazolyl. In embodiments, ring B is $R^6$-substituted or unsubstituted 5-thiazolyl. In embodiments, ring B is $R^6$-substituted or unsubstituted 2-furyl. In embodiments, ring B is $R^6$-substituted or unsubstituted 3-furyl. In embodiments, ring B is $R^6$-substituted or unsubstituted 2-thienyl. In embodiments, ring B is $R^6$-substituted or unsubstituted 3-thienyl. In embodiments, ring B is $R^6$-substituted or unsubstituted 2-pyridyl. In embodiments, ring B is $R^6$-substituted or unsubstituted 3-pyridyl. In embodiments, ring B is $R^6$-substituted or unsubstituted 4-pyridyl. In embodiments, ring B is $R^6$-substituted or unsubstituted 2-pyrimidyl. In embodiments, ring B is $R^6$-substituted or unsubstituted 4-pyrimidyl. In embodiments, ring B is $R^6$-substituted or unsubstituted 5-benzothiazolyl. In embodiments, ring B is $R^6$-substituted or unsubstituted 5-benzothiazolyl. In embodiments, ring B is $R^6$-substituted or unsubstituted purinyl. In embodiments, ring B is $R^6$-substituted or unsubstituted 2-benzimidazolyl. In embodiments, ring B is $R^6$-substituted or unsubstituted 5-indolyl. In embodiments, ring B is $R^6$-substituted or unsubstituted 1-isoquinolyl. In embodiments, ring B is $R^6$-substituted or unsubstituted 5-isoquinolyl. In embodiments, ring B is $R^6$-substituted or unsubstituted 2-quinoxalinyl. In embodiments, ring B is $R^6$-substituted or unsubstituted 5-quinoxalinyl. In embodiments, ring B is $R^6$-substituted or unsubstituted 3-quinolyl. In embodiments, ring B is $R^6$-substituted or unsubstituted 6-quinolyl.

In embodiments, ring B is $R^6$-substituted or unsubstituted benzimidazole. In embodiments, ring B is $R^6$-substituted benzimidazole. In embodiments, ring B is unsubstituted benzimidazole. In embodiments, $R^6$ is hydrogen.

$R^6$ is independently hydrogen, halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{6A}$-substituted or unsubstituted alkyl (e.g., $C_1$-$C_8$ alkyl, $C_1$-$C_6$ alkyl, or $C_1$-$C_4$ alkyl), $R^{6A}$-substituted or unsubstituted heteroalkyl (e.g., 2 to 8 membered heteroalkyl, 2 to 6 membered heteroalkyl, or 2 to 4 membered heteroalkyl), $R^{6A}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{6A}$-substituted or unsubstituted heterocycloalkyl (e.g., 3 to 8 membered heterocycloalkyl, 3 to 6 membered heterocycloalkyl, or 5 to 6 membered heterocycloalkyl), $R^{6A}$-substituted or unsubstituted aryl (e.g., $C_6$-$C_{10}$ aryl, $C_{10}$ aryl, or phenyl), or $R^{6A}$-substituted or unsubstituted heteroaryl (e.g., 5 to 10 membered heteroaryl, 5 to 9 membered heteroaryl, or 5 to 6 membered heteroaryl).

In embodiments, $R^6$ is independently hydrogen, halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —$NHC(O)NHNH_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I. In embodiments, R$^6$ is halogen. In embodiments, R$^6$ is —Cl.

In embodiments, R$^6$ is a R$^{6A}$-substituted or unsubstituted alkyl (e.g., C$_1$-C$_8$alkyl, C$_1$-C$_6$ alkyl, or C$_1$-C$_4$ alkyl). In embodiments, R$^6$ is a R$^{6A}$-substituted alkyl (e.g., C$_1$-C$_8$ alkyl, C$_1$-C$_6$ alkyl, or C$_1$-C$_4$ alkyl). In embodiments, R$^6$ is an unsubstituted alkyl (e.g., C$_1$-C$_8$ alkyl, C$_1$-C$_6$ alkyl, or C$_1$-C$_4$ alkyl). In embodiments, R$^6$ is R$^{6A}$-substituted or unsubstituted heteroalkyl (e.g., 2 to 8 membered heteroalkyl, 2 to 6 membered heteroalkyl, or 2 to 4 membered heteroalkyl). In embodiments, R$^6$ is R$^{6A}$-substituted heteroalkyl (e.g., 2 to 8 membered heteroalkyl, 2 to 6 membered heteroalkyl, or 2 to 4 membered heteroalkyl). In embodiments, R$^6$ is an unsubstituted heteroalkyl (e.g., 2 to 8 membered heteroalkyl, 2 to 6 membered heteroalkyl, or 2 to 4 membered heteroalkyl). In embodiments, R$^6$ is R$^{6A}$-substituted or unsubstituted cycloalkyl (e.g., C$_3$-C$_8$ cycloalkyl, C$_3$-C$_6$ cycloalkyl, or C$_5$-C$_6$ cycloalkyl 1). In embodiments, R$^6$ is R$^{6A}$-substituted cycloalkyl (e.g., C$_3$-C$_8$ cycloalkyl, C$_3$-C$_6$ cycloalkyl, or C$_5$-C$_6$ cycloalkyl). In embodiments, R$^6$ is an unsubstituted cycloalkyl (e.g., C$_3$-C$_8$ cycloalkyl, C$_3$-C$_6$ cycloalkyl, or C$_5$-C$_6$ cycloalkyl). In embodiments, R$^6$ is R$^{6A}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^6$ is R$^{6A}$-substituted heterocycloalkyl (e.g., 3 to 8 membered heterocycloalkyl, 3 to 6 membered heterocycloalkyl, or 5 to 6 membered heterocycloalkyl). In embodiments, R$^6$ is an unsubstituted heterocycloalkyl (e.g., 3 to 8 membered heterocycloalkyl, 3 to 6 membered heterocycloalkyl, or 5 to 6 membered heterocycloalkyl). In embodiments, R$^6$ is R$^{6A}$-substituted or unsubstituted aryl (e.g., C$_6$-C$_{10}$ aryl, C$_{10}$ aryl, or phenyl). In embodiments, R$^6$ is R$^{6A}$-substituted aryl (e.g., C$_6$-C$_{10}$ aryl, C$_{10}$ aryl, or phenyl). In embodiments, R$^6$ is an unsubstituted aryl (e.g., C$_6$-C$_{10}$ aryl, C$_{10}$ aryl, or phenyl). In embodiments, R$^6$ is R$^{6A}$-substituted or unsubstituted heteroaryl (e.g., 5 to 10 membered heteroaryl, 5 to 9 membered heteroaryl, or 5 to 6 membered heteroaryl). In embodiments, R$^6$ is R$^{6A}$-substituted heteroaryl (e.g., 5 to 10 membered heteroaryl, 5 to 9 membered heteroaryl, or 5 to 6 membered heteroaryl). In embodiments, R$^6$ is an unsubstituted heteroaryl (e.g., 5 to 10 membered heteroaryl, 5 to 9 membered heteroaryl, or 5 to 6 membered heteroaryl).

R$^{6A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{6B}$-substituted or unsubstituted alkyl (e.g., C$_1$-C$_8$ alkyl, C$_1$-C$_6$ alkyl, or C$_1$-C$_4$ alkyl), R$^{6B}$-substituted or unsubstituted heteroalkyl (e.g., 2 to 8 membered heteroalkyl, 2 to 6 membered heteroalkyl, or 2 to 4 membered heteroalkyl), R$^{6B}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{6B}$-substituted or unsubstituted heterocycloalkyl (e.g., 3 to 8 membered heterocycloalkyl, 3 to 6 membered heterocycloalkyl, or 5 to 6 membered heterocycloalkyl), R$^{6B}$-substituted or unsubstituted aryl (e.g., C$_6$-C$_{10}$ aryl, C$_{10}$ aryl, or phenyl), or R$^{6B}$-substituted or unsubstituted heteroaryl (e.g., 5 to 10 membered heteroaryl, 5 to 9 membered heteroaryl, or 5 to 6 membered heteroaryl).

In embodiments, R$^{6A}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{6A}$ is R$^{6B}$-substituted or unsubstituted alkyl (e.g., C$_1$-C$_8$ alkyl, C$_1$-C$_6$ alkyl, or C$_1$-C$_4$ alkyl). In embodiments, R$^{6A}$ is R$^{6B}$-substituted (e.g., C$_1$-C$_8$ alkyl, C$_1$-C$_6$ alkyl, or C$_1$-C$_4$ alkyl). In embodiments, R$^{6A}$ is unsubstituted alkyl (e.g., C$_1$-C$_8$ alkyl, C$_1$-C$_6$ alkyl, or C$_1$-C$_4$ alkyl). In embodiments, R$^{6A}$ is R$^{6B}$-substituted or unsubstituted heteroalkyl (e.g., 2 to 8 membered heteroalkyl, 2 to 6 membered heteroalkyl, or 2 to 4 membered heteroalkyl). In embodiments, R$^{6A}$ is R$^{6B}$-substituted heteroalkyl (e.g., 2 to 8 membered heteroalkyl, 2 to 6 membered heteroalkyl, or 2 to 4 membered heteroalkyl). In embodiments, R$^{6A}$ is unsubstituted heteroalkyl (e.g., 2 to 8 membered heteroalkyl, 2 to 6 membered heteroalkyl, or 2 to 4 membered heteroalkyl). In embodiments, R$^{6A}$ is R$^{6B}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{6A}$ is R$^{6B}$-substituted cycloalkyl (e.g., C$_3$-C$_8$ cycloalkyl, C$_3$-C$_6$ cycloalkyl, or C$_5$-C$_6$ cycloalkyl). In embodiments, R$^{6A}$ is unsubstituted cycloalkyl (e.g., C$_3$-C$_8$ cycloalkyl, C$_3$-C$_6$ cycloalkyl, or C$_5$-C$_6$ cycloalkyl). In embodiments, R$^{6A}$ is R$^{6B}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{6A}$ is R$^{6B}$-substituted heterocycloalkyl (e.g., 3 to 8 membered heterocycloalkyl, 3 to 6 membered heterocycloalkyl, or 5 to 6 membered heterocycloalkyl). In embodiments, R$^{6A}$ is unsubstituted heterocycloalkyl (e.g., 3 to 8 membered heterocycloalkyl, 3 to 6 membered heterocycloalkyl, or 5 to 6 membered heterocycloalkyl). In embodiments, R$^{6A}$ is R$^{6B}$-substituted or unsubstituted aryl (e.g., C$_6$-C$_{10}$ aryl, C$_{10}$ aryl, or phenyl). In embodiments, R$^{6A}$ is R$^{6B}$-substituted aryl (e.g., C$_6$-C$_{10}$ aryl, C$_{10}$ aryl, or phenyl). In embodiments, R$^{6A}$ is unsubstituted aryl (e.g., C$_6$-C$_{10}$ aryl, C$_{10}$ aryl, or phenyl). In embodiments, R$^{6A}$ is R$^{6B}$-substituted or unsubstituted heteroaryl (e.g., 5 to 10 membered heteroaryl, 5 to 9 membered heteroaryl, or 5 to 6 membered heteroaryl). In embodiments, R$^{6A}$ is R$^{6B}$-substituted heteroaryl (e.g., 5 to 10 membered heteroaryl, 5 to 9 membered heteroaryl, or 5 to 6 membered heteroaryl). In embodiments, R$^{6A}$ is unsubstituted heteroaryl (e.g., 5 to 10 membered heteroaryl, 5 to 9 membered heteroaryl, or 5 to 6 membered heteroaryl).

R$^{6B}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{6B}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{6B}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{10}$ is halogen (e.g., —F, —Cl, Br, —I), —$CX^{10}_3$, —$CHX^{10}_2$, —$CH_2X^{10}$, —$OCX^{10}_3$, —$OCHX^{10}_2$, —$OCH_2X^{10}$, —$S(O)_2R^{10A}$, —$SR^{10A}$, —$S(O)R^{10A}$, —$SO_2NR^{10A}R^{10B}$, —NHC(O)$NR^{10A}R^{10B}$, —$NR^{10A}R^{10B}$, —$NHNR^{10A}R^{10B}$, —C(O)$R^{10A}$, —C(O)—$OR^{10A}$, —C(O)$NR^{10A}R^{10B}$, —C(O)$NHNR^{10A}R^{10B}$, —$OR^{10A}$, —$NR^{10A}SO_2R^{10B}$, —$NR^{10A}C(O)R^{10B}$, —$NR^{10A}C(O)OR^{10B}$, —$NR^{10A}OR^{10B}$, (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, or —$NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^1$ is independently —F, —Cl, —Br, or —I.

In embodiments, $R^{10}$ is —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{10}$ is —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{10}$ is halogen, —OH, —$NH_2$, —SH, substituted or unsubstituted $C_1$-$C_4$ alkyl, or substituted or unsubstituted $C_3$-$C_6$ cycloalkyl. In embodiments, $R^{10}$ is halogen. In embodiments, $R^{10}$ is —F, —Cl, —Br, or —I. In embodiments, $R^{10}$ is —OH. In embodiments, $R^{10}$ is —SH. In embodiments, $R^{10}$ is —$NH_2$. In embodiments, $R^{10}$ is methyl, ethyl, propyl, or butyl. In embodiments, $R^{10}$ is cyclopropyl, cyclobutyl, cyclopentyl, or cyclohexyl.

In embodiments, $R^{12}$ is hydrogen, halogen (e.g., —F, —Cl, Br, —I), —$CX^{12}_3$, —$CHX^{12}_2$, —$CH_2X^{12}$, —$OCX^{12}_3$, —$OCHX^{12}_2$, —$OCH_2X^{12}$, —$S(O)_2R^{12A}$, —$SR^{12A}$, —$S(O)R^{12A}$, —$SO_2NR^{12A}R^{12B}$, —NHC(O)$NR^{12A}R^{12B}$, —$NR^{12A}R^{12B}$, —$NHNR^{12A}R^{12B}$, —C(O)$R^{12A}$, —C(O)—$OR^{12A}$, C(O)$NR^{12A}R^{12B}$, —C(O)$NHNR^{12A}R^{12B}$, —$OR^{12A}$, —$NR^{12A}SO_2R^{12B}$, —$NR^{12A}C(O)R^{12B}$, —$NR^{12A}C(O)OR^{12B}$, $NR^{12A}OR^{12B}$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)

OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, or —NCH₃OCH₃), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^1$ is independently —F, —Cl, —Br, or —I.

In embodiments, $R^{12}$ is hydrogen, —F, —Cl, Br, —I, —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, —NCH₃OCH₃, substituted (e.g., substituted with a substituent group, a size-limited substituent group, or lower substituent group) or unsubstituted alkyl (e.g., $C_1$-$C_5$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{12}$ is hydrogen, —F, —Cl, Br, —I, —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, —NCH₃OCH₃, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{12}$ is hydrogen or substituted or unsubstituted $C_1$-$C_4$ alkyl. In embodiments, $R^{12}$ is hydrogen. In embodiments, $R^{12}$ is methyl.

In embodiments, $R^{14}$ is hydrogen, halogen (e.g., —F, —Cl, Br, —I), —CX$^{14}_3$, —CHX$^{14}_2$, —CH₂X$^{14}$, —OCX$^{14}_3$, —OCHX$^{14}_2$, —OCH₂X$^{14}$, —S(O)₂R$^{14A}$, —SR$^{14A}$, —S(O)R$^{14A}$, —SO₂NR$^{14A}$R$^{14B}$, —NHC(O)NR$^{14A}$R$^{14B}$, —NR$^{14A}$R$^{14B}$, —NHNR$^{14A}$R$^{14B}$, —C(O)R$^{14A}$, —C(O)—OR$^{14A}$, —C(O)NR$^{14A}$R$^{14B}$, —C(O)NHNR$^{14A}$R$^{14B}$, —OR$^{14A}$, —NR$^{14A}$SO₂R$^{14B}$, —NR$^{14A}$C(O)R$^{14B}$, —NR$^{14A}$C(O)OR$^{14B}$, —NR$^{14A}$OR$^{14B}$ (e.g., —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, or —NCH₃OCH₃), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^1$ is independently —F, —Cl, —Br, or —I.

In embodiments, $R^{14}$ is hydrogen, —F, —Cl, Br, —I, —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, —NCH₃OCH₃, substituted (e.g., substituted with a substituent group, a size-limited substituent group, or lower substituent group) or unsubstituted alkyl (e.g., $C_1$-$C_5$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^{14}$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)NH$CH_3$, —$NO_2$, —$NH_2$, —NH$CH_3$, —C(O)H, —C(O)$CH_3$, —C(O)OH, —C(O)O$CH_3$, —C(O)$NH_2$, —C(O)NH$CH_3$, —OH, —$OCH_3$, —NH$SO_2H$, —NH$SO_2CH_3$, —NHC(O)H, —N$CH_3$C(O)H, —NHC(O)OH, —N$CH_3$C(O)OH, —NHOH, —N$CH_3$OH, —N$CH_3$O$CH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^{14}$ is hydrogen, substituted or unsubstituted $C_1$-$C_4$ alkyl, or substituted or unsubstituted $C_3$-$C_6$ cycloalkyl. In embodiments, $R^{14}$ is hydrogen. In embodiments, $R^{14}$ is isobutyl. In embodiments, $R^{14}$ is cyclopropyl. In embodiments, $R^{14}$ is cyclohexyl.

In embodiments, $R^{11}$ is independently —N($R^{14}$)$_2$ or 3 to 7 membered substituted or unsubstituted nitrogen-containing heterocycloalkyl. In embodiments, $R^{11}$ is —N($R^{14}$)$_2$. In embodiments, $R^{11}$ is 3 to 7 membered substituted or unsubstituted nitrogen-containing heterocycloalkyl.

In embodiments, $R^{11}$ is:

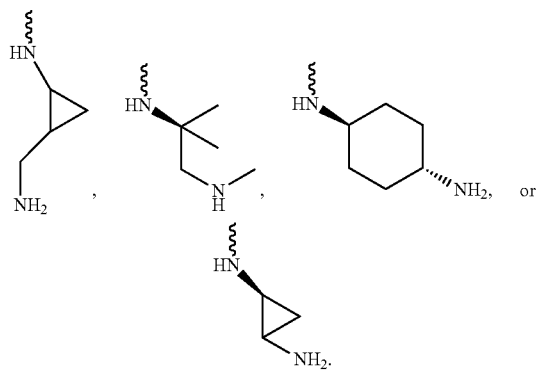

In embodiments, $R^{11}$ is a 3 to 7 membered substituted or unsubstituted nitrogen-containing heterocycloalkyl. In embodiments, $R^{11}$ is a 5 to 6 membered substituted or unsubstituted nitrogen-containing heterocycloalkyl.

In embodiments, $R^{11}$ is $R^5$-substituted or unsubstituted 3 to 7 membered nitrogen-containing heterocycloalkyl. In embodiments, $R^{11}$ is $R^5$-substituted or unsubstituted 5 to 6 membered nitrogen-containing heterocycloalkyl.

In embodiments, $R^{11}$ is $R^5$-substituted or unsubstituted 1-piperidinyl. In embodiments, $R^{11}$ is $R^5$-substituted 1-piperidinyl. In embodiments, $R^{11}$ is unsubstituted 1-piperidinyl. In embodiments, $R^{11}$ is $R^5$-substituted or unsubstituted 2-piperidinyl. In embodiments, $R^{11}$ is $R^5$-substituted 2-piperidinyl. In embodiments, $R^{11}$ is unsubstituted 2-piperidinyl. In embodiments, $R^{11}$ is $R^5$-substituted or unsubstituted 3-piperidinyl. In embodiments, $R^{11}$ is $R^5$-substituted 3-piperidinyl. In embodiments, $R^{11}$ is unsubstituted 3-piperidinyl. In embodiments, $R^{11}$ is $R^5$-substituted or unsubstituted 4-piperidinyl. In embodiments, $R^{11}$ is $R^5$-substituted 4-piperidinyl. In embodiments, $R^{11}$ is unsubstituted 4-piperidinyl. In embodiments, $R^{11}$ is $R^5$-substituted or unsubstituted 5-piperidinyl. In embodiments, $R^{11}$ is $R^5$-substituted 5-piperidinyl. In embodiments, $R^{11}$ is unsubstituted 5-piperidinyl. In embodiments, $R^{11}$ is $R^5$-substituted or unsubstituted 1,4-oxazepanyl. In embodiments, $R^{11}$ is $R^5$-substituted 1,4-oxazepanyl. In embodiments, $R^{11}$ is unsubstituted 1,4-oxazepanyl. In embodiments, $R^{11}$ is $R^5$-substituted or unsubstituted 1,3-oxazepanyl. In embodiments, $R^{11}$ is $R^5$-substituted 1,3-oxazepanyl. In embodiments, $R^{11}$ is unsubstituted 1,3-oxazepanyl. In embodiments, $R^{11}$ is $R^5$-substituted or unsubstituted 1,2-oxazepanyl. In embodiments, $R^{11}$ is $R^5$-substituted 1,2-oxazepanyl. In embodiments, $R^{11}$ is unsubstituted 1,2-oxazepanyl. In embodiments, $R^{11}$ is $R^5$-substituted or unsubstituted piperazinyl. In embodiments, $R^{11}$ is $R^5$-substituted piperazinyl. In embodiments, $R^{11}$ is unsubstituted piperazinyl. In embodiments, $R^{11}$ is $R^5$-substituted or unsubstituted pyrrolidinyl. In embodiments, $R^{11}$ is $R^5$-substituted pyrrolidinyl. In embodiments, $R^{11}$ is unsubstituted pyrrolidinyl. In embodiments, $R^{11}$ is $R^5$-substituted or unsubstituted azetidinyl. In embodiments, $R^{11}$ is $R^5$-substituted azetidinyl. In embodiments, $R^{11}$ is unsubstituted azetidinyl. In embodiments, $R^{11}$ is $R^5$-substituted or unsubstituted aziridinyl. In embodiments, $R^{11}$ is $R^5$-substituted aziridinyl. In embodiments, $R^{11}$ is unsubstituted aziridinyl. In embodiments, $R^{11}$ is $R^5$-substituted or unsubstituted morpholinyl. In embodiments, $R^{11}$ is $R^5$-substituted morpholinyl. In embodiments, $R^{11}$ is unsubstituted morpholinyl. In embodiments, $R^{11}$ is $R^5$-substituted or unsubstituted 3,6-dihydro-2H-1-pyridinyl. In embodiments, $R^{11}$ is $R^5$-substituted 3,6-dihydro-2H-1-pyridinyl. In embodiments, $R^{11}$ is unsubstituted 3,6-dihydro-2H-1-pyridinyl. In embodiments, $R^{11}$ is $R^5$-substituted or unsubstituted pyridinyl. In embodiments, $R^{11}$ is $R^5$-substituted pyridinyl. In embodiments, $R^{11}$ is unsubstituted pyridinyl. In embodiments, $R^{11}$ is $R^5$-substituted or unsubstituted pyrazinyl. In embodiments, $R^{11}$ is $R^5$-substituted pyrazinyl. In embodiments, $R^{11}$ is unsubstituted pyrazinyl. In embodiments, $R^{11}$ is $R^5$-substituted or unsubstituted pyrimidinyl. In embodiments, $R^{11}$ is $R^5$-substituted pyrimidinyl. In embodiments, $R^{11}$ is unsubstituted pyrimidinyl. In embodiments, $R^{11}$ is $R^5$-substituted or unsubstituted pyridazinyl. In embodiments, $R^{11}$ is $R^5$-substituted pyridazinyl. In embodiments, $R^{11}$ is unsubstituted pyridazinyl. In embodiments, $R^{11}$ is $R^5$-substituted or unsubstituted triazinyl. In embodiments, $R^{11}$ is $R^5$-substituted triazinyl. In embodiments, $R^{11}$ is unsubstituted triazinyl.

In embodiments, R[11] is R[5]-substituted or unsubstituted piperidinyl. In embodiments, R[11] is N-methyl-1,4-oxazepan-6-amine. In embodiments, R" is R[5]-substituted or unsubstituted 1-(azetidin-2-yl)-N-methylmethanamine. In embodiments, R[11] is N-methyl-1, 2, 3, 4-tetrahydropyridin-3-amine.

In embodiments, R[11] is

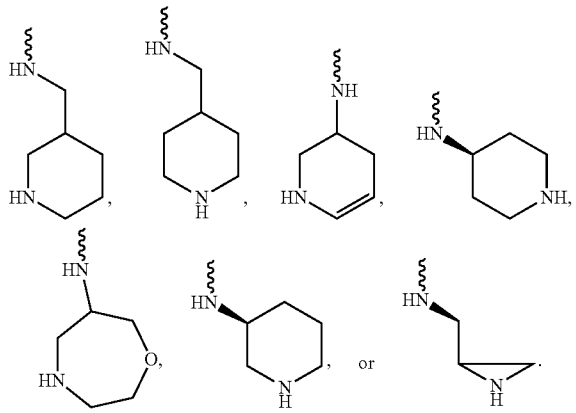

In embodiments, the compound has the formula:

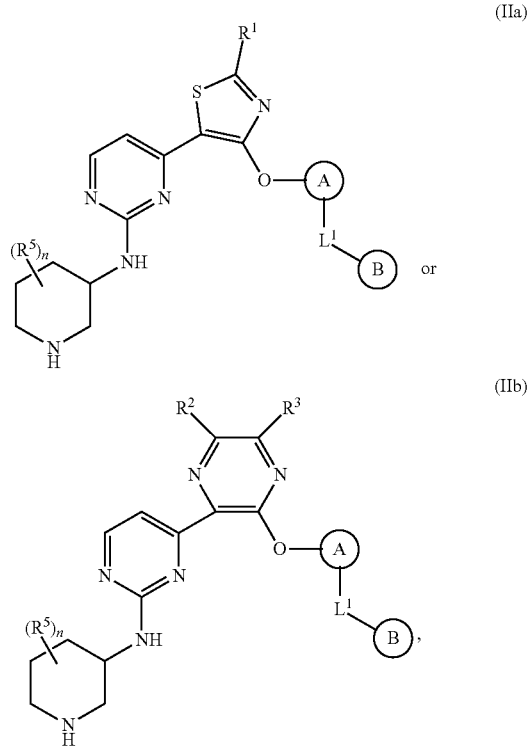

wherein ring A and ring B are as described herein, including embodiments thereof. R[5] is independently halogen, —CX$^5_3$, —CHX$^5_2$, —CH$_2$X$^5$, —OCX$^5_3$, —OCHX$^5_2$, —OCH$_2$X$^5$, —CN, —S(O)$_2$R[5A], —SR[5A], —S(O)R[5A], —SO$_2$NR[5A]R[5B], —NHC(O)NR[5A]R[5B], —N(O)$_2$, —NR[5A]R[5B], —NHNR[5A]R[5B], —C(O)R[5A], —C(O)—OR[5A], —C(O)NR[5A]R[5B], —C(O)NHNR[5A]R[5B], —OR[5A], —NR[5A]SO$_2$R[5B], —NR[5A]C(O)R[5B], —NR[5A]C(O)OR[5B], —NR[5A]OR[5B], —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R[5A] and R[5B] are independently —CX$^5_3$, —CHX$^5_2$, —CH$_2$X$^5$, —C(O)OH, —C(O)NH$_2$, —OH, —NH$_2$, —COOH, —CONH$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R[5A] and R[5B] substituents bonded to the same nitrogen atom may optionally be joined to form a substituted or unsubstituted heterocycloalkyl or substituted or unsubstituted heteroaryl. X$^5$ is halogen. n is an integer from 0 to 5.

In embodiments, R[5] is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R[5']-substituted or unsubstituted alkyl (e.g., C$_1$-C$_8$ alkyl, C$_1$-C$_6$ alkyl, or C$_1$-C$_4$ alkyl), R[5']-substituted or unsubstituted heteroalkyl (e.g., 2 to 8 membered heteroalkyl, 2 to 6 membered heteroalkyl, or 2 to 4 membered heteroalkyl), R[5']-substituted or unsubstituted cycloalkyl (e.g., C$_3$-C$_8$ cycloalkyl, C$_3$-C$_6$ cycloalkyl, or C$_5$-C$_6$ cycloalkyl), R[5']-substituted or unsubstituted heterocycloalkyl (e.g., 3 to 8 membered heterocycloalkyl, 3 to 6 membered heterocycloalkyl, or 5 to 6 membered heterocycloalkyl), R[5']-substituted or unsubstituted aryl (e.g., C$_6$-C$_{10}$ aryl, C$_{10}$ aryl, or phenyl), or R[5']-substituted or unsubstituted heteroaryl (e.g., 5 to 10 membered heteroaryl, 5 to 9 membered heteroaryl, or 5 to 6 membered heteroaryl).

In embodiments, R[5] is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R[5] is R[5']-substituted or unsubstituted alkyl (e.g., C$_1$-C$_8$ alkyl, C$_1$-C$_6$ alkyl, or C$_1$-C$_4$ alkyl). In embodiments, R[5] is R[5']-substituted alkyl (e.g., C$_1$-C$_8$ alkyl, C$_1$-C$_6$ alkyl, or C$_1$-C$_4$ alkyl). In embodiments, R[5] is an unsubstituted alkyl (e.g., C$_1$-C$_8$ alkyl, C$_1$-C$_6$ alkyl, or C$_1$-C$_4$ alkyl). In embodiments, R[5] is R[5']-substituted or unsubstituted heteroalkyl (e.g., 2 to 8 membered heteroalkyl, 2 to 6 membered heteroalkyl, or 2 to 4 membered heteroalkyl). In embodiments, R[5] is R[5']-substituted heteroalkyl (e.g., 2 to 8 membered heteroalkyl, 2 to 6 membered heteroalkyl, or 2 to 4 membered heteroalkyl). In embodiments, R[5] is an unsubstituted heteroalkyl (e.g., 2 to 8 membered heteroalkyl, 2 to 6 membered heteroalkyl, or 2 to 4 membered heteroalkyl). In embodiments, R[5] is R[5']-substituted or unsubstituted cycloalkyl (e.g., C$_3$-C$_8$ cycloalkyl, C$_3$-C$_6$ cycloalkyl, or C$_5$-C$_6$ cycloalkyl 1). In embodiments, R[5] is R[5']-substituted cycloalkyl (e.g., C$_3$-C$_8$ cycloalkyl, C$_3$-C$_6$ cycloalkyl, or C$_5$-C$_6$ cycloalkyl). In embodiments, R[5] is an unsubstituted cycloalkyl (e.g., C$_3$-C$_8$ cycloalkyl, C$_3$-C$_6$ cycloalkyl, or C$_5$-C$_6$ cycloalkyl). In embodiments, R[5] is R[5']-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is $R^{5'}$-substituted heterocycloalkyl (e.g., 3 to 8 membered heterocycloalkyl, 3 to 6 membered heterocycloalkyl, or 5 to 6 membered heterocycloalkyl). In embodiments, $R^5$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^5$ is $R^{5'}$-substituted or unsubstituted aryl (e.g., $C_6$-$C_{10}$ aryl, $C_{10}$ aryl, or phenyl). In embodiments, $R^5$ is $R^{5'}$-substituted aryl (e.g., $C_6$-$C_{10}$ aryl, $C_{10}$ aryl, or phenyl). In embodiments, $R^5$ is an unsubstituted aryl (e.g., $C_6$-$C_{10}$ aryl, $C_{10}$ aryl, or phenyl). In embodiments, $R^5$ is $R^{5'}$-substituted or unsubstituted heteroaryl (e.g., 5 to 10 membered heteroaryl, 5 to 9 membered heteroaryl, or 5 to 6 membered heteroaryl). In embodiments, $R^5$ is $R^{5'}$-substituted heteroaryl (e.g., 5 to 10 membered heteroaryl, 5 to 9 membered heteroaryl, or 5 to 6 membered heteroaryl). In embodiments, $R^5$ is an unsubstituted heteroaryl (e.g., 5 to 10 membered heteroaryl, 5 to 9 membered heteroaryl, or 5 to 6 membered heteroaryl).

$R^{5'}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{5''}$-substituted or unsubstituted alkyl (e.g., $C_1$-$C_8$ alkyl, $C_1$-$C_6$ alkyl, or $C_1$-$C_4$ alkyl), $R^{5''}$-substituted or unsubstituted heteroalkyl (e.g., 2 to 8 membered heteroalkyl, 2 to 6 membered heteroalkyl, or 2 to 4 membered heteroalkyl), $R^{5''}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{5''}$-substituted or unsubstituted heterocycloalkyl (e.g., 3 to 8 membered heterocycloalkyl, 3 to 6 membered heterocycloalkyl, or 5 to 6 membered heterocycloalkyl), $R^{5''}$-substituted or unsubstituted aryl (e.g., $C_6$-$C_{10}$ aryl, $C_{10}$ aryl, or phenyl), or $R^{5''}$-substituted or unsubstituted heteroaryl (e.g., 5 to 10 membered heteroaryl, 5 to 9 membered heteroaryl, or 5 to 6 membered heteroaryl).

In embodiments, $R^{5'}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{5'}$ is $R^{5''}$-substituted or unsubstituted alkyl (e.g., $C_1$-$C_8$ alkyl, $C_1$-$C_6$ alkyl, or $C_1$-$C_4$ alkyl). In embodiments, $R^{5'}$ is $R^{5''}$-substituted (e.g., $C_1$-$C_8$ alkyl, $C_1$-$C_6$ alkyl, or $C_1$-$C_4$ alkyl). In embodiments, $R^{5'}$ is unsubstituted alkyl (e.g., $C_1$-$C_8$ alkyl, $C_1$-$C_6$ alkyl, or $C_1$-$C_4$ alkyl). In embodiments, $R^{5'}$ is $R^{5''}$-substituted or unsubstituted heteroalkyl (e.g., 2 to 8 membered heteroalkyl, 2 to 6 membered heteroalkyl, or 2 to 4 membered heteroalkyl). In embodiments, $R^{5'}$ is $R^{5''}$-substituted heteroalkyl (e.g., 2 to 8 membered heteroalkyl, 2 to 6 membered heteroalkyl, or 2 to 4 membered heteroalkyl). In embodiments, $R^{5'}$ is unsubstituted heteroalkyl (e.g., 2 to 8 membered heteroalkyl, 2 to 6 membered heteroalkyl, or 2 to 4 membered heteroalkyl). In embodiments, $R^{5'}$ is $R^{5''}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5'}$ is $R^{5''}$-substituted cycloalkyl (e.g., $C_3$-$C_8$ cycloalkyl, $C_3$-$C_6$ cycloalkyl, or $C_5$-$C_6$ cycloalkyl). In embodiments, $R^{5'}$ is unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5'}$ is $R^{5''}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{5'}$ is $R^{5''}$-substituted heterocycloalkyl (e.g., 3 to 8 membered heterocycloalkyl, 3 to 6 membered heterocycloalkyl, or 5 to 6 membered heterocycloalkyl). In embodiments, $R^{5'}$ is unsubstituted heterocycloalkyl (e.g., 3 to 8 membered heterocycloalkyl, 3 to 6 membered heterocycloalkyl, or 5 to 6 membered heterocycloalkyl). In embodiments, $R^{5'}$ is $R^{5''}$-substituted or unsubstituted aryl (e.g., $C_6$-$C_{10}$ aryl, $C_{10}$ aryl, or phenyl). In embodiments, $R^{5'}$ is $R^{5''}$-substituted aryl (e.g., $C_6$-$C_{10}$ aryl, $C_{10}$ aryl, or phenyl). In embodiments, $R^{5'}$ is unsubstituted aryl (e.g., $C_6$-$C_{10}$ aryl, $C_{10}$ aryl, or phenyl). In embodiments, $R^{5'}$ is $R^{5''}$-substituted or unsubstituted heteroaryl (e.g., 5 to 10 membered heteroaryl, 5 to 9 membered heteroaryl, or 5 to 6 membered heteroaryl). In embodiments, $R^{5'}$ is $R^{5''}$-substituted heteroaryl (e.g., 5 to 10 membered heteroaryl, 5 to 9 membered heteroaryl, or 5 to 6 membered heteroaryl). In embodiments, $R^{5'}$ is unsubstituted heteroaryl (e.g., 5 to 10 membered heteroaryl, 5 to 9 membered heteroaryl, or 5 to 6 membered heteroaryl).

$R^{5''}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{5''}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{5''}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

$R^{5A}$ is independently —$CX^5_3$, —$CHX^5_2$, —$CH_2X^5$, —C(O)OH, —C(O)$NH_2$, —OH, —$NH_2$, —COOH, —$CONH_2$, —SH, —$SO_3H$, —$SO_4H$, —$SO_2NH_2$, —$NHNH_2$, —$ONH_2$, —NHC(O)$NHNH_2$, —NHC=(O)$NH_2$, —$NHSO_2H$, —NHC=(O)H, —NHC(O)OH, —NHOH, —$OCX^5_3$, —$OCHX^5_2$, —$OCH_2X^5$, $R^{5A'}$-substituted or unsubstituted alkyl (e.g., $C_1$-$C_8$ alkyl, $C_1$-$C_6$ alkyl, or $C_1$-$C_4$ alkyl), $R^{54'}$-substituted or unsubstituted heteroalkyl (e.g., 2 to 8 membered heteroalkyl, 2 to 6 membered heteroalkyl, or 2 to 4 membered heteroalkyl), $R^{54'}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{54'}$-substituted or unsubstituted heterocycloalkyl (e.g., 3 to 8 membered heterocycloalkyl, 3 to 6 membered heterocycloalkyl, or 5 to 6 membered heterocycloalkyl), $R^{54'}$-substituted or unsubstituted aryl (e.g., $C_6$-$C_{10}$ aryl, $C_{10}$ aryl, or phenyl), or $R^{54'}$-substituted or unsubstituted heteroaryl (e.g., 5 to 10 membered heteroaryl, 5 to 9 membered heteroaryl, or 5 to 6 membered heteroaryl).

In embodiments, $R^{54}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{54}$ is $R^{54'}$-substituted or unsubstituted alkyl (e.g., $C_1$-$C_5$ alkyl, $C_1$-$C_6$ alkyl, or $C_1$-$C_4$ alkyl). In embodiments, $R^{54}$ is $R^{54'}$-substituted (e.g., $C_1$-$C_5$ alkyl, $C_1$-$C_6$ alkyl, or $C_1$-$C_4$ alkyl). In embodiments, $R^{54}$ is unsubstituted alkyl (e.g., $C_1$-$C_5$ alkyl, $C_1$-$C_6$ alkyl, or $C_1$-$C_4$ alkyl). In embodiments, $R^{54}$ is $R^{54'}$-substituted or unsubstituted heteroalkyl (e.g., 2 to 8 membered heteroalkyl, 2 to 6 membered heteroalkyl, or 2 to 4 membered heteroalkyl). In embodiments, $R^{54}$ is $R^{54'}$-substituted heteroalkyl (e.g., 2 to 8 membered heteroalkyl, 2 to 6 membered heteroalkyl, or 2 to 4 membered heteroalkyl). In embodiments, $R^{54}$ is unsubstituted heteroalkyl (e.g., 2 to 8 membered heteroalkyl, 2 to 6 membered heteroalkyl, or 2 to 4 membered heteroalkyl). In embodiments, $R^{54}$ is $R^{54'}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{54}$ is $R^{54'}$-substituted cycloalkyl (e.g., $C_3$-$C_8$ cycloalkyl, $C_3$-$C_6$ cycloalkyl, or $C_5$-$C_6$ cycloalkyl). In embodiments, $R^{54}$ is unsubstituted cycloalkyl (e.g., $C_3$-$C_8$ cycloalkyl, $C_3$-$C_6$ cycloalkyl, or $C_5$-$C_6$ cycloalkyl). In embodiments, $R^{54}$ is $R^{54'}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{54}$ is $R^{54'}$-substituted heterocycloalkyl (e.g., 3 to 8 membered heterocycloalkyl, 3 to 6 membered heterocycloalkyl, or 5 to 6 membered heterocycloalkyl). In embodiments, $R^{54}$ is unsubstituted heterocycloalkyl (e.g., 3 to 8 membered heterocycloalkyl, 3 to 6 membered heterocycloalkyl, or 5 to 6 membered heterocycloalkyl). In embodiments, $R^{54}$ is $R^{54'}$-substituted or unsubstituted aryl (e.g., $C_6$-$C_{10}$ aryl, $C_{10}$ aryl, or phenyl). In embodiments, $R^{54}$ is $R^{54'}$-substituted aryl (e.g., $C_6$-$C_{10}$ aryl, $C_{10}$ aryl, or phenyl). In embodiments, $R^{54}$ is unsubstituted aryl (e.g., $C_6$-$C_{10}$ aryl, $C_{10}$ aryl, or phenyl). In embodiments, $R^{54}$ is $R^{54'}$-substituted or unsubstituted heteroaryl (e.g., 5 to 10 membered heteroaryl, 5 to 9 membered heteroaryl, or 5 to 6 membered heteroaryl). In embodiments, $R^{54}$ is $R^{54'}$-substituted heteroaryl (e.g., 5 to 10 membered heteroaryl, 5 to 9 membered heteroaryl, or 5 to 6 membered heteroaryl). In embodiments, $R^{54}$ is unsubstituted heteroaryl (e.g., 5 to 10 membered heteroaryl, 5 to 9 membered heteroaryl, or 5 to 6 membered heteroaryl).

$R^{54'}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{54''}$-substituted or unsubstituted alkyl (e.g., $C_1$-$C_8$ alkyl, $C_1$-$C_6$ alkyl, or $C_1$-$C_4$ alkyl), $R^{54''}$-substituted or unsubstituted heteroalkyl (e.g., 2 to 8 membered heteroalkyl, 2 to 6 membered heteroalkyl, or 2 to 4 membered heteroalkyl), $R^{54''}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{54''}$-substituted or unsubstituted heterocycloalkyl (e.g., 3 to 8 membered heterocycloalkyl, 3 to 6 membered heterocycloalkyl, or 5 to 6 membered heterocycloalkyl), $R^{54''}$-substituted or unsubstituted aryl (e.g., $C_6$-$C_{10}$ aryl, $C_{10}$ aryl, or phenyl), or $R^{54''}$-substituted or unsubstituted heteroaryl (e.g., 5 to 10 membered heteroaryl, 5 to 9 membered heteroaryl, or 5 to 6 membered heteroaryl).

In embodiments, $R^{54'}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, or —$OCH_2I$.

In embodiments, $R^{54'}$ is $R^{54''}$-substituted or unsubstituted alkyl (e.g., $C_1$-$C_8$ alkyl, $C_1$-$C_6$ alkyl, or $C_1$-$C_4$ alkyl). In embodiments, $R^{54'}$ is $R^{54''}$-substituted (e.g., $C_1$-$C_5$ alkyl, $C_1$-$C_6$ alkyl, or $C_1$-$C_4$ alkyl). In embodiments, $R^{54'}$ is unsubstituted alkyl (e.g., $C_1$-$C_8$ alkyl, $C_1$-$C_6$ alkyl, or $C_1$-$C_4$ alkyl). In embodiments, $R^{54'}$ is $R^{54''}$-substituted or unsubstituted heteroalkyl (e.g., 2 to 8 membered heteroalkyl, 2 to 6 membered heteroalkyl, or 2 to 4 membered heteroalkyl). In embodiments, $R^{54'}$ is $R^{54''}$-substituted heteroalkyl (e.g., 2 to 8 membered heteroalkyl, 2 to 6 membered heteroalkyl, or 2 to 4 membered heteroalkyl). In embodiments, $R^{54'}$ is unsubstituted heteroalkyl (e.g., 2 to 8 membered heteroalkyl, 2 to 6 membered heteroalkyl, or 2 to 4 membered heteroalkyl). In embodiments, $R^{54'}$ is $R^{54''}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{54'}$ is $R^{54''}$-substituted cycloalkyl (e.g., $C_3$-$C_8$ cycloalkyl, $C_3$-$C_6$ cycloalkyl, or $C_5$-$C_6$ cycloalkyl). In embodiments, $R^{54'}$ is unsubstituted cycloalkyl (e.g., $C_3$-$C_8$ cycloalkyl, $C_3$-$C_6$ cycloalkyl, or $C_5$-$C_6$ cycloalkyl). In embodiments, $R^{54'}$ is $R^{54''}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{54'}$ is $R^{54''}$-substituted heterocycloalkyl (e.g., 3 to 8 membered heterocycloalkyl, 3 to 6 membered heterocycloalkyl, or 5 to 6 membered heterocycloalkyl). In embodiments, $R^{54'}$ is unsubstituted heterocycloalkyl (e.g., 3 to 8 membered heterocycloalkyl, 3 to 6 membered heterocycloalkyl, or 5 to 6 membered heterocycloalkyl). In embodiments, $R^{54'}$ is $R^{54''}$-substituted or unsubstituted aryl (e.g., $C_6$-$C_{10}$ aryl, $C_{10}$ aryl, or phenyl). In embodiments, $R^{54'}$ is $R^{54''}$-substituted aryl (e.g., $C_6$-$C_{10}$ aryl, $C_{10}$ aryl, or phenyl). In embodiments, $R^{54'}$ is unsubstituted aryl (e.g., $C_6$-$C_{10}$ aryl, $C_{10}$ aryl, or phenyl). In embodiments, $R^{54'}$ is $R^{54''}$-substituted or unsubstituted heteroaryl (e.g., 5 to 10 membered heteroaryl, 5 to 9 membered heteroaryl, or 5 to 6 membered heteroaryl). In embodiments, $R^{54'}$ is $R^{54''}$-substituted heteroaryl (e.g., 5 to 10 membered heteroaryl, 5 to 9 membered heteroaryl, or 5 to 6 membered heteroaryl). In embodiments, $R^{54'}$ is unsubstituted heteroaryl (e.g., 5 to 10 membered heteroaryl, 5 to 9 membered heteroaryl, or 5 to 6 membered heteroaryl).

$R^{54''}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC (O)—OH, —NHOH, —OCF$_3$, —OCCl$_3$, —OCBr$_3$, OCl$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, R$^{5A''}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCl$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{5A''}$ is independently unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

R$^{5B}$ is independently —CX$^5_3$, —CHX$^5_2$, —CH$_2$X$^5$, —C(O)OH, —C(O)NH$_2$, —OH, —NH$_2$, —COOH, —CONH$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, R$^{5B'}$-substituted or unsubstituted alkyl (e.g., C$_1$-C$_8$ alkyl, C$_1$-C$_6$ alkyl, or C$_1$-C$_4$ alkyl), R$^{5B'}$-substituted or unsubstituted heteroalkyl (e.g., 2 to 8 membered heteroalkyl, 2 to 6 membered heteroalkyl, or 2 to 4 membered heteroalkyl), R$^{5B'}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{5B'}$-substituted or unsubstituted heterocycloalkyl (e.g., 3 to 8 membered heterocycloalkyl, 3 to 6 membered heterocycloalkyl, or 5 to 6 membered heterocycloalkyl), R$^{5B'}$-substituted or unsubstituted aryl (e.g., C$_6$-C$_{10}$ aryl, C$_{10}$ aryl, or phenyl), or R$^{5B'}$-substituted or unsubstituted heteroaryl (e.g., 5 to 10 membered heteroaryl, 5 to 9 membered heteroaryl, or 5 to 6 membered heteroaryl).

In embodiments, R$^{5B}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCl$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{5B}$ is R$^{5B'}$-substituted or unsubstituted alkyl (e.g., C$_1$-C$_8$ alkyl, C$_1$-C$_6$ alkyl, or C$_1$-C$_4$ alkyl). In embodiments, R$^{5B}$ is R$^{5B'}$-substituted (e.g., C$_1$-C$_8$ alkyl, C$_1$-C$_6$ alkyl, or C$_1$-C$_4$ alkyl). In embodiments, R$^{5B}$ is unsubstituted alkyl (e.g., C$_1$-C$_8$ alkyl, C$_1$-C$_6$ alkyl, or C$_1$-C$_4$ alkyl). In embodiments, R$^{5B}$ is R$^{5B'}$-substituted or unsubstituted heteroalkyl (e.g., 2 to 8 membered heteroalkyl, 2 to 6 membered heteroalkyl, or 2 to 4 membered heteroalkyl). In embodiments, R$^{5B}$ is R$^{5B'}$-substituted heteroalkyl (e.g., 2 to 8 membered heteroalkyl, 2 to 6 membered heteroalkyl, or 2 to 4 membered heteroalkyl). In embodiments, R$^{5B}$ is unsubstituted heteroalkyl (e.g., 2 to 8 membered heteroalkyl, 2 to 6 membered heteroalkyl, or 2 to 4 membered heteroalkyl). In embodiments, R$^{5B}$ is R$^{5B'}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{5B}$ is R$^{5B'}$-substituted cycloalkyl (e.g., C$_3$-C$_8$ cycloalkyl, C$_3$-C$_6$ cycloalkyl, or C$_5$-C$_6$ cycloalkyl). In embodiments, R$^{5B}$ is unsubstituted cycloalkyl (e.g., C$_3$-C$_8$ cycloalkyl, C$_3$-C$_6$ cycloalkyl, or C$_5$-C$_6$ cycloalkyl). In embodiments, R$^{5B}$ is R$^{5B'}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{5B}$ is R$^{5B'}$-substituted heterocycloalkyl (e.g., 3 to 8 membered heterocycloalkyl, 3 to 6 membered heterocycloalkyl, or 5 to 6 membered heterocycloalkyl). In embodiments, R$^{5B}$ is unsubstituted heterocycloalkyl (e.g., 3 to 8 membered heterocycloalkyl, 3 to 6 membered heterocycloalkyl, or 5 to 6 membered heterocycloalkyl). In embodiments, R$^{5B}$ is R$^{5B'}$-substituted or unsubstituted aryl (e.g., C$_6$-C$_{10}$ aryl, C$_{10}$ aryl, or phenyl). In embodiments, R$^{5B}$ is R$^{5B'}$-substituted aryl (e.g., C$_6$-C$_{10}$ aryl, C$_{10}$ aryl, or phenyl). In embodiments, R$^{5B}$ is unsubstituted aryl (e.g., C$_6$-C$_{10}$ aryl, C$_{10}$ aryl, or phenyl). In embodiments, R$^{5B}$ is R$^{5B'}$-substituted or unsubstituted heteroaryl (e.g., 5 to 10 membered heteroaryl, 5 to 9 membered heteroaryl, or 5 to 6 membered heteroaryl). In embodiments, R$^{5B}$ is R$^{5B'}$-substituted heteroaryl (e.g., 5 to 10 membered heteroaryl, 5 to 9 membered heteroaryl, or 5 to 6 membered heteroaryl). In embodiments, R$^{5B}$ is unsubstituted heteroaryl (e.g., 5 to 10 membered heteroaryl, 5 to 9 membered heteroaryl, or 5 to 6 membered heteroaryl).

R$^{5B'}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCl$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, —OCH$_2$I, R$^{5B''}$-substituted or unsubstituted alkyl (e.g., C$_1$-C$_8$ alkyl, C$_1$-C$_6$ alkyl, or C$_1$-C$_4$ alkyl), R$^{5B''}$-substituted or unsubstituted heteroalkyl (e.g., 2 to 8 membered heteroalkyl, 2 to 6 membered heteroalkyl, or 2 to 4 membered heteroalkyl), R$^{5B''}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{5B''}$-substituted or unsubstituted heterocycloalkyl (e.g., 3 to 8 membered heterocycloalkyl, 3 to 6 membered heterocycloalkyl, or 5 to 6 membered heterocycloalkyl), R$^{5B''}$-substituted or unsubstituted aryl (e.g., C$_6$-C$_{10}$ aryl, C$_{10}$ aryl, or phenyl), or R$^{5B''}$-substituted or unsubstituted heteroaryl (e.g., 5 to 10 membered heteroaryl, 5 to 9 membered heteroaryl, or 5 to 6 membered heteroaryl).

In embodiments, R$^{5B'}$ is independently halogen, —CF$_3$, —CCl$_3$, —CBr$_3$, —CI$_3$, —OH, —NH$_2$, —COOH, —CONH$_2$, —NO$_2$, —N$_3$, —SH, —SO$_3$H, —SO$_4$H, —SO$_2$NH$_2$, —NHNH$_2$, —ONH$_2$, —NHC(O)NHNH$_2$, —NHSO$_2$H, —NHC(O)H, —NHC(O)—OH, —NHOH, —OCF$_3$, —OCCl$_3$, —OCBr$_3$, OCl$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —OCH$_2$F, —OCH$_2$Cl, —OCH$_2$Br, or —OCH$_2$I.

In embodiments, R$^{5B'}$ is R$^{5B''}$-substituted or unsubstituted alkyl (e.g., C$_1$-C$_8$ alkyl, C$_1$-C$_6$ alkyl, or C$_1$-C$_4$ alkyl). In embodiments, R$^{5B'}$ is R$^{5B''}$-substituted (e.g., C$_1$-C$_8$ alkyl, C$_1$-C$_6$ alkyl, or C$_1$-C$_4$ alkyl). In embodiments, R$^{5B'}$ is unsubstituted alkyl (e.g., $C_1$-$C_8$ alkyl, $C_1$-$C_6$ alkyl, or $C_1$-$C_4$ alkyl). In embodiments, $R^{5B'}$ is $R^{5B''}$-substituted or unsubstituted heteroalkyl (e.g., 2 to 8 membered heteroalkyl, 2 to 6 membered heteroalkyl, or 2 to 4 membered heteroalkyl). In embodiments, $R^{5B'}$ is $R^{5B''}$-substituted heteroalkyl (e.g., 2 to 8 membered heteroalkyl, 2 to 6 membered heteroalkyl, or 2 to 4 membered heteroalkyl). In embodiments, $R^{5B'}$ is unsubstituted heteroalkyl (e.g., 2 to 8 membered heteroalkyl, 2 to 6 membered heteroalkyl, or 2 to 4 membered heteroalkyl). In embodiments, $R^{5B'}$ is $R^{5B''}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5B'}$ is $R^{5B''}$-substituted cycloalkyl (e.g., $C_3$-$C_8$ cycloalkyl, $C_3$-$C_6$ cycloalkyl, or $C_5$-$C_6$ cycloalkyl). In embodiments, $R^{5B'}$ is unsubstituted cycloalkyl (e.g., $C_3$-$C_8$ cycloalkyl, $C_3$-$C_6$ cycloalkyl, or $C_5$-$C_6$ cycloalkyl). In embodiments, $R^{5B'}$ is $R^{5B''}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{5B'}$ is $R^{5B''}$-substituted heterocycloalkyl (e.g., 3 to 8 membered heterocycloalkyl, 3 to 6 membered heterocycloalkyl, or 5 to 6 membered heterocycloalkyl). In embodiments, $R^{5B'}$ is unsubstituted heterocycloalkyl (e.g., 3 to 8 membered heterocycloalkyl, 3 to 6 membered heterocycloalkyl, or 5 to 6 membered heterocycloalkyl). In embodiments, $R^{5B'}$ is $R^{5B''}$-substituted or unsubstituted aryl (e.g., $C_6$-$C_{10}$ aryl, $C_{10}$ aryl, or phenyl). In embodiments, $R^{5B'}$ is $R^{5B''}$-substituted aryl (e.g., $C_6$-$C_{10}$ aryl, $C_{10}$ aryl, or phenyl). In embodiments, $R^{5B'}$ is unsubstituted aryl (e.g., $C_6$-$C_{10}$ aryl, $C_{10}$ aryl, or phenyl). In embodiments, $R^{5B'}$ is $R^{5B''}$-substituted or unsubstituted heteroaryl (e.g., 5 to 10 membered heteroaryl, 5 to 9 membered heteroaryl, or 5 to 6 membered heteroaryl). In embodiments, $R^{5B'}$ is $R^{5B''}$-substituted heteroaryl (e.g., 5 to 10 membered heteroaryl, 5 to 9 membered heteroaryl, or 5 to 6 membered heteroaryl). In embodiments, $R^{5B'}$ is unsubstituted heteroaryl (e.g., 5 to 10 membered heteroaryl, 5 to 9 membered heteroaryl, or 5 to 6 membered heteroaryl).

$R^{5B''}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{5B''}$ is independently halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCl_3$, —$OCHF_2$, —$OCHCl_2$, —$OCHBr_2$, —$OCHI_2$, —$OCH_2F$, —$OCH_2Cl$, —$OCH_2Br$, or —$OCH_2I$.

In embodiments, $R^{5B''}$ is independently unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^5$ is halogen. In embodiments, $R^5$ is —F.

In embodiments, n is 0.

In embodiments, $R^1$ is hydrogen, halogen (e.g., —F, —Cl, Br, —I), —$CX^1_3$, —$CHX^1Z$, —$CH_2X^1$, —$OCX^1_3$, —$OCHX^{1Z}$, —$OCH_2X^1$, —CN, —$S(O)_2R^{1A}$, —$SR^{1A}$, —$S(O)R^{1A}$, —$SO_2NR^{1A}R^{1B}$, —$NHC(O)NR^{1A}R^{1B}$, —$N(O)_2$, —$NR^{1A}R^{1B}$, —$NHNR^{1A}R^{1B}$, —$C(O)R^{1A}$, —C(O)—$OR^{1A}$, —$C(O)NR^{1A}R^{1B}$, —$C(O)NHNR^{1A}R^{1B}$, —$OR^{1A}$, —$NR^{1A}SO_2R^{1B}$, —$NR^{1A}C(O)R^{1B}$, —$NR^{1A}C(O)OR^{1B}$, —$NR^{1A}OR^{1B}$, —$N_3$, (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O) OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, or —$NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^1$ is independently —F, —Cl, —Br, or —I.

In embodiments, $R^1$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^1$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^1$ is hydrogen, halogen, —OH, —$NH_2$, —SH, substituted or unsubstituted $C_1$-$C_3$ alkyl, or substituted or unsubstituted $C_3$-$C_6$ cycloalkyl. In embodiments, $R^1$ is hydrogen. In embodiments, $R^1$ is halogen. In embodiments, $R^1$ is —F, —Cl, —Br, or —I. In embodiments, $R^1$ is —OH. In embodiments, $R^1$ is —$NH_2$. In embodiments, $R^1$ is —SH. In embodiments, $R^1$ is unsubstituted $C_1$-$C_3$ alkyl. In embodiments, $R^1$ is methyl. In embodiments, $R^1$ is unsubstituted $C_3$-$C_6$ cycloalkyl. In embodiments, $R^1$ is cyclopropyl, cyclobutyl, cycloperthyl, or cyclohexyl.

In embodiments, $R^2$ is hydrogen, halogen (e.g., —F, —Cl, Br, —I), —$CX^2_3$, —$CHX^2_2$, —$CH_2X^2$, —$OCX^2_3$, —$OCHX^2_2$, —$OCH_2X^2$, —CN, —S(O)$_2R^{2A}$, —$SR^{2A}$, —S(O)$R^{2A}$, —$SO_2NR^{2A}R^{2B}$, —NHC(O)$NR^{2A}R^{2B}$, —N(O)$_2$, —$NR^{2A}R^{2B}$, —$NHNR^{2A}R^{2B}$, —C(O)$R^{2A}$, —C(O)—$OR^{2A}$, —C(O)$NR^{2A}R^{2B}$, —C(O)$NHNR^{2A}R^{2B}$, —$OR^{2A}$, —$NR^{2A}SO_2R^{2B}$, —$NR^{2A}$C(O)$R^{2B}$, —$NR^{2A}$C(O)$OR^{2B}$, —$NR^{2A}OR^{2B}$, —$N_3$, (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —NHOH, —$NCH_3$OH, or —$NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^1$ is independently —F, —Cl, —Br, or —I.

In embodiments, $R^2$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^2$ is hydrogen, halogen, —OH, —$NH_2$, —SH, substituted or unsubstituted $C_1$-$C_3$ alkyl, or substituted or unsubstituted $C_3$-$C_6$ cycloalkyl. In embodiments, $R^2$ is hydrogen. In embodiments, $R^2$ is halogen. In embodiments, $R^2$ is —F, —Cl, —Br, or —I. In embodiments, $R^2$ is —OH. In embodiments, $R^2$ is —$NH_2$. In embodiments, $R^2$ is —SH. In embodiments, $R^2$ is unsubstituted $C_1$-$C_3$ alkyl. In embodiments, $R^2$ is methyl. In embodiments, $R^2$ is unsubstituted $C_3$-$C_6$ cycloalkyl. In embodiments, $R^2$ is cyclopropyl, cyclobutyl, cycloperthyl, or cyclohexyl.

In embodiments, $R^3$ is hydrogen, halogen (e.g., —F, —Cl, Br, —I), —$CX^3_3$, —$CHX^3_2$, —$CH_2X^3$, —$OCX^3_3$, —$OCHX^3_2$, —$OCH_2X^3$, —CN, —$S(O)_2R^{3A}$, —$SR^{3A}$, —$S(O)R^{3A}$, —$SO_2NR^{3A}R^{3B}$, —$NHC(O)NR^{3A}R^{3B}$, —$N(O)_2$, —$NR^{3A}R^{3B}$, —$NHNR^{3A}R^{3B}$, —$C(O)R^{3A}$, —$C(O)$—$OR^{3A}$, —$C(O)NR^{3A}R^{3B}$, —$C(O)NHNR^{3A}R^{3B}$, —$OR^{3A}$, —$NR^{3A}SO_2R^{3B}$, —$NR^{3A}C(O)R^{3B}$, —$NR^{3A}C(O)OR^{3B}$, —$NR^{3A}OR^{3B}$, —$N_3$, (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —$C(O)H$, —$C(O)CH_3$, —$C(O)OH$, —$C(O)OCH_3$, —$C(O)NH_2$, —$C(O)NHCH_3$, —OH, —$OCH_3$, —$NHSO_2H$, —$NHSO_2CH_3$, —$NHC(O)H$, —$NCH_3C(O)H$, —$NHC(O)OH$, —$NCH_3C(O)OH$, —NHOH, —$NCH_3OH$, or —$NCH_3OCH_3$), substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). $X^1$ is independently —F, —Cl, —Br, or —I.

In embodiments, $R^3$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —$C(O)H$, —$C(O)CH_3$, —$C(O)OH$, —$C(O)OCH_3$, —$C(O)NH_2$, —$C(O)NHCH_3$, —OH, —$OCH_3$, —$NHSO_2H$, —$NHSO_2CH_3$, —$NHC(O)H$, —$NCH_3C(O)H$, —$NHC(O)OH$, —$NCH_3C(O)OH$, —NHOH, —$NCH_3OH$, —$NCH_3OCH_3$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_6$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, $R^3$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —$C(O)H$, —$C(O)CH_3$, —$C(O)OH$, —$C(O)OCH_3$, —$C(O)NH_2$, —$C(O)NHCH_3$, —OH, —$OCH_3$, —$NHSO_2H$, —$NHSO_2CH_3$, —$NHC(O)H$, —$NCH_3C(O)H$, —$NHC(O)OH$, —$NCH_3C(O)OH$, —NHOH, —$NCH_3OH$, —$NCH_3OCH_3$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, $R^3$ is hydrogen, halogen, —OH, —$NH_2$, —SH, substituted or unsubstituted $C_1$-$C_3$ alkyl, or substituted or unsubstituted $C_3$-$C_6$ cycloalkyl. In embodiments, $R^3$ is hydrogen. In embodiments, $R^3$ is halogen. In embodiments, $R^3$ is —F, —Cl, —Br, or —I. In embodiments, $R^3$ is —OH. In embodiments, $R^3$ is —$NH_2$. In embodiments, $R^3$ is —SH. In embodiments, $R^3$ is unsubstituted $C_1$-$C_3$ alkyl. In embodiments, $R^3$ is methyl. In embodiments, $R^3$ is unsubstituted $C_3$-$C_6$ cycloalkyl. In embodiments, $R^3$ is cyclopropyl, cyclobutyl, cycloperthyl, or cyclohexyl.

Each $R^{1A}$, $R^{1B}$, $R^{2A}$, $R^{2B}$, $R^{3A}$, $R^{3B}$, $R^{5A}$, $R^{5A'}$, $R^{5A''}$, $R^{5B}$, $R^{5B'}$, $R^{5B''}$, $R^{6A}$, $R^{6B}$, $R^{8A}$, $R^{8B}$, $R^{10A}$, $R^{10B}$, $R^{12A}$, $R^{12B}$, $R^{14A}$, and $R^{14B}$ are independently hydrogen, —$CX_3$, —$CHX_2$, —$CH_2X$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$), —COOH, —$CONH_2$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_{10}$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered). X is independently —F, —Cl, —Br, or —I.

In embodiments, each $R^{1A}$, $R^{1B}$, $R^{2A}$, $R^{2B}$, $R^{3A}$, $R^{3B}$, $R^{5A}$, $R^{5A'}$, $R^{5A''}$, $R^{5B}$, $R^{5B'}$, $R^{5B''}$, $R^{6A}$, $R^{6B}$, $R^{8A}$, $R^{8B}$, $R^{10A}$, $R^{10B}$, $R^{12A}$, $R^{12B}$, $R^{14A}$, and $R^{14B}$ are independently hydrogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —COOH, —$CONH_2$, substituted (e.g., substituted with a substituent group, a size-limited substituent group, or lower substituent group) or unsubstituted alkyl (e.g., $C_1$-$C_8$, $C_1$-$C_6$, or $C_1$-$C_4$), substituted (e.g., substituted with a substituent group, a size-limited substituent group, or lower substituent group) or unsubstituted heteroalkyl (e.g., 2 to 8 membered, 2 to 6 membered, or 2 to 4 membered), substituted (e.g., substituted with a substituent group, a size-limited substituent group, or lower substituent group) or unsubstituted cycloalkyl (e.g., $C_3$-$C_8$, $C_3$-$C_6$, or $C_5$-$C_6$), substituted (e.g., substituted with a substituent group, a size-limited substituent group, or lower substituent group) or unsubstituted heterocycloalkyl (e.g., 3 to 8 membered, 3 to 6 membered, or 5 to 6 membered), substituted (e.g., substituted with a substituent group, a size-limited substituent group, or lower substituent group) or unsubstituted aryl (e.g., $C_6$-$C_{10}$, $C_{10}$, or phenyl), or substituted (e.g., substituted with a substituent group, a size-limited substituent group, or lower substituent group) or unsubstituted heteroaryl (e.g., 5 to 10 membered, 5 to 9 membered, or 5 to 6 membered).

In embodiments, each $R^{1A}$, $R^{1B}$, $R^{2A}$, $R^{2B}$, $R^{3A}$, $R^{3B}$, $R^{5A}$, $R^{5A'}$, $R^{5A''}$, $R^{5B}$, $R^{5B'}$, $R^{5B''}$, $R^{6A}$, $R^{6B}$, $R^{8A}$, $R^{8B}$, $R^{10}$, $R^{10B}$, $R^{12A}$, $R^{12B}$, $R^{14A}$, and $R^{14B}$ are independently hydrogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —COOH, —$CONH_2$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_6$, or phenyl), or unsubstituted heteroaryl (e.g., 5 to 10 membered, 5 to 9 membered, or 5 to 6 membered).

In embodiments, z is 0, 1 or 2. In embodiments, z is 0. In embodiments, z is 1. In embodiments, z is 2.

In embodiments, n is 0, 1, 2, 3, 4, 5, 6, 7, 8, or 9. In embodiments, n is 0. In embodiments, n is 1. In embodiments, n is 2. In embodiments, n is 3. In embodiments, n is 4. In embodiments, n is 5. In embodiments, n is 6. In embodiments, n is 7. In embodiments, n is 8. In embodiments, n is 9.

$X^1$, $X^2$, $X^3$, $X^5$, $X^{10}$, $X^1_2$, $X^{14}$ and X are independently halogen. In embodiments, $X^1$ is halogen. In embodiments, $X^2$ is halogen. In embodiments, $X^3$ is halogen. In embodiments, $X^5$ is halogen. In embodiments, $X^{10}$ is halogen. In embodiments, $X^1_2$ is halogen. In embodiments, $X^{14}$ is halogen. In embodiments, X is halogen. In embodiments, halogen is —F, —Cl, —Br, —I.

In embodiments, $X^1$ is —F. In embodiments, $X^1$ is —Cl. In embodiments, $X^1$ is —Br. In embodiments, $X^1$ is —I. In embodiments, $X^2$ is —F. In embodiments, $X^2$ is —Cl. In embodiments, $X^2$ is —Br. In embodiments, $X^2$ is —I. In embodiments, $X^3$ is —F. In embodiments, $X^3$ is —Cl. In embodiments, $X^3$ is —Br. In embodiments, $X^3$ is —I. In embodiments, $X^5$ is —F. In embodiments, $X^5$ is —Cl. In embodiments, $X^5$ is —Br. In embodiments, $X^5$ is —I. In embodiments, $X^{10}$ is —F. In embodiments, $X^{10}$ is —Cl. In embodiments, $X^{10}$ is —Br. In embodiments, $X^{10}$ is —I. In embodiments, $X^1_2$ is —F. In embodiments, $X^1_2$ is —Cl. In embodiments, $X^1_2$ is —Br. In embodiments, $X^1_2$ is —I. In embodiments, $X^{14}$ is —F. In embodiments, $X^{14}$ is —Cl. In embodiments, $X^{14}$ is —Br. In embodiments, $X^{14}$ is —I. In embodiments, X is —F. In embodiments, X is —Cl. In embodiments, X is —Br. In embodiments, X is —I.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) or unsubstituted alkyl, substituted (e.g., substituted with a substituent group, a size-limited substituent group, or lower substituent group) or unsubstituted heteroalkyl, substituted (e.g., substituted with a substituent group, a size-limited substituent group, or lower substituent group) or unsubstituted cycloalkyl, substituted (e.g., substituted with a substituent group, a size-limited substituent group, or lower substituent group) or unsubstituted heterocycloalkyl, substituted (e.g., substituted with a substituent group, a size-limited substituent group, or lower substituent group) or unsubstituted aryl, or substituted (e.g., substituted with a substituent group, a size-limited substituent group, or lower substituent group) or unsubstituted heteroaryl.

In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently unsubstituted alkyl, unsubstituted heteroalkyl, unsubstituted cycloalkyl, unsubstituted heterocycloalkyl, unsubstituted aryl, or unsubstituted heteroaryl.

In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) or unsubstituted alkyl. In embodiments, $R^1$, $R^{1A}$, $R^{1B}$, $R^2$, $R^{2A}R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) alkyl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently unsubstituted alkyl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted or unsubstituted alkyl (e.g., $C_1$-$C_8$ alkyl, $C_1$-$C_6$ alkyl, or $C_1$-$C_4$ alkyl). In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted alkyl alkyl (e.g., $C_1$-$C_8$ alkyl, $C_1$-$C_6$ alkyl, or $C_1$-$C_4$ alkyl). In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently unsubstituted alkyl alkyl (e.g., $C_1$-$C_8$ alkyl, $C_1$-$C_6$ alkyl, or $C_1$-$C_4$ alkyl).

In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{11B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) or unsubstituted heteroalkyl. In embodiments, Ru, $R^{1A}$, $R^{1B}R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{2A}$, $R^{12B}$, $R^{14}$, $R^{14A}$, and $R^{14B}$ are independently substituted (e.g., substituted with a substituent group, a size-limited substituent group, or lower substituent group) heteroalkyl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently unsubstituted heteroalkyl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted or unsubstituted heteroalkyl (e.g., 2 to 8 membered, 2 to 6 membered, 4 to 6 membered, 2 to 3 membered, or 4 to 5 membered). In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{2A}$, $R^{12B}$, $R^{14}$, $R^{14A}$, and $R^{14B}$ are independently substituted heteroalkyl (e.g., 2 to 8 membered, 2 to 6 membered, or 2 to 4 membered). In embodiments, Ru, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently an unsubstituted heteroalkyl (e.g., 2 to 8 membered, 2 to 6 membered, or 2 to 4 membered).

In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) or unsubstituted cycloalkyl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) cycloalkyl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently an unsubstituted cycloalkyl. In embodiments, $R^1$, $R^{1A}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted cycloalkyl (e.g., $C_3$-$C_8$ cycloalkyl, $C_3$-$C_6$ cycloalkyl, or $C_5$-$C_6$ cycloalkyl). In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently unsubstituted cycloalkyl (e.g., $C_3$-$C_8$ cycloalkyl, $C_3$-$C_6$ cycloalkyl, or $C_5$-$C_6$ cycloalkyl).

In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) or unsubstituted heterocycloalkyl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) heterocycloalkyl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently an unsubstituted heterocycloalkyl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted or unsubstituted heterocycloalkyl (e.g., 3 to 8 membered, 3 to 6 membered, or 5 to 6 membered). In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted heterocycloalkyl (e.g., 3 to 8 membered, 3 to 6 membered, or 5 to 6 membered). In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently an unsubstituted heterocycloalkyl (e.g., 3 to 8 membered, 3 to 6 membered, or 5 to 6 membered).

In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) or unsubstituted aryl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) aryl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently an unsubstituted aryl. In embodiments, $R^1$, $R^{1A}$, $R^{1B}$, $R^2$, $R^{2A}$, $R^{2B}$, $R^3$, $R^{3A}$, $R^{3B}$ $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted or unsubstituted aryl (e.g., $C_6$-$C_{10}$ aryl, $C_{10}$ aryl, or phenyl). In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted aryl (e.g., $C_6$-$C_{10}$ aryl, $C_{10}$ aryl, or phenyl). In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ 4 are independently an unsubstituted aryl (e.g., $C_6$-$C_{10}$ aryl, $C_{10}$ aryl, or phenyl).

In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) or unsubstituted heteroaryl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted (e.g., substituted with a substituent group, a size-limited substituent group, or lower substituent group) heteroaryl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ 4 are independently an unsubstituted heteroaryl. In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted or unsubstituted heteroaryl (e.g., 5 to 10 membered heteroaryl, 5 to 9 membered heteroaryl, or 5 to 6 membered heteroaryl). In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently substituted heteroaryl (e.g., 5 to 10 membered heteroaryl, 5 to 9 membered heteroaryl, or 5 to 6 membered heteroaryl). In embodiments, $R^1$, $R^{1A}$, $R^{1B}$, $R^2$, $R^{2A}$, $R^{2B}$, $R^3$, $R^{3A}$, $R^{3B}$, $R^5$, $R^{5A}$, $R^{5A'}$, $R^{5A''}$, $R^{5B}$, $R^{5B'}$, $R^{5B''}$, $R^6$, $R^{6A}$, $R^{6B}$, $R^8$, $R^{8A}$, $R^{8B}$, $R^{10}$, $R^{10A}$, $R^{10B}$, $R^{11}$, $R^{12}$, $R^{12A}$, $R^{12B}$, $R^{14}$, $R^{14A}$, and $R^{14B}$ are independently an unsubstituted heteroaryl (e.g., 5 to 10 membered heteroaryl, 5 to 9 membered heteroaryl, or 5 to 6 membered heteroaryl).

In embodiments, the compound is:

69
-continued
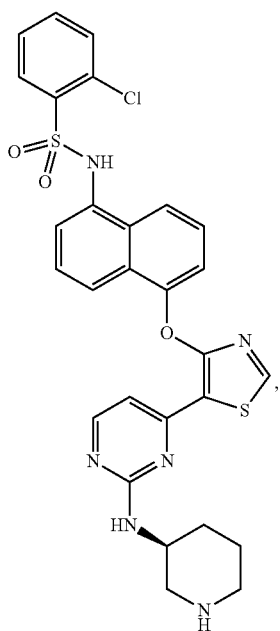
70
-continued
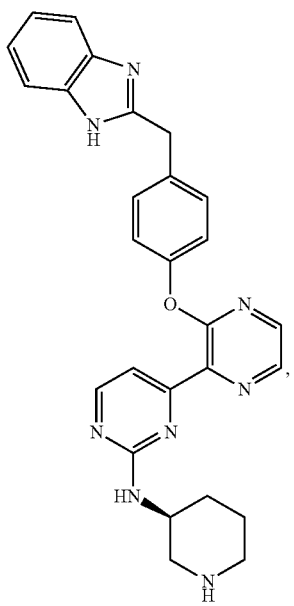
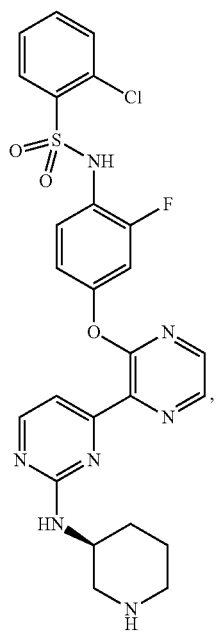
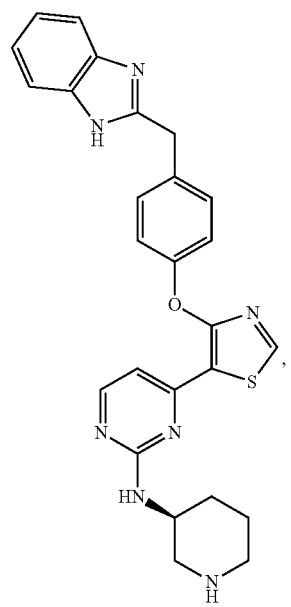

71
-continued
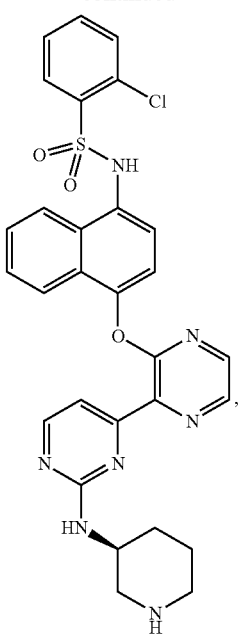
72
-continued
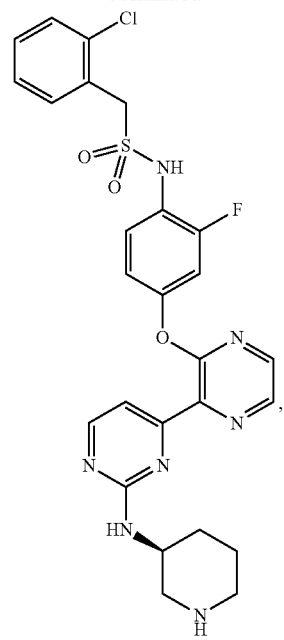
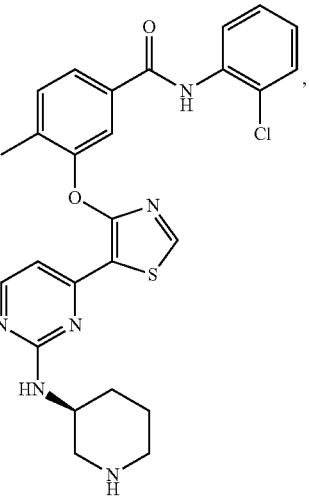
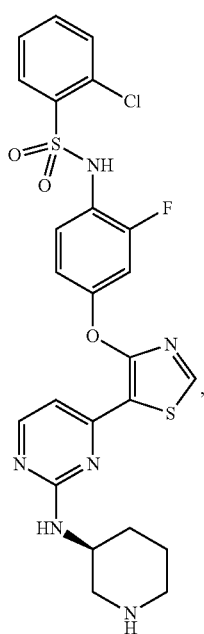
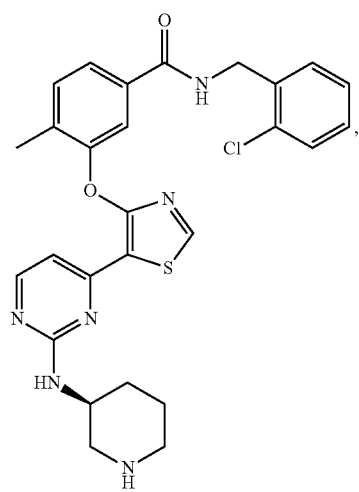

73
-continued
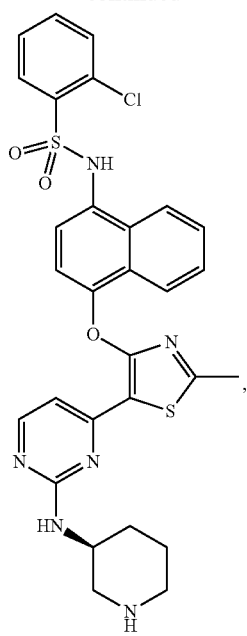
74
-continued
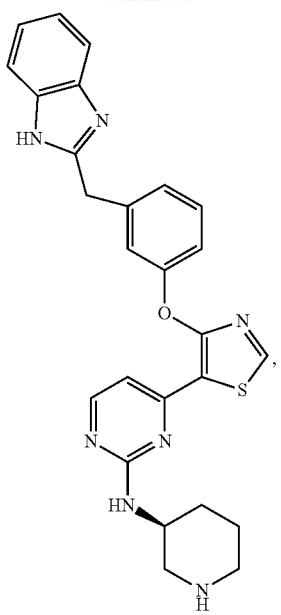
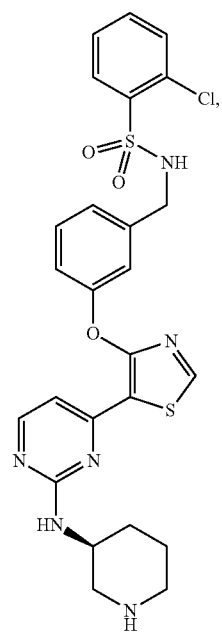
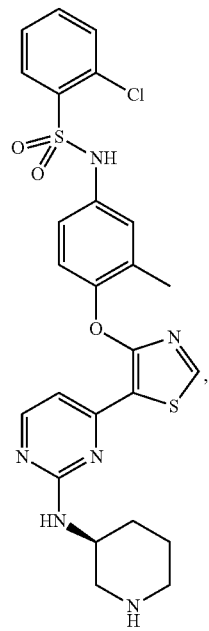

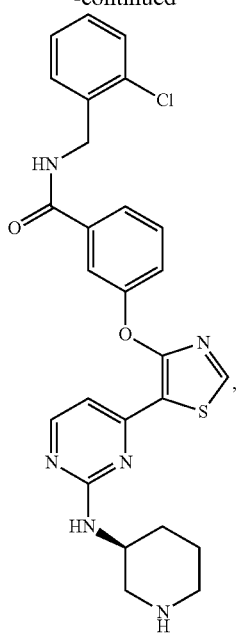,
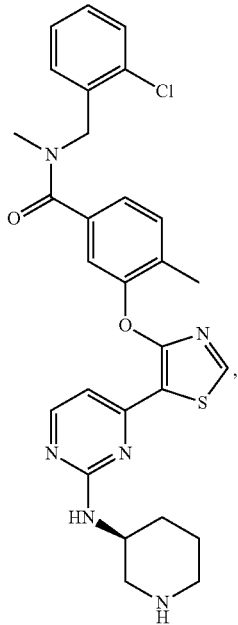,
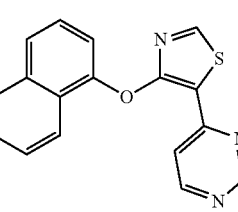
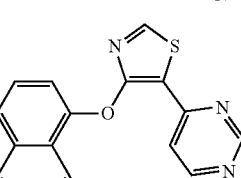, or
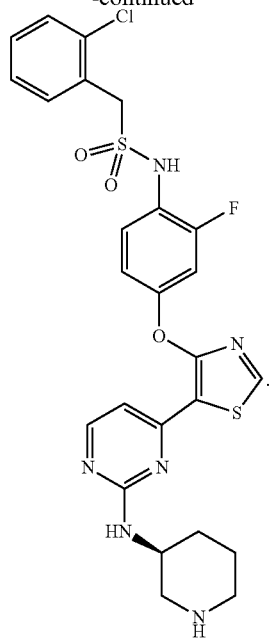.
In embodiments, the compound has the formula:
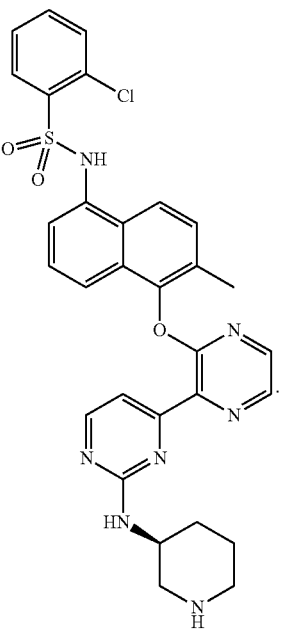 [SMILES: Cc1ccc2c(NS(=O)(=O)c3ccccc3Cl)cccc2c1Oc1nccnc1-c1ccnc(N[C@H]2CCCNC2)n1].

In embodiments, the compound has the formula:
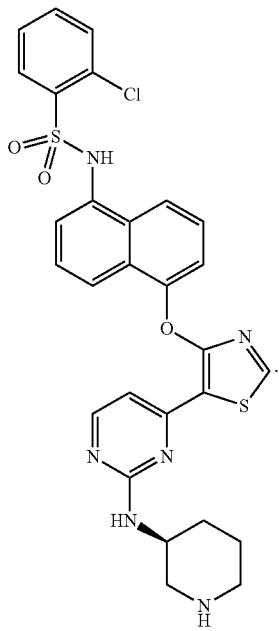 [SMILES: O=S(=O)(Nc1cccc2c(Oc3ncsc3-c3ccnc(N[C@H]4CCCNC4)n3)cccc12)c1ccccc1Cl]
In embodiments, the compound has the formula:
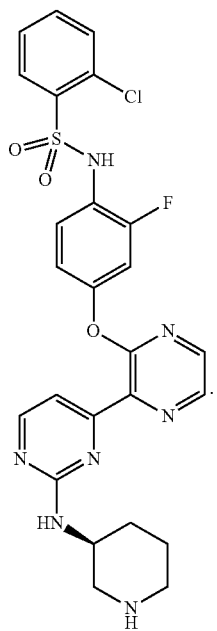 [SMILES: O=S(=O)(Nc1ccc(Oc2nccnc2-c2ccnc(N[C@H]3CCCNC3)n2)cc1F)c1ccccc1Cl]
In embodiments, the compound has the formula:
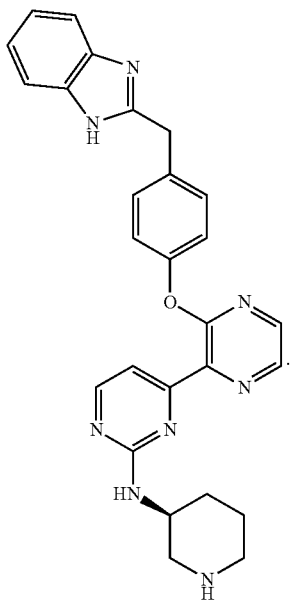 [SMILES: c1ccc2[nH]c(Cc3ccc(Oc4nccnc4-c4ccnc(N[C@H]5CCCNC5)n4)cc3)nc2c1]
In embodiments, the compound has the formula:
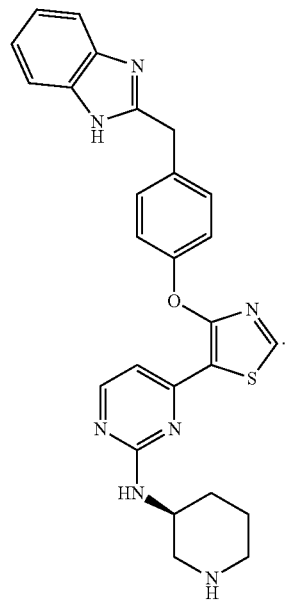 [SMILES: c1ccc2[nH]c(Cc3ccc(Oc4ncsc4-c4ccnc(N[C@H]5CCCNC5)n4)cc3)nc2c1]

In embodiments, the compound has the formula:
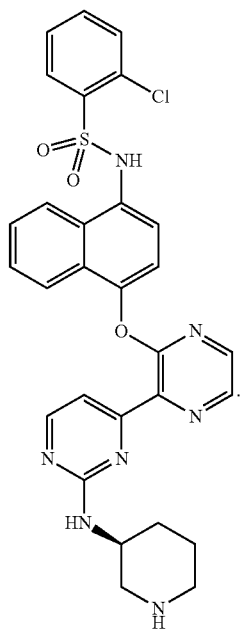 [SMILES: O=S(=O)(Nc1ccc(Oc2nccnc2-c2ccnc(N[C@H]3CCCNC3)n2)c2ccccc12)c1ccccc1Cl]
In embodiments, the compound has the formula:
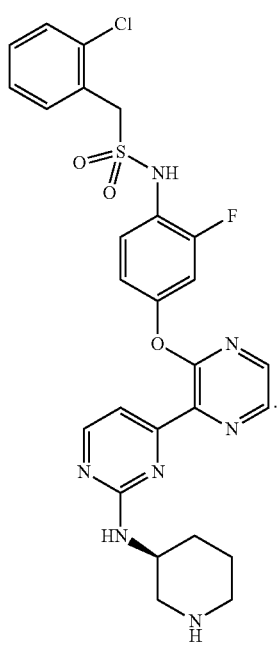
In embodiments, the compound has the formula:
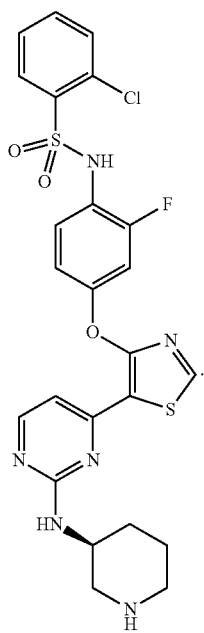 [SMILES: O=S(=O)(Nc1ccc(Oc2ncsc2-c2ccnc(N[C@H]3CCCNC3)n2)cc1F)c1ccccc1Cl]
In embodiments, the compound has the formula:
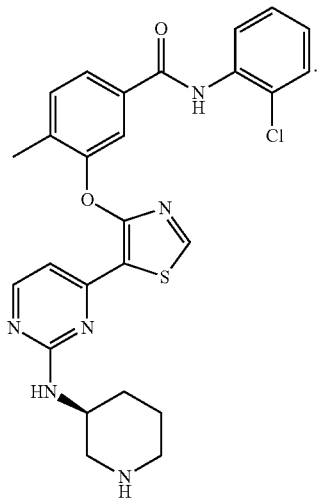 [SMILES: Cc1ccc(C(=O)Nc2ccccc2Cl)cc1Oc1ncsc1-c1ccnc(N[C@H]2CCCNC2)n1]

In embodiments, the compound has the formula:
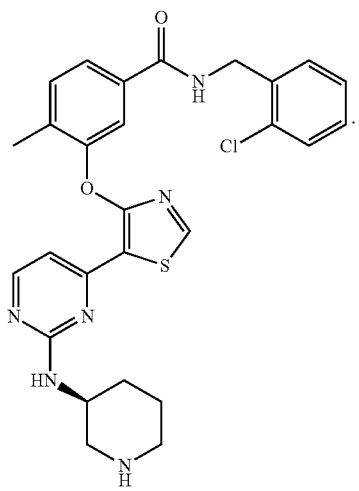 [SMILES: Cc1ccc(C(=O)NCc2ccccc2Cl)cc1Oc1ncsc1-c1ccnc(N[C@H]2CCCNC2)n1]
In embodiments, the compound has the formula:
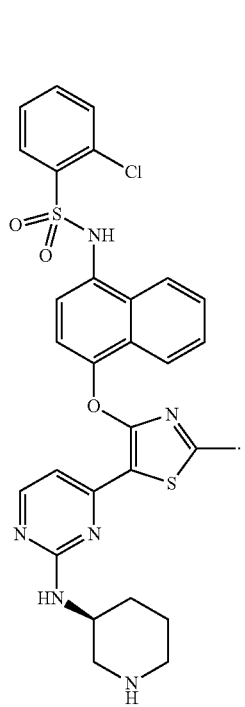
In embodiments, the compound has the formula:
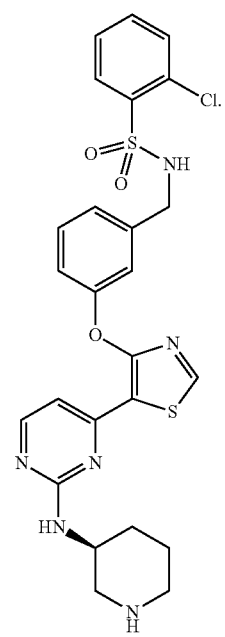 [SMILES: O=S(=O)(NCc1cccc(Oc2ncsc2-c2ccnc(N[C@H]3CCCNC3)n2)c1)c1ccccc1Cl]
In embodiments, the compound has the formula:
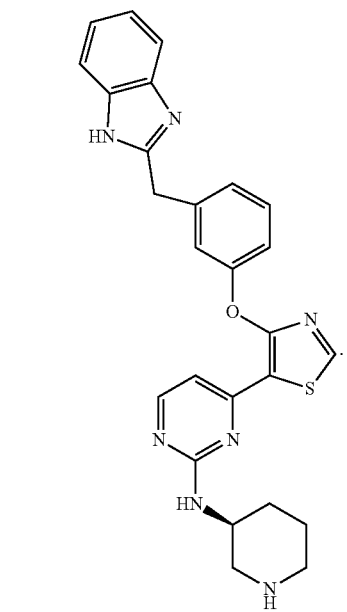 [SMILES: c1cc(Cc2nc3ccccc3[nH]2)cc(Oc2ncsc2-c2ccnc(N[C@H]3CCCNC3)n2)c1]

In embodiments, the compound has the formula:
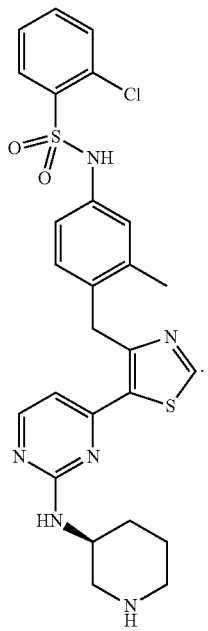 [SMILES: Cc1cc(NS(=O)(=O)c2ccccc2Cl)ccc1Cc1ncsc1-c1ccnc(N[C@H]2CCCNC2)n1]
In embodiments, the compound has the formula:
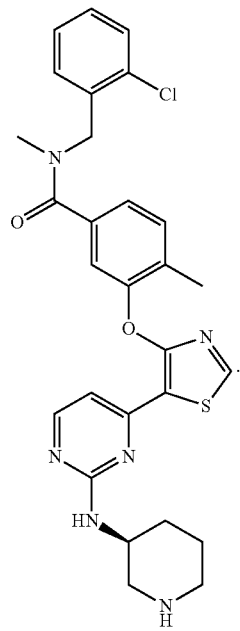
In embodiments, the compound has the formula:
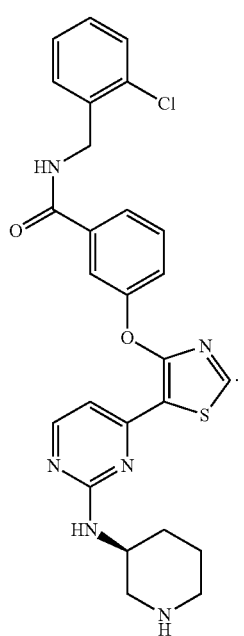 [SMILES: O=C(NCc1ccccc1Cl)c1cccc(Oc2ncsc2-c2ccnc(N[C@H]3CCCNC3)n2)c1]
In embodiments, the compound has the formula:
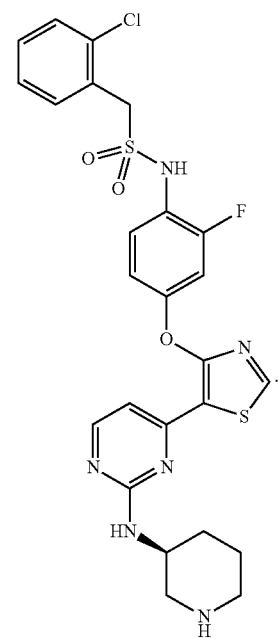 [SMILES: O=S(=O)(Cc1ccccc1Cl)Nc1ccc(Oc2ncsc2-c2ccnc(N[C@H]3CCCNC3)n2)cc1F]

In embodiments, the compound has the formula:

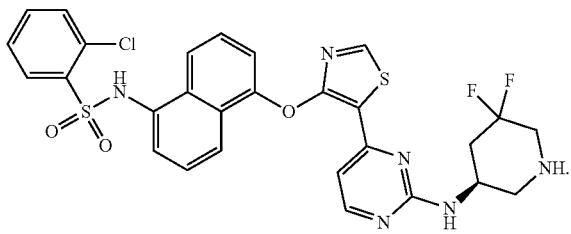 [SMILES: O=S(=O)(Nc1cccc2c(Oc3ncsc3-c3ccnc(N[C@@H]4CNCC(F)(F)C4)n3)cccc12)c1ccccc1Cl]

In embodiments the compound has the formula:

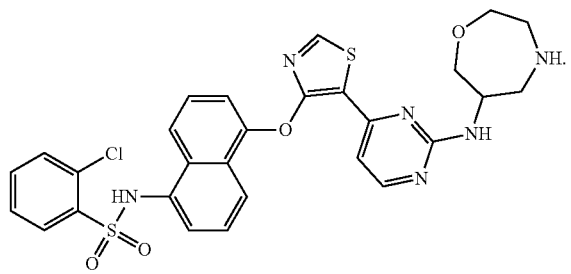 [SMILES: O=S(=O)(Nc1cccc2c(Oc3ncsc3-c3ccnc(NC4CNCCOC4)n3)cccc12)c1ccccc1Cl]

In embodiments, the compound has the formula as described elsewhere herein, for example within a table, claim or example.

III. Pharmaceutical Compositions

In an aspect, there is provided a pharmaceutical composition, including a compound as described herein, including embodiments (e.g., structural Formulae (Ia), (Ib), (IIa), or (IIb)), and a pharmaceutically acceptable excipient.

The compounds as described herein of the present disclosure may be in the form of compositions suitable for administration to a subject. In general, such compositions are "pharmaceutical compositions" comprising a compound (e.g., compounds described herein) and one or more pharmaceutically acceptable or physiologically acceptable excipients (e.g., acceptable diluents or carriers). In certain embodiments, the compounds are present in a therapeutically effective amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein.

The pharmaceutical compositions containing the active ingredient (e.g., an inhibitor of USP7 function, or a compound described herein) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients that are suitable for the manufacture thereof. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation.

Dispersible powders and granules suitable for preparation of an aqueous suspension by the addition of water provide the active ingredient in admixture with a dispersing or wetting agent, and optionally one or more suspending agents and/or preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a compound described herein contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate-buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer; N-(2-Hydroxyethyl)piperazine-N'-(2-ethanesulfonic acid) (HEPES); 2-(N-Morpholino)ethanesulfonic acid (MES); 2-(N-Morpholino)ethanesulfonic acid sodium salt (MES); 3-(N-Morpholino)propanesulfonic acid (MOPS); and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time-delay material such as glyceryl monostearate or glyceryl stearate alone, or in combination with a wax, may be employed. Any drug delivery apparatus may be used to deliver a USP7 inhibitor, including implants (e.g., implantable pumps) and catheter systems, slow injection pumps and devices, all of which are well known to the skilled artisan.

Depot injections, which are generally administered subcutaneously or intramuscularly, may also be utilized to release a compound disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor® EL (BASF, Parsippany, NJ) or phosphate buffered saline (PBS), ethanol, polyol (e.g., glycerol, propylene glycol, and liquid polyethylene glycol), and suitable mixtures thereof. In addition, sterile fixed oils are conventionally employed as a solvent or suspending medium; for this purpose, any bland fixed oil may be employed, including synthetic mono- or diglycerides. Moreover, fatty acids, such as oleic acid, find use in the preparation of injectables. Prolonged absorption of particular injectable formulations can be achieved by including an agent that delays absorption (e.g., aluminum monostearate or gelatin).

The present disclosure contemplates the administration of the compounds described herein in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The compounds described herein contemplated by the present disclosure may be in the form of any other suitable pharmaceutical composition (e.g., sprays for nasal or inhalation use) currently known or developed in the future.

IV. Methods of Use

In another aspect, there is provided a method of treating a inositol-requiring enzyme 1α (IRE1α)-modulated disease or disorder in a subject in need of the treatment, the method including administering an effective amount of a compound described herein, including embodiments (e.g., structural Formulae (Ia), (Ib), (IIa), or (IIb)), or a pharmaceutically acceptable salt thereof. In another aspect, there is provided a method of treating a inositol-requiring enzyme 1β (IRE1β)-modulated disease or disorder in a subject in need of the treatment, the method including administering an effective amount of a compound described herein, including embodiments (e.g., structural Formulae (Ia), (Ib), (IIa), or (IIb)), or a pharmaceutically acceptable salt thereof.

In an aspect, there is provided a method of treating or preventing a IRE1α-mediated disease or disorder, including administering to a patient in need thereof a therapeutically effective amount of a compound or pharmaceutical composition as described herein, including embodiments (e.g., structural Formulae (Ia), (Ib), (IIa), or (IIb)) or a pharmaceutically acceptable salt thereof. In an aspect, there is provided a method of treating or preventing a IRE1β-mediated disease or disorder, including administering to a patient in need thereof a therapeutically effective amount of a compound or pharmaceutical composition as described herein, including embodiments (e.g., structural Formulae (Ia), (Ib), (IIa), or (IIb)) or a pharmaceutically acceptable salt thereof.

In accordance with the present disclosure, a compound (e.g., a compound described herein) or pharmaceutical salt thereof can be used to treat or prevent a proliferative condition or disorder, including a cancer, for example, breast cancer, ovarian cancer, colon adenocarcinoma, lung adenocarcinoma, lung small cell carcinoma, pancreatic adenocarcinoma, pancreatic neutoendocrine tumors, glioblastoma, prostate cancer, hepatocellular carcinoma, myeloma, leukemia, and lymphoma. The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The disclosure contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In some embodiments, the tumor or cancer is breast cancer, ovarian cancer, colon adenocarcinoma, lung adenocarcinoma, lung small cell carcinoma, pancreatic adenocarcinoma, pancreatic neutoendocrine tumors, glioblastoma, prostate cancer, hepatocellular carcinoma, myeloma, leukemia, and lymphoma. The use of the term(s) cancer-related diseases, disorders and conditions is meant to refer broadly to conditions that are associated, directly or indirectly, with cancer, and includes, e.g., angiogenesis and precancerous conditions such as dysplasia. In embodiments, the cancer is breast cancer, ovarian cancer, colon adenocarcinoma, lung adenocarcinoma, lung small cell carcinoma, pancreatic adenocarcinoma, pancreatic neutoendocrine tumors, glioblastoma, prostate cancer, hepatocellular carcinoma, myeloma, leukemia, and lymphoma.

In embodiments, a cancer can be metastatic or at risk of becoming metastatic, or may occur in a diffuse tissue, including cancers of the blood or bone marrow (e.g., leukemia). In some further embodiments, the compounds of the disclosure can be used to overcome T-cell tolerance.

In some embodiments, the present disclosure provides methods for treating a proliferative condition, cancer, tumor, or precancerous condition with a compound described herein and at least one additional therapeutic or diagnostic agent, examples of which are set forth elsewhere herein.

The present disclosure provides methods for treating and/or preventing a proliferative condition, cancer, tumor, or precancerous disease, disorder or condition with a compound described herein.

In embodiments drawn to methods of treating cancer, the administration of a therapeutically effective amount of a compound described herein results in a cancer survival rate greater than the cancer survival rate observed by not administering a therapeutically effective amount of the compound. In further embodiments drawn to methods of treating cancer, the administration of a therapeutically effective amount of a compound described herein results in a reduction of tumor size or a slowing of tumor growth greater than reduction of tumor size or tumor growth observed following lack of administration of a therapeutically effective amount of the compound.

Modulating of IRE1α or IRE1β activity may also represent an important strategy for the treatment or prevention of neurological, neuropsychiatric, neurodegenerative or other diseases, disorders and conditions having some association with the central nervous system, including disorders associated with impairment of cognitive function and/or motor function. Many of these diseases, disorders and conditions include an immune and/or inflammatory component. In embodiments, the disease or disorder is Parkinson's disease, dementia, Alzheimer's disease, lateral sclerosis, prion disorders, multiple sclerosis, Guillan-Barre syndrome, adrenoleukodystrophy, adrenomyeloneuropathy, optic neuritis, transverse myelitis, primary peripheral neuropathy, such as Charcot-Marie Tooth (CMT), and secondary peripheral neuropathy, such as diabetes mellitus (DM).

Embodiments of the present disclosure contemplate the administration of the compounds described herein to a subject for the treatment or prevention of any other disorder that may benefit from at least some level of IRE1α or IRE1β modulation. Such diseases, disorders and conditions may include, for example, fibrotic disorders (idiopathic pulmonary fibrosis, familial pulmonary fibrosis, scleroderma), dermatologic disorders (psoriasis), rheumatologic/autoimmune disorders (rheumatoid arthritis, Grave's disease, Hashimoto's disease, Addison's disease, lupus, ankylosing spondylitis, sarcoidosis), general gastro-intestinal tract inflammation (Inflammatory Bowel Disease (IBD), Crohn's disease, colitis), and chronic inflammatory lung disease (bronchial asthma, chronic obstructive pulmonary disease (COPD), bronchiectasis, and cystic fibrosis (CF).

In embodiments, the disease or disorder includes metabolic (e.g., development of insulititis diabetes), hepatic (e.g., hepatic fibrosis, NASH, and NAFLD), ophthalmologic (e.g., diabetic retinopathy), or renal (e.g., renal failure) disorders.

In embodiments, IRE1α-mediated disease or disorder is cancer, fibrotic disease or disorder, neurodegenerative disease or disorder, demyelinating disease or disorder, dermatologic disease or disorder, rheumatologic/autoimmune disease or disorder, peripheral neuropathy, general gastro-intestinal tract inflammation, chronic inflammatory lung disease, posterior eye indication, or diabetes mellitus. In embodiments, IRE1α-mediated disease or disorder is fibrotic disease or disorder. In embodiments, IRE1α-mediated disease or disorder is neurodegenerative disease or disorder. In embodiments, IRE1α-mediated disease or disorder is demyelinating disease or disorder. In embodiments, IRE1α-mediated disease or disorder is dermatologic disease or disorder. In embodiments, IRE1α-mediated disease or disorder is rheumatologic/autoimmune disease or disorder. In embodiments, IRE1α-mediated disease or disorder is peripheral neuropathy. In embodiments, IRE1α-mediated disease or disorder is general gastro-intestinal tract inflammation. In embodiments, IRE1α-mediated disease or disorder is chronic inflammatory lung disease. In embodiments, IRE1α-mediated disease or disorder is posterior eye indication. In embodiments, IRE1α-mediated disease or disorder is diabetes mellitus. In embodiments, IRE1β-mediated disease or disorder is cancer, fibrotic disease or disorder, neurodegenerative disease or disorder, demyelinating disease or disorder, dermatologic disease or disorder, rheumatologic/autoimmune disease or disorder, peripheral neuropathy, general gastro-intestinal tract inflammation, chronic inflammatory lung disease, posterior eye indication, or diabetes mellitus. In embodiments, IRE1β-mediated disease or disorder is fibrotic disease or disorder. In embodiments, IRE1β-mediated disease or disorder is neurodegenerative disease or disorder. In embodiments, IRE1β-mediated disease or disorder is demyelinating disease or disorder. In embodiments, IRE1β-mediated disease or disorder is dermatologic disease or disorder. In embodiments, IRE1β-mediated disease or disorder is rheumatologic/autoimmune disease or disorder. In embodiments, IRE1β-mediated disease or disorder is peripheral neuropathy. In embodiments, IRE1β-mediated disease or disorder is general gastro-intestinal tract inflammation. In embodiments, IRE1β-mediated disease or disorder is chronic inflammatory lung disease. In embodiments, IRE1β-mediated disease or disorder is posterior eye indication. In embodiments, IRE1β-mediated disease or disorder is diabetes mellitus.

In embodiments, the IRE1α-mediated disease or disorder is cancer. In embodiments, the IRE1β-mediated disease or disorder is cancer. In certain embodiments, cancer includes, but is not limited to, breast cancer, ovarian cancer, colon adenocarcinoma, lung adenocarcinoma, lung small cell carcinoma, pancreatic adenocarcinoma, pancreatic neutoendocrine tumors, glioblastoma, prostate cancer, hepatocellular carcinoma, myeloma, leukemia, and lymphoma.

In embodiments, a method of treating a IRE1α-mediated cancer comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof. In embodiments, a method of treating a IRE1β-mediated cancer comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof.

In embodiments, a method of treating a IRE1α-mediated cancer by administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof, further includes administering to the patient a chemotherapeutic agent in combination with the compound as described herein. In embodiments, a method of treating a IRE1β-mediated cancer by administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof, further includes administering to the patient a chemotherapeutic agent in combination with the compound as described herein.

In embodiments, the IRE1α-mediated disease or disorder is fibritoc disease or disorder. In embodiments, the IRE1β-mediated disease or disorder is fibritoc disease or disorder. In certain embodiments, fibritoc disease or disorder includes, but is not limited to, idiopathic pulmonary fibrosis (IPF), familial pulmomatu fibrosis (FPF), scleroderma (systemic sclerosis), renal fibrosis, and hepatic fibrosis.

In embodiments, a method of treating a IRE1α-mediated fibritoc disease or disorder comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof. In embodiments, a method of treating a IRE1β-mediated fibritoc disease or disorder comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof.

In embodiments, the IRE1α-mediated disease or disorder is neurodegenerative disease or disorder. In embodiments, the IRE1β-mediated disease or disorder is neurodegenerative disease or disorder. In certain embodiments, neurodegenerative disease or disorder includes, but is not limited to, amyotrophic lateral sclerosis (ALS), Parkinson's disease, Alzheimer's disease, prion disorders (e.g., bovine spongiform encephalopathy (BSE)), and frontotemporal dementia.

In embodiments, a method of treating a IRE1α-mediated neurodegenerative disease or disorder comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof. In embodiments, a method of treating a IRE1β-mediated neurodegenerative disease or disorder comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof.

In embodiments, the IRE1α-mediated disease or disorder is demyelinating disease or disorder. In embodiments, the IRE1β-mediated disease or disorder is demyelinating disease or disorder. In certain embodiments, demyelinating disease or disorder includes, but is not limited to, multiple sclerosis (MS), Guillan-Barre syndrome, adrenoleukodystrophy, adrenomyeloneuropathy, optic neuritis, and transverse myelitis.

In embodiments, a method of treating a IRE1α-mediated demyelinating disease or disorder comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof. In embodiments, a method of treating a IRE1β-mediated demyelinating disease or disorder comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof.

In embodiments, the IRE1α-mediated disease or disorder is dermatologic disease or disorder. In embodiments, the IRE1β-mediated disease or disorder is dermatologic disease or disorder. In certain embodiments, dermatologic disease or disorder includes, but is not limited to, psoriasis.

In embodiments, a method of treating a IRE1α-mediated dermatologic disease or disorder comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof. In embodiments, a method of treating a IRE1β-mediated dermatologic disease or disorder comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof.

In embodiments, the IRE1α-mediated disease or disorder is rheumatologic/autoimmune disease or disorder. In embodiments, the IRE1β-mediated disease or disorder is rheumatologic/autoimmune disease or disorder. In certain embodiments, rheumatologic/autoimmune disease or disorder includes, but is not limited to, rheumatoid arthritis, Grave's disease, Hashimoto's disease, Addison's disease, lupus, ankylosing spondylitis, and sarcoidosis.

In embodiments, a method of treating a IRE1α-mediated rheumatologic/autoimmune disease or disorder comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof. In embodiments, a method of treating a IRE1β-mediated rheumatologic/autoimmune disease or disorder comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof.

In embodiments, the IRE1α-mediated disease or disorder is peripheral neuropathy. In embodiments, the IRE1β-mediated disease or disorder is peripheral neuropathy. In certain embodiments, peripheral neuropathy includes, but is not limited to, primary peripheral neuropathy, such as Charcot-Marie Tooth (CMT), and secondary peripheral neuropathy, such as diabetes mellitus (DM).

In embodiments, a method of treating a IRE1α-mediated peripheral neuropathy comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof. In embodiments, a method of treating a IRE1β-mediated peripheral neuropathy comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof.

In embodiments, the IRE1α-mediated disease or disorder is general gastro-intestinal tract inflammation. In embodiments, the IRE1β-mediated disease or disorder is general gastro-intestinal tract inflammation. In certain embodiments, general gastro-intestinal tract inflammation includes, but is not limited to, Inflammatory Bowel Disease (IBD), Crohn's disease, and colitis.

In embodiments, a method of treating a IRE1α-mediated general gastro-intestinal tract inflammation comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof. In embodiments, a method of treating a IRE1β-mediated general gastro-intestinal tract inflammation comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof.

In embodiments, the IRE1α-mediated disease or disorder is chronic inflammatory lung disease. In embodiments, the IRE1β-mediated disease or disorder is chronic inflammatory lung disease. In certain embodiments, chronic inflammatory lung disease includes, but is not limited to, bronchial asthma, chronic obstructive pulmonary disease (COPD), bronchiectasis, and cystic fibrosis (CF).

In embodiments, a method of treating a IRE1α-mediated chronic inflammatory lung disease comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof. In embodiments, a method of treating a IRE1β-mediated chronic inflammatory lung disease comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof.

In embodiments, the IRE1α-mediated disease or disorder is diabetes mellitus. In embodiments, the IRE1β-mediated disease or disorder is diabetes mellitus. In certain embodiments, diabetes mellitus includes, but is not limited to, type 1 (autoimmune), type 2 (obesity-induced/insulin-resistant), monogenic (MODY syndromes), Wolcott Rallisson syndrome, and Wolfram syndrome.

In embodiments, a method of treating a IRE1α-mediated diabetes mellitus comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof. In embodiments, a method of treating a IRE1β-mediated diabetes mellitus comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof.

In embodiments, the IRE1α-mediated disease or disorder is posterior and anterior eye indication. In embodiments, the IRE1β-mediated disease or disorder is posterior and anterior eye indication. In certain embodiments, posterior eye indication includes, but is not limited to, retinal degeneration, Stargardt's disease, wet age-related macular degeneration (AMD), and dry AMD. In certain embodiments, anterior eye indication includes, but is not limited to, glaucoma and Fuch's dystrophy.

In embodiments, a method of treating a IRE1α-mediated posterior and anterior eye indication comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof. In embodiments, a method of treating a IRE1β-mediated posterior and anterior eye indication comprises administering to a patient in need thereof a therapeutically effective amount of a compound or pharmaceutical composition as described herein, including embodiments (e.g., structural Formulae (Ia), (Ib), (IIa), or (IIb)), or a pharmaceutically acceptable salt thereof.

The present disclosure contemplates the administration of the compounds described herein, and compositions (e.g., pharmaceutical salts, pharmaceutical composition) thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the compounds disclosed herein over a defined period of time. In embodiments, the administration is oral administration. In embodiments, the administration parenteral administration.

The compounds of the present disclosure may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of the compounds of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In embodiments, the compounds contemplated by the present disclosure may be administered (e.g., orally) at dosage levels of about 0.01 mg/kg to about 50 mg/kg, or about 1 mg/kg to about 25 mg/kg, of subject body weight per day, one, two, three, four or more times a day, to obtain the desired therapeutic effect. For administration of an oral agent, the compositions can be provided in the form of tablets, capsules and the like containing from 0.05 to 1000 milligrams of the active ingredient, particularly 0.05, 0.1, 0.25, 0.5, 0.75, 1.0, 1.25, 1.5, 1.75, 2.0, 2.5, 5.0, 7.5, 10.0, 15.0, 20.0, 25.0, 50.0, 75.0, 100.0, 125.0, 150.0, 175.0, 200.0, 250.0, 300.0, 400.0, 500.0, 600.0, 750.0, 800.0, 900.0, and 1000.0 milligrams of the active ingredient. A pharmaceutically acceptable carrier(s), diluent(s) and/or excipient(s) may be present in an amount of from about 0.1 g to about 2.0 g.

In embodiments, the dosage of the desired compound is contained in a "unit dosage form". The phrase "unit dosage form" refers to physically discrete units, each unit including a predetermined amount of a compound (e.g., a compound described herein), sufficient to produce the desired effect. It will be appreciated that the parameters of a unit dosage form will depend on the particular agent and the effect to be achieved.

V. Kits

In another aspect, provided herein is a kit including a compound described herein or pharmaceutical compositions thereof. The kits are generally in the form of a physical structure housing various components, as described below, and may be utilized, for example, in practicing the methods described above.

A kit may include one or more of the compounds disclosed herein (e.g., provided in a sterile container), which may be in the form of a pharmaceutical composition suitable for administration to a subject. In embodiments, the compound has the structure of Formulae (Ia), (Ib), (IIa), or (IIb)), or a pharmaceutically acceptable salt thereof. The compounds described herein can be provided in a form that is ready for use (e.g., a tablet or capsule) or in a form requiring, for example, reconstitution or dilution (e.g., a powder) prior to administration. When the compound is in a form that needs to be reconstituted or diluted by a user, the kit may also include diluents (e.g., sterile water), buffers, pharmaceutically acceptable excipients, and the like, packaged with, or separately from, the compound. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EMBODIMENTS

Embodiment 1. A compound of structural formula (Ia) or (Ib) or a pharmaceutically acceptable salt thereof:

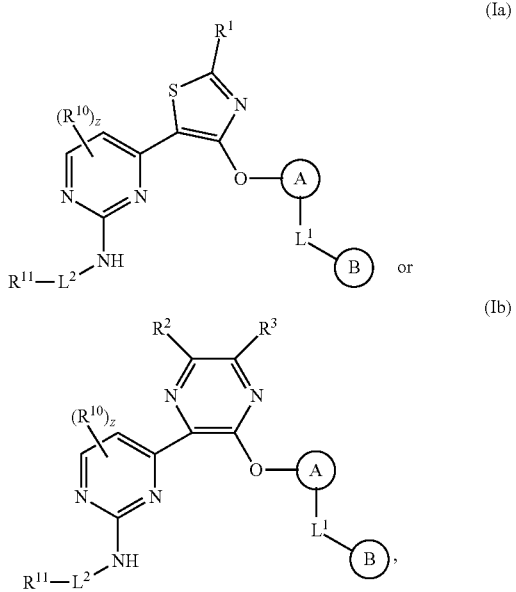

wherein:
- $L^1$ is a bond, —O—, —S—, —SO—, —S(O)$_2$—, —NR$^{12}$—, —C(O)—, —C(O)NR$^{12}$—, —C(O)O—, —S(O)$_2$NR$^{12}$—, —NR$^{12}$C(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
- $L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
- ring A is a substituted or unsubstituted aryl or substituted or unsubstituted heteroaryl;
- ring B is a substituted or unsubstituted cycloalkyl, substituted or unsubstituted heterocycloalkyl, substituted or unsubstituted aryl or substituted or unsubstituted heteroaryl;
- $R^1$ is hydrogen, halogen, —CX$^1_3$, —CHX$^1_2$, —CH$_2$X$^1$, —OCX$^1_3$, —OCHX$^1_2$, —OCH$_2$X$^1$, —CN, —S(O)$_2$R$^{1A}$, —SR$^{1A}$, —S(O)R$^{1A}$, —SO$_2$NR$^{1A}$R$^{1B}$, —NHC(O)NR$^{1A}$R$^{1B}$, —N(O)$_2$, —NR$^{1A}$R$^{1B}$, —NHNR$^{1A}$R$^{1B}$, —C(O)R$^{1A}$, —C(O)—OR$^{1A}$, —C(O)NR$^{1A}$R$^{1B}$, —C(O)NHNR$^{1A}$R$^{1B}$, —OR$^{1A}$, —NR$^{1A}$SO$_2$R$^{1B}$, —NR$^{1A}$C(O)R$^{1B}$, —NR$^{1A}$C(O)OR$^{1B}$, —NR$^{1A}$OR$^{1B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^2$ is hydrogen, halogen, —CX$^2_3$, —CHX$^2_2$, —CH$_2$X$^2$, —OCX$^2_3$, —OCHX$^2_2$, —OCH$_2$X$^2$, —CN, —S(O)$_2$R$^{2A}$, —SR$^{2A}$, —S(O)R$^{2A}$, —SO$_2$NR$^{2A}$R$^{2B}$, —NHC(O)NR$^{2A}$R$^{2B}$, —N(O)$_2$, —NR$^{2A}$R$^{2B}$, —NHNR$^{2A}$R$^{2B}$, —C(O)R$^{2A}$, —C(O)—OR$^{2A}$, —C(O)NR$^{2A}$R$^{2B}$, —C(O)NHNR$^{2A}$R$^{2B}$, —OR$^{2A}$, —NR$^{2A}$SO$_2$R$^{2B}$, —NR$^{2A}$C(O)R$^{2B}$, —NR$^{2A}$C(O)OR$^{2B}$, —NR$^{2A}$OR$^{2B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^3$ is hydrogen, halogen, —CX$^3_3$, —CHX$^3_2$, —CH$_2$X$^3$, —OCX$^3_3$, —OCHX$^3_2$, —OCH$_2$X$^3$, —CN, —S(O)$_2$R$^{3A}$, —SR$^{3A}$, —S(O)R$^{3A}$, —SO$_2$NR$^{3A}$R$^{3B}$, —NHC(O)NR$^{3A}$R$^{3B}$, —N(O)$_2$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —C(O)NHNR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{10}$ is —CX$^{10}_3$, —CHX$^{10}_2$, —CH$_2$X$^{10}$, —OCX$^{10}_3$, —OCHX$^{10}_2$, —OCH$_2$X$^{10}$, —S(O)$_2$R$^{10A}$, —SR$^{10A}$, —S(O)R$^{10A}$, —SO$_2$NR$^{10A}$R$^{10B}$, —NHC(O)NR$^{10A}$R$^{10B}$, —NR$^{10A}$R$^{10B}$, —NHNR$^{10A}$R$^{10B}$, —C(O)R$^{10A}$, —C(O)—OR$^{10A}$, —C(O)NR$^{10A}$R$^{10B}$, —C(O)NHNR$^{10A}$R$^{10B}$, —OR$^{10A}$, —NR$^{10A}$SO$_2$R$^{10B}$, —NR$^{10A}$C(O)R$^{10B}$, —NR$^{10A}$C(O)OR$^{10B}$, —NR$^{10A}$OR$^{10B}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{11}$ is —N(R$^{14}$)$_2$ or a substituted or unsubstituted nitrogen-containing heterocycloalkyl;
- $R^{12}$ is hydrogen, —CX$^{12}_3$, —CHX$^{12}_2$, —CH$_2$X$^{12}$, —OCX$^{12}_3$, —OCHX$^{12}_2$, —OCH$_2$X$^{12}$, —S(O)$_2$R$^{12A}$, —SR$^{12A}$, —S(O)R$^{12A}$, —SO$_2$NR$^{12A}$R$^{12B}$, —NHC(O)NR$^{12A}$R$^{12B}$, —NR$^{12A}$R$^{12B}$, —NHNR$^{12A}$R$^{12B}$, —C(O)R$^{12A}$, —C(O)—OR$^{12A}$, —C(O)NR$^{12A}$R$^{12B}$, —C(O)NHNR$^{12A}$R$^{12B}$, —OR$^{12A}$, —NR$^{12A}$SO$_2$R$^{12B}$, —NR$^{12A}$C(O)R$^{12B}$, —NR$^{12A}$C(O)OR$^{12B}$, —NR$^{12A}$OR$^{12B}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{14}$ is hydrogen, —CX$^{14}_3$, —CHX$^{14}_2$, —CH$_2$X$^{14}$, —OCX$^{14}_3$, —OCHX$^{14}_2$, —OCH$_2$X$^{14}$, —S(O)$_2$R$^{14A}$, —SR$^{14A}$, —S(O)R$^{14A}$, —SO$_2$NR$^{14A}$R$^{14B}$, —NHC(O)NR$^{14A}$R$^{14B}$, —NR$^{14A}$R$^{14B}$, —NHNR$^{14A}$R$^{14B}$, —C(O)R$^{14A}$, —C(O)—OR$^{14A}$, —C(O)NR$^{14A}$R$^{14B}$, —C(O)NHNR$^{14A}$R$^{14B}$, —OR$^{14A}$, —NR$^{14A}$SO$_2$R$^{14B}$, —NR$^{14A}$C(O)R$^{14B}$, —NR$^{14A}$C(O)OR$^{14B}$, —NR$^{14A}$OR$^{14B}$ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{1A}$, $R^{1B}$, $R^{2A}$, $R^{2B}$, $R^{3A}$, $R^{3B}$, $R^{10A}$, $R^{10B}$, $R^{12A}$, $R^{12B}$, $R^{14A}$, and $R^{14B}$ are independently hydrogen, —CX$_3$, —CHX$_2$, —CH$_2$X, —C(O)OH, —C(O)NH$_2$, —OH, —NH$_2$, —COOH, —CONH$_2$, —SH, —SO$_3$H, —SO$_4$H, —SO$_2$NH$_2$, —NHNH$_2$, —ONH$_2$, —NHC═

(O)NHNH₂, —NHC═(O)NH₂, —NHSO₂H, —NHC═(O)H, —NHC(O)OH, —NHOH, —OCX₃, —OCHX₂, —OCH₂X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{10A}$ and $R^{10B}$ substituents bonded to the same nitrogen atom may optionally be joined to form a substituted or unsubstituted heterocycloalkyl or substituted or unsubstituted heteroaryl; $R^{12A}$ and $R^{12B}$ substituents bonded to the same nitrogen atom may optionally be joined to form a substituted or unsubstituted heterocycloalkyl or substituted or unsubstituted heteroaryl; and $R^{14A}$ and $R^{14B}$ substituents bonded to the same nitrogen atom may optionally be joined to form a substituted or unsubstituted heterocycloalkyl or substituted or unsubstituted heteroaryl;

X, $X^1$, $X^2$, $X^3$, $X^{10}$, $X^1{}_2$, and $X^{14}$ are independently halogen; and z is 0, 1 or 2.

Embodiment 2. The compound of embodiment 1, wherein $L^1$ is -$L^{1A}$-$L^{1B}$-$L^{1C}$-, wherein $L^{1A}$ and $L^{1C}$ are independently a bond or a substituted or unsubstituted alkylene.

Embodiment 3. The compound of embodiment 2, wherein $L^{1A}$ and $L^{1C}$ are a bond.

Embodiment 4. The compound of embodiments 1 or 2, wherein $L^{1A}$ and $L^{1C}$ are independently a substituted or unsubstituted alkylene.

Embodiment 5. The compound of any one of embodiments 1 to 4, wherein $L^{1A}$ and $L^{1C}$ are independently a substituted or unsubstituted methylene or substituted or unsubstituted ethylene.

Embodiment 6. The compound of any one of embodiments 1 to 5, wherein $L^{1B}$ is —O—, —S—, —SO—, —S(O)₂—, —NR¹²—, —C(O)—, —C(O)NR¹²—, —C(O)O—, —S(O)₂NR¹²—, or —NR¹²C(O)O—.

Embodiment 7. The compound of any one of embodiments 1 to 6, wherein -$L^{1A}$-$L^{1B}$-$L^{1C}$- is —C(O)N(CH₃)CH₂—, —C(O)NHCH₂—, —C(O)NH—, —NHSO₂—, —NHSO₂CH₂—, or —CH₂NHSO₂—.

Embodiment 8. The compound of any one of embodiments 1 to 7, wherein $R^{11}$ is a 3 to 7 membered substituted or unsubstituted nitrogen-containing heterocycloalkyl.

Embodiment 9. The compound of any one of embodiments 1 to 8, wherein $R^{11}$ is a 5 to 6 membered substituted or unsubstituted nitrogen-containing heterocycloalkyl.

Embodiment 10. The compound of any one of embodiments 1 to 9, wherein $R^{11}$ is a substituted or unsubstituted 1-piperidinyl, substituted or unsubstituted 2-piperidinyl, substituted or unsubstituted 3-piperidinyl, substituted or unsubstituted 4-piperidinyl, substituted or unsubstituted 5-piperidinyl, substituted or unsubstituted 1,4-oxazepanyl, substituted or unsubstituted 1,3-oxazepanyl, substituted or unsubstituted 1,2-oxazepanyl, substituted or unsubstituted piperazinyl, substituted or unsubstituted pyrrolidinyl, substituted or unsubstituted azetidinyl, substituted or unsubstituted aziridinyl, substituted or unsubstituted morpholinyl, substituted or unsubstituted 3,6-dihydro-2H-1-pyridinyl, substituted or unsubstituted pyridinyl, substituted or unsubstituted pyrazinyl, substituted or unsubstituted pyrimidinyl, substituted or unsubstituted pyridazinyl, or substituted or unsubstituted triazinyl.

Embodiment 11. The compound of any one of embodiments 1 to 10, wherein the compound has the structural formula (IIa) or (IIb):

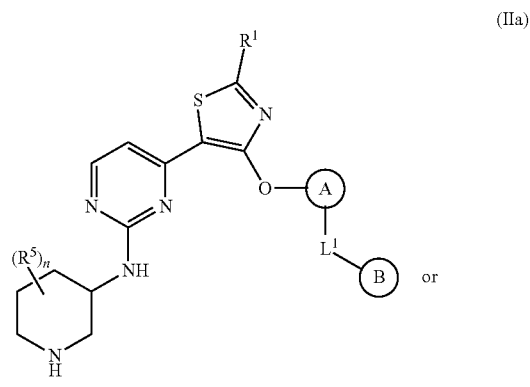

(IIa)

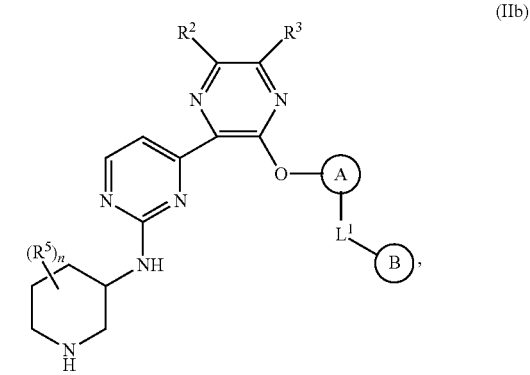

(IIb)

wherein:

$R^5$ is independently halogen, —CX⁵₃, —CHX⁵, —CH₂X⁵, —OCX⁵₃, —OCHX⁵₂, —OCH₂X⁵, —CN, —S(O)₂R⁵ᴬ, —SR⁵ᴬ, —S(O)R⁵ᴬ, —SO₂NR⁵ᴬR⁵ᴮ, —NHC(O)NR⁵ᴬR⁵ᴮ, —N(O)₂, —NR⁵ᴬR⁵ᴮ, —NHNR⁵ᴬR⁵ᴮ, —C(O)R⁵ᴬ, —C(O)—OR⁵ᴬ, —C(O)NR⁵ᴬR⁵ᴮ, —C(O)NHNR⁵ᴬR⁵ᴮ, —OR⁵ᴬ, —NR⁵ᴬSO₂R⁵ᴮ, —NR⁵ᴬC(O)R⁵ᴮ, —NR⁵ᴬC(O)OR⁵ᴮ, —NR⁵ᴬOR⁵ᴮ, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{5A}$ and $R^{5B}$ are independently —CX⁵₃, —CHX⁵₂, —CH₂X⁵, —C(O)OH, —C(O)NH₂, —OH, —NH₂, —COOH, —CONH₂, —SH, —SO₃H, —SO₄H, —SO₂NH₂, —NHNH₂, —ONH₂, —NHC═(O)NHNH₂, —NHC═(O)NH₂, —NHSO₂H, —NHC═(O)H, —NHC(O)OH, —NHOH, —OCX⁵₃, —OCHX⁵₂, —OCH₂X⁵, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl;

$X^5$ is halogen; and n is an integer from 0 to 9.

Embodiment 12. The compound of any one of embodiments 1 to 11, wherein n is an integer from 0 to 2.

Embodiment 13. The compound of any one of embodiments 1 to 12, wherein ring B is $R^6$-substituted or unsubstituted 3 to 6 membered heterocycloalkyl, $R^6$-substituted or unsubstituted $C_6$-$C_{10}$ aryl, or $R^6$-substituted or unsubstituted 5 to 6 membered heteroaryl;

$R^6$ is halogen, —$CF_3$, —$CCl_3$, —$CBr_3$, —$CI_3$—OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{6A}$-substituted or unsubstituted $C_1$-$C_6$ alkyl, $R^{6A}$-substituted or unsubstituted 2 to 6 membered heteroalkyl, $R^{6A}$-substituted or unsubstituted $C_3$-$C_6$ cycloalkyl, $R^{6A}$-substituted or unsubstituted 3 to 6 membered heterocycloalkyl, $R^{6A}$-substituted or unsubstituted $C_6$-$C_{10}$ aryl, or $R^{6A}$-substituted or unsubstituted 5 to 6 membered heteroaryl; and $R^{6A}$ is halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$-$C_{10}$ aryl, or unsubstituted 5 to 6 membered heteroaryl.

Embodiment 14. The compound of any one of embodiments 1 to 13, wherein:

ring B is $R^6$-substituted or unsubstituted phenyl or $R^6$-substituted or unsubstituted benzimidazole; and $R^6$ is hydrogen.

Embodiment 15. The compound of any one of embodiments 1 to 14, wherein:

ring A is $R^8$-substituted or unsubstituted $C_6$-$C_{10}$ aryl;

$R^8$ is halogen, —$CF_3$, —$CCl_3$, —$CBr_3$, —$CI_3$, —OH, —$NH_2$, —COOH, —$CONH_2$, —$NO_2$, —$N_3$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$OCH_2F$, —$OCH_2Cl$, —$OCH_2Br$, —$OCH_2I$, $R^{8A}$-substituted or unsubstituted $C_1$-$C_6$ alkyl, $R^{8A}$-substituted or unsubstituted 2 to 6 membered heteroalkyl, $R^{8A}$-substituted or unsubstituted $C_3$-$C_6$ cycloalkyl, $R^{8A}$-substituted or unsubstituted 3 to 6 membered heterocycloalkyl, $R^{8A}$-substituted or unsubstituted $C_6$-$C_{10}$ aryl, or $R^{8A}$-substituted or unsubstituted 5 to 6 membered heteroaryl; and $R^{8A}$ is halogen, —$CF_3$, —$CCl_3$, —$CBr_3$, —$CI_3$, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —$NHSO_2H$, —NHC(O)H, —NHC(O)—OH, —NHOH, —$OCF_3$, —$OCCl_3$, —$OCBr_3$, $OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$-$C_{10}$ aryl, or unsubstituted 5 to 6 membered heteroaryl.

Embodiment 16. The compound of any one of embodiments 1 to 15, wherein ring A is $R^8$-substituted or unsubstituted $C_6$-$C_{10}$ aryl.

Embodiment 17. The compound of any one of embodiments 1 to 16, wherein:

ring A is $R^8$-substituted or unsubstituted phenyl or $R^8$-substituted or unsubstituted naphthyl; and $R^8$ is halogen or unsubstituted $C_1$-$C_6$ alkyl.

Embodiment 18. The compound of any one of embodiments 1 to 17, wherein $R^8$ is methyl.

Embodiment 19. The compound of any one of embodiments 1 to 18, wherein $R^1$ is hydrogen or substituted or unsubstituted $C_1$-$C_3$ alkyl.

Embodiment 20. The compound of any one of embodiments 1 to 19, wherein $R^1$ is hydrogen.

Embodiment 21. The compound of any one of embodiments 1 to 20, wherein $R^1$ is substituted or unsubstituted $C_1$-$C_3$ alkyl.

Embodiment 22. The compound of any one of embodiments 1 to 21, wherein $R^1$ is methyl.

Embodiment 23. The compound of any one of embodiments 1 to 22, wherein $R^2$ and $R^3$ are independently hydrogen.

Embodiment 24. The compound of any one of embodiments 1 to 23, wherein $R^5$ is halogen.

Embodiment 25. The compound of any one of embodiments 1 to 24, wherein $R^5$ is —F.

Embodiment 26. The compound of any one of embodiments 1 to 25, wherein z is 0.

Embodiment 27. The compound of any one of embodiments 1 to 26, wherein the compound is:

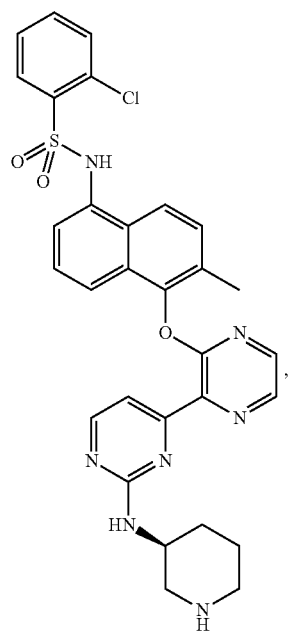

103
-continued
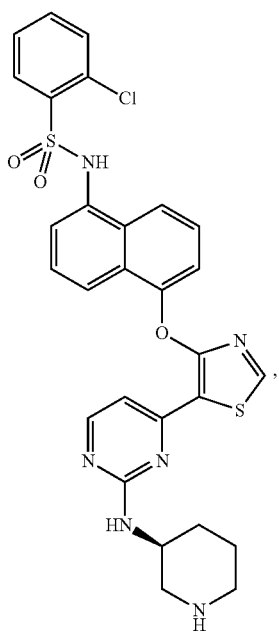
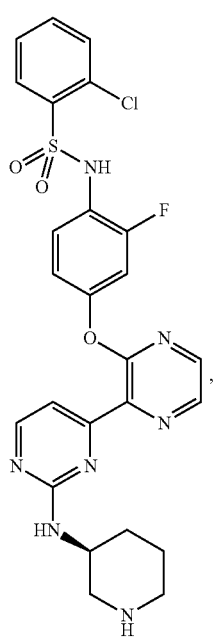
104
-continued
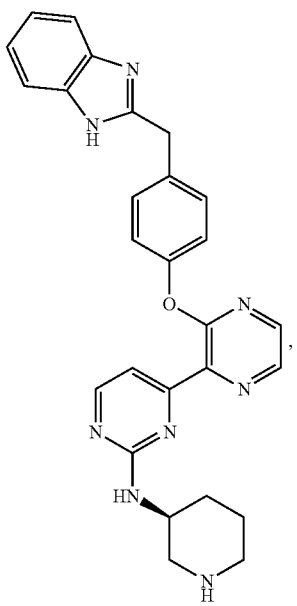
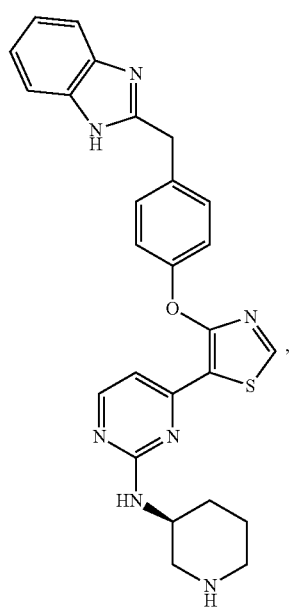

105
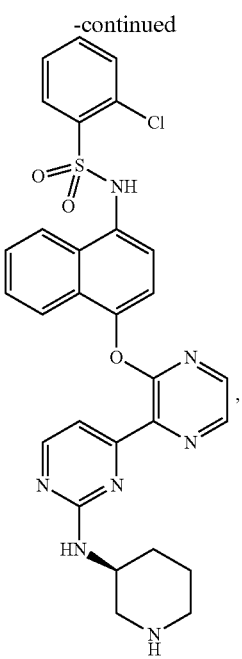
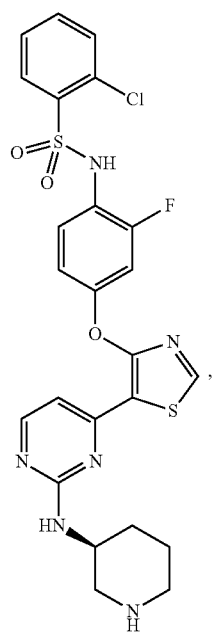
106
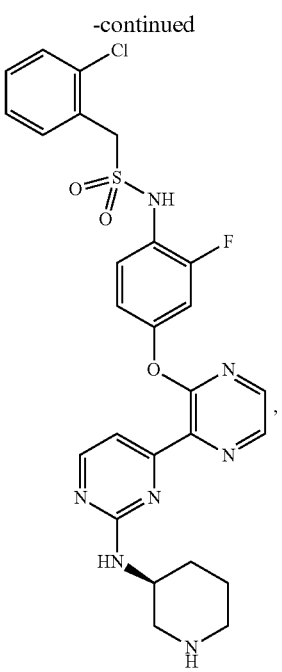
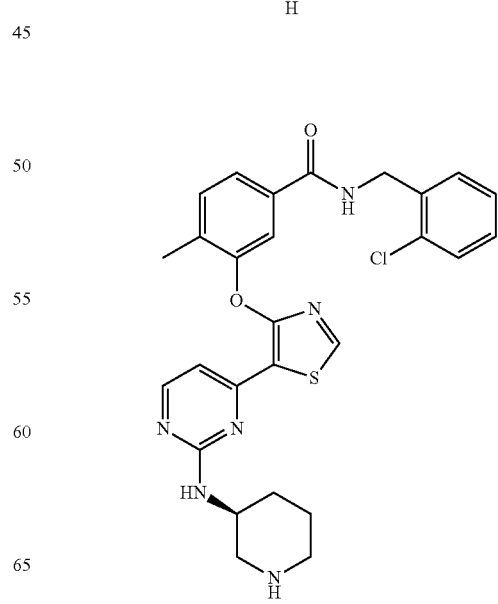

107
-continued
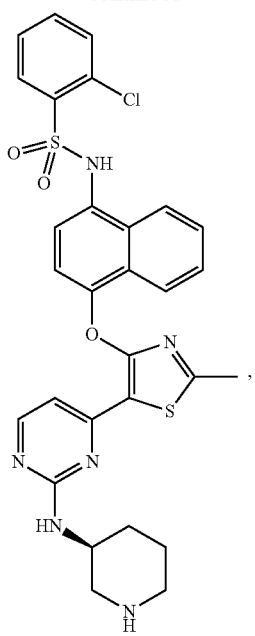
108
-continued
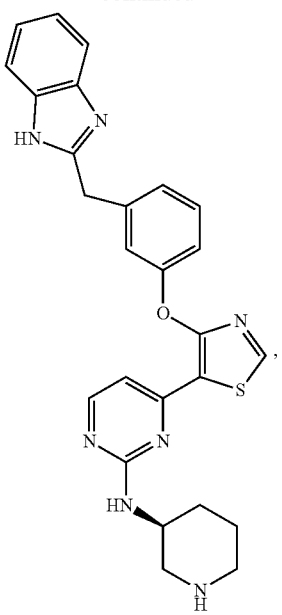
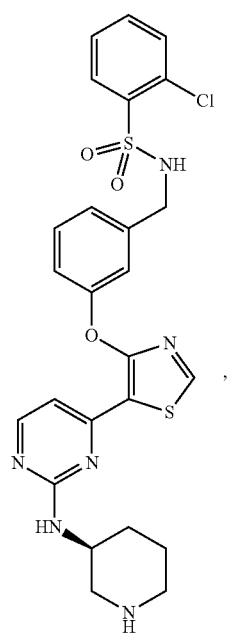
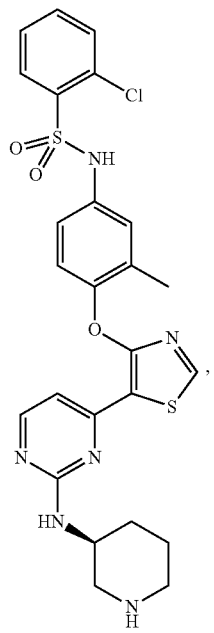

-continued

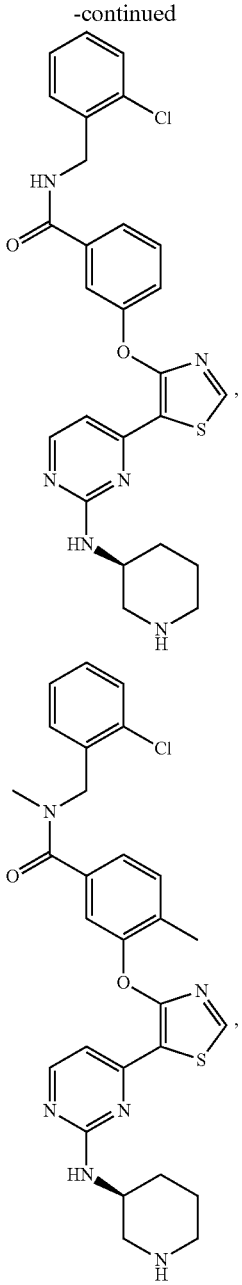

-continued

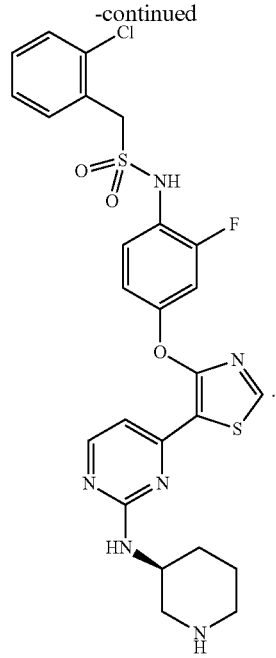

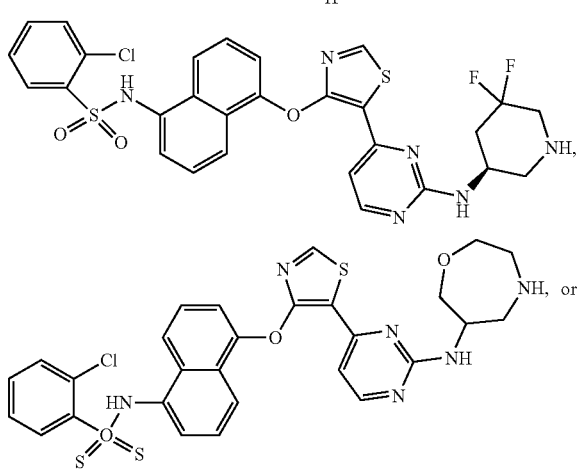

Embodiment 28. A pharmaceutical composition comprising a compound of any one of embodiments 1 to 27, and a pharmaceutically acceptable carrier.

Embodiment 29. The pharmaceutical composition of embodiment 28 for use in treating cell degenerative disorders modulated by Inositol-Requiring Enzyme 1α (IRE1α).

Embodiment 30. The pharmaceutical composition of embodiments 28 or 29 for use in treating neurodegenerative disorders, inflammatory disorders, fibrosing disorders, demyelinating disorders, peripheral neuropathies, dermatologic disorders, rheumatologic and autoimmune disorders, diabetes mellitus, or eye indications.

Embodiment 31. The pharmaceutical composition of embodiment 30, wherein the inflammatory disorder is general gastro-intestinal tract inflammation or chronic inflammatory lung disease.

Embodiment 32. The pharmaceutical composition of embodiment 31, wherein the general gastro-intestinal tract inflammation is an Inflammatory Bowel Disease (IBD), Crohn's disease, or colitis.

Embodiment 33. The pharmaceutical composition of embodiment 31, wherein the chronic inflammatory lung disease is bronchial asthma, chronic obstructive pulmonary disease (COPD), bronchiectasis or cystic fibrosis (CF).

Embodiment 34. A method of treating neurodegenerative disorders, inflammatory disorders, fibrosing disorders, demyelinating disorders, peripheral neuropathies, dermatologic disorders, rheumatologic and autoimmune disorders, diabetes mellitus, or eye indications, comprising administering to a subject in need thereof a therapeutically effective amount of a compound of any one of embodiments 1 to 27 or a pharmaceutical composition of embodiments 28 or 29.

Embodiment 35. The method of embodiment 34, wherein the inflammatory disorder is general gastro-intestinal tract inflammation or chronic inflammatory lung disease.

Embodiment 36. The method of embodiment 35, wherein the gastro-intestinal tract inflammation is an Inflammatory Bowel Disease (IBD), Crohn's disease, or colitis.

Embodiment 37. The method of embodiment 35, wherein the chronic inflammatory lung disease is bronchial asthma, chronic obstructive pulmonary disease (COPD), bronchiectasis or cystic fibrosis (CF).

EXAMPLES

Identification of IRE1α and IRE1β Modulators

In embodiments, compounds described herein possess at least one property or characteristic that is of therapeutic relevance. Candidate inhibitors may be identified by using, for example, an art-accepted assay or model. The Example section described assay(s) that were used to determine the IRE1α and the IRE1β modulatory activity of the compounds described herein, as well as assays that could be used to evaluate one or more characteristics of the compounds; the skilled artisan is aware of other procedures, assay formats, and the like that can be employed to generate data and information useful to assess the IRE1α and the IRE1β modulators described herein.

After identification, candidate inhibitors can be further evaluated by using techniques that provide data regarding characteristics of the modulators (e.g., pharmacokinetic parameters). Comparisons of the candidate modulators to a reference standard (which may the "best-of-class" of current modulators) are indicative of the potential viability of such candidates. IRE1α and IRE1β modulators that can serve as reference or benchmark compounds include those shown to demonstrate desired activity and characteristics useful for analyzing candidate modulators which will be apparent to the skilled artisan.

Chemical Syntheses

Example 1. Synthesis of (S)-1-(2-chlorophenyl)-N-(2-fluoro-4-(5-(2-(piperidin-3-ylamino)pyrimidin-4-yl)thiazol-4-yloxy)phenyl)methane sulfonamide TFA salt (compound 11)

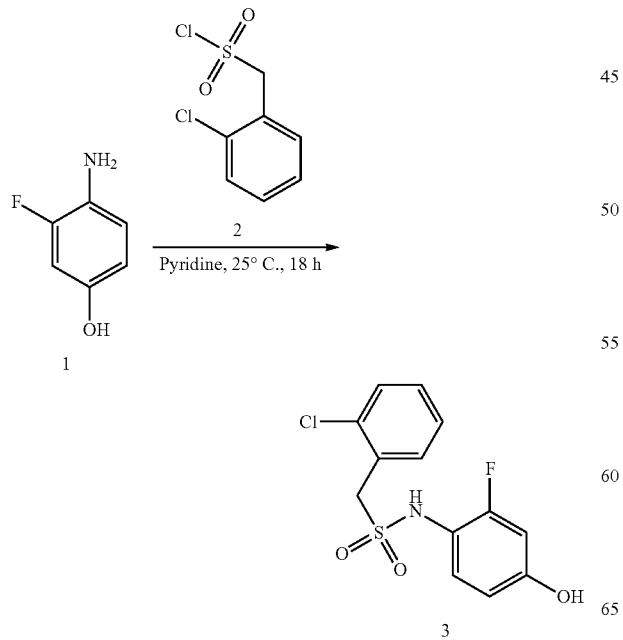

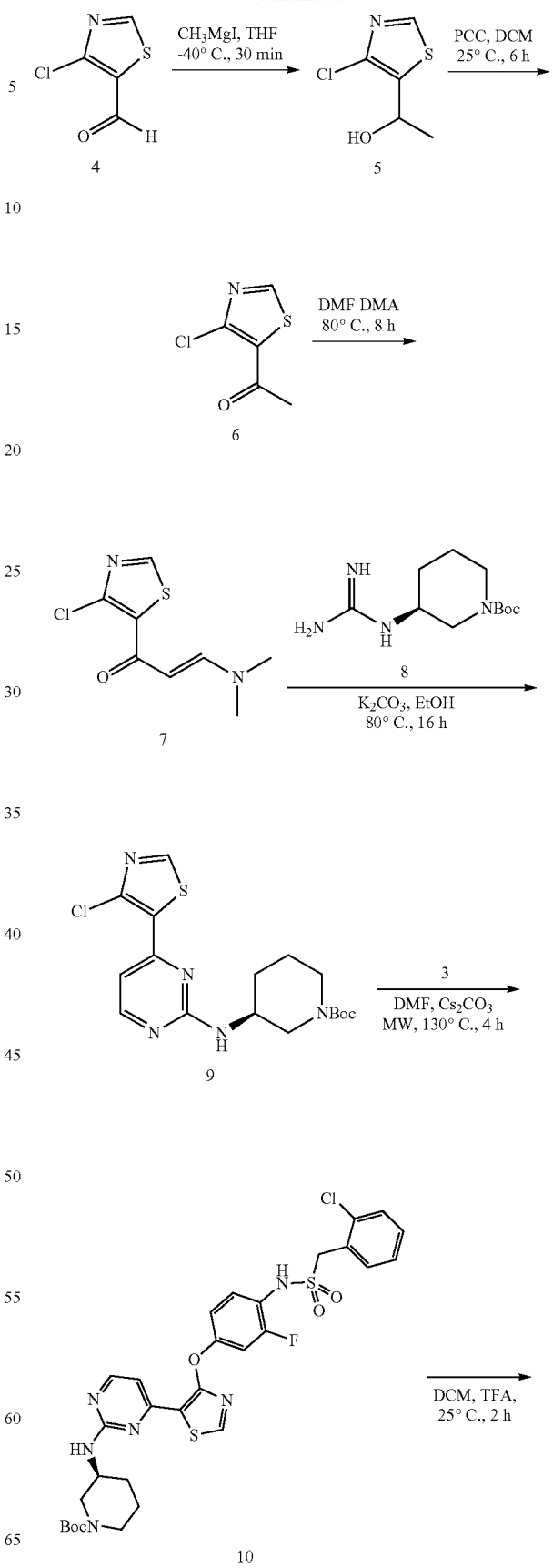

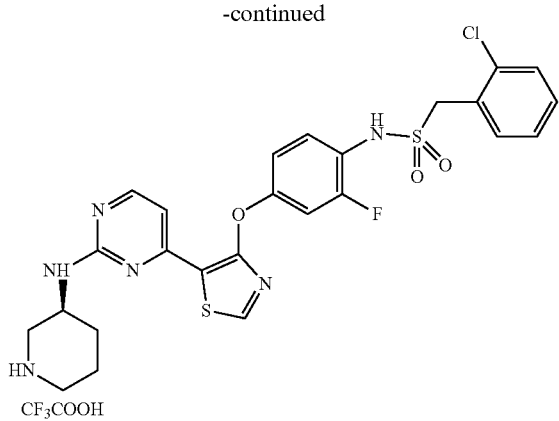

11

Compound 3. To a solution of 1 (100 mg, 0.78 mmol, 1.0 eq) in pyridine (2 ml) was added compound 2 (177 mg, 0.78 mmol, 1.0 eq) at 25° C. The reaction mixture was stirred at 25° C. for 18 h. After 18 h, reaction mass was concentrated to provide crude material. The crude material was treated with water (10 ml) and extracted with ethyl acetate (2×20 ml). The combined organic layer was washed with brine solution (2×20 ml), dried over anhydrous $Na_2SO_4$, filtered and the solvent was removed in vacuo. the residue was purified through silica gel column chromatography (60-120 silica gel) using hexane/ethyl acetate as eluent (85:15) to afford 3 (190 mg, 76%) as a brown solid. ms (esi neg. ion) m/z: 314.1.

Compound 5: To a solution of 4 (1 g, 6.76 mmol, 1.0 eq.) in THF (30 mL) was added methyl magnesium iodide (3.0 M in THF, 3.4 mL, 10.14 mmol, 1.5 eq.) at −40° C. and stirred for 30 min at same temperature. After reaction completion, saturated $NH_4Cl$ solution (2 mL) was added to the reaction mixture and followed by extraction with EtOAc (3×20 ml). The combined organic layers were dried over sodium sulfate, concentrated and purified by column chromatography (60-120 silica gel; gradient elution with 10% EtOAC in hexane) to afford 5 (970 mg, 98%) as a pale yellow solid. MS (ESI pos. ion) m/z: 164.2; $^1$H-NMR (300 MHz, $CDCl_3$): δ 8.64 (s, 1H), 5.32-5.24 (m, 1H), 1.57 (d, J=2.7 Hz, 3H).

Compound 6: To a solution of 5 (970 mg, 5.95 mmol, 1.0 eq.) in DCM (30 mL) was added pyridinium chlorochromate (3.85 g, 17.85 mmol, 3.0 eq.) portion-wise at 25° C. over a period of 5 min and the reaction was stirred for 6 h at same temperature. After reaction completion, the mixture was filtered through celite pad and washed with DCM (15 ml). The filtrate was concentrated and purified by column chromatography (60-120 silica gel; gradient elution with 20% EtOAC in hexane) to afford 6 (800 mg, 83%) as a white solid. MS (ESI pos. ion) m/z: 162.1; $^1$H-NMR (300 MHz, $CDCl_3$): δ 8.84 (s, 1H), 2.72 (s, 3H).

Compound 7: solution of 6 (800 mg, 4.90 mmol, 1.0 eq.) in DMF:DMA (8 mL, 95%) was stirred at 80° C. for 8 h. After reaction completion, the mixture was poured into ice water and extracted with EtOAc (3×20 mL). The combined organic layers were dried and concentrated to obtain 7 (880 mg, 82%) as a brown solid. MS (ESI pos. ion) m/z: 217.2; $^1$H-NMR (300 MHz, $CDCl_3$): δ 8.71 (s, 1H), 7.85 (d, J=7.2 Hz, 1H), 6.03 (d, J=7.2 Hz, 1H), 3.20 (s, 3H), 2.97 (s, 3H).

Compound 9: To a solution of 8 (1.28 g, 4.62 mmol, 2.0 eq.) in EtOH (10 mL) was added $K_2CO_3$ (1.91 g, 13.9 mmol, 6.0 eq.) followed by compound 7 (500 mg, 2.31 mmol, 1.0 eq.) at 25° C. and the mixture was stirred at 80° C. for 18 h. After reaction completion, the mixture was filtered, concentrated and purified by column chromatography (60-120 silica gel, gradient elution with 20% EtOAc in hexane) to afford 9 (350 mg, 38%) as a white solid. MS (ESI pos. ion) m/z: 396.4; $^1$H-NMR (500 MHz, $CDCl_3$): δ 8.75 (s, 1H), 8.39 (d, J=5 Hz, 1H), 7.49 (d, J=5 Hz, 1H), 5.21 (d, J=7 Hz, 1H), 3.99-3.96 (m, 1H), 3.71-3.66 (m, 1H), 3.47-3.42 (m, 2H), 1.98-1.94 (m, 1H), 1.71-1.66 (m, 2H), 1.61-1.57 (m, 2H), 1.40 (s, 9H).

Compound 10: To the solution of 3 (60 mg, 0.18 mmol, 1.0 eq.) in DMF (2 mL) was added $Cs_2CO_3$ (124 mg, 0.37 mmol, 2.0 eq.) followed by 8 (75 mg, 0.18 mmol, 1.0 eq.) at 25° C. The reaction mixture was microwaved at 130° C. for 4 h. The reaction mixture was then poured into ice water (10 mL) and extracted with ethyl acetate (2×20 mL). The combined organic layers were washed with brine solution (2×20 mL), dried over anhydrous $Na_2SO_4$, filtered and the solvent was removed in vacuo. The residue was purified through silica gel column chromatography (60-120 silica gel) using hexane/acetone as eluent (80:20) to afford 10 (30 mg, 23%) as a brown liquid. MS (ESI pos. ion) m/z: 675.4.

Compound 11: To a solution of 10 (30 mg, 0.04 mmol) in DCM (5 mL) was added TFA (0.1 mL) at 25° C. Reaction mixture was stirred for 2 h. The mixture was concentrated and purified by prep-HPLC to afford the 11 (10 mg, 40%) as a brown solid and TFA salt. MS (ESI pos. ion) m/z: 575.4; $^1$H NMR (300 MHz, DMSO-d6): δ 9.88 (s, 1H), 9.11 (s, 1H), 8.63 (brs, 2H), 8.39 (d, J=5.4 Hz, 1H), 7.53-7.49 (m, 3H), 7.41-7.33 (m, 3H), 7.24 (dd, J=11.1, 2.7 Hz, 1H), 7.18 (d, J=5.1 Hz, 1H), 6.96 (dd, J=9.0, 1.5 Hz, 1H), 4.65 (s, 2H), 3.39-3.35 (m, 1H), 3.21-3.18 (m, 2H), 2.91-2.85 (m, 2H), 1.98-1.88 (m, 2H), 1.75-1.53 (m, 2H).

Example 2. Synthesis of (S)—N-(2-chlorophenyl)-4-methyl-3-(5-(2-(piperidin-3-ylamino) pyrimidin-4-yl) thiazol-4-yloxy)benzamide TFA salt (compound 16 (LBC-364))

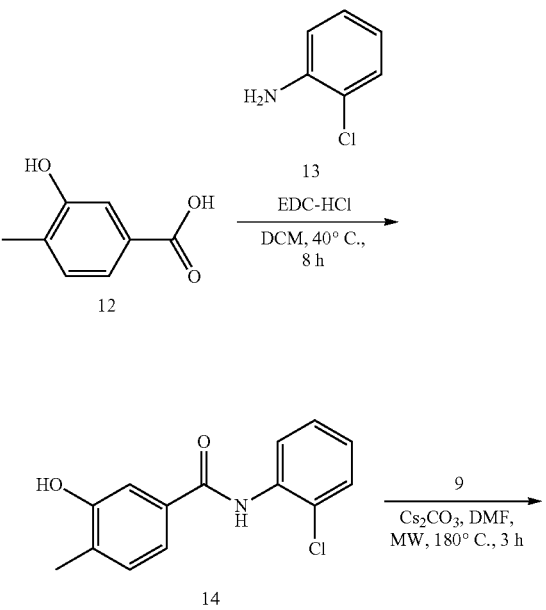

7.59 (s, 1H), 7.54-7.50 (m, 3H), 7.45-7.41 (m, 1H), 7.39-7.34 (m, 1H), 7.31-7.26 (m, 2H), 4.13-4.09 (m, 1H), 3.21-3.16 (m, 2H), 2.87-2.83 (m, 2H), 2.32 (s, 3H), 1.98-1.88 (m, 2H), 1.71-1.57 (m, 2H).

Example 3. Synthesis of (S)—N-(2-chlorobenzyl)-4-methyl-3-(5-(2-(piperidin-3-ylamino) pyrimidin-4-yl) thiazol-4-yloxy) benzamide TFA salt (compound 20 (LBC-365))

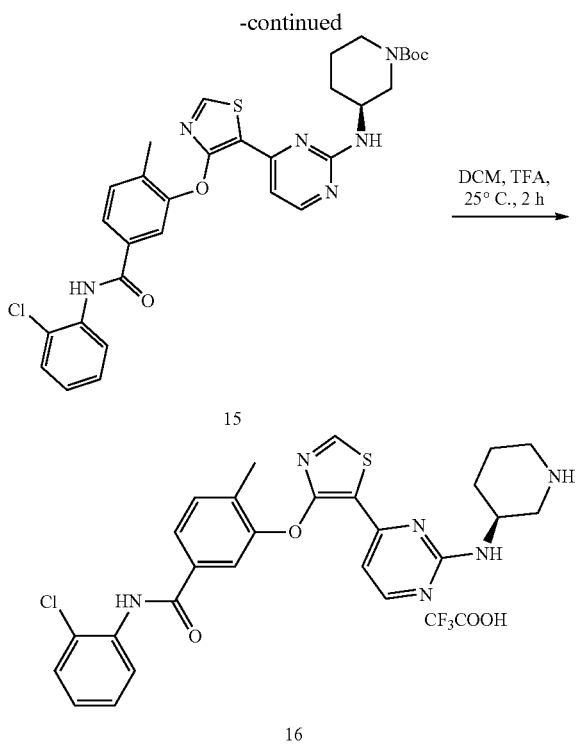

Compound 14: To the solution of compound 12 (100 mg, 0.65 mmol, 1.0 eq.) and 13 (83 mg, 0.65 mmol, 1.0 eq.) in DCM (10 mL) was added EDC-HCl (126 mg, 0.65 mmol, 1.0 eq.) at 25° C. The reaction mixture was stirred at 40° C. for 8 h. The reaction mixture was then quenched and with 1N HCl (10 mL) and neutralized with a sat. NaHCO₃ solution (10 mL). The aqueous layer was extracted with ethyl acetate (3×30 mL). The combined organic layers were washed with a brine solution (2×30 mL), dried over anhydrous Na₂SO₄, filtered and the solvent was removed in vacuo. The residue was purified through silica gel column chromatography (60-120 silica gel) using hexane/ethyl acetate as eluent (90:10) to afford 14 (50 mg, 30% as a white solid. MS (ESI pos. ion) m/z: 262.2; ¹H-NMR (300 MHz, CDCl₃) δ 9.82 (s, 1H), 9.68 (s, 1H), 7.60 (dd, J=7.8, 1.5 Hz, 1H), 7.54 (dd, J=7.8, 1.5 Hz, 1H), 7.40-7.35 (m, 3H), 7.28 (dd, J=7.8, 1.5 Hz, 1H), 7.20 (d, J=8.1 Hz, 1H), 2.18 (s, 3H).

Compound 15: To a solution of compound 14 (50 mg, 0.19 mmol, 1.0 eq.) in DMF (2 mL) was added Cs₂CO₃ (125 mg, 0.72 mmol, 2.0 eq.) and 9 (75 mg, 0.19 mmol, 1.0 eq.) at 25° C. The reaction mixture was microwaved at 180° C. for 3 h. After 3 h, reaction mixture was poured into ice water (10 mL) and extracted with ethyl acetate (2×20 mL) The combined organic layers were washed with a brine solution (2×20 mL), dried over anhydrous Na₂SO₄, filtered and the solvent was removed in vacuo. The residue was purified through silica gel column chromatography (60-120 basic silica gel) using hexane/acetone as eluent (80:20) to afford 15 (50 mg, 42%) as a brown liquid. MS (ESI pos. ion) m/z: 621.4.

Compound 16: To a solution of 15 (100 mg, 0.16 mmol) in DCM (10 mL) was added TFA (0.3 mL) at 25° C. The reaction mixture was stirred for 2 h, concentrated and purified by prep-HPLC to give 16 (25 mg, 30%) as a brown solid and TFA salt. MS (ESI pos. ion) m/z: 521.4. ¹H NMR (300 MHz, DMSO-d₆): δ 10.05 (s, 1H), 9.05 (s, 1H), 8.65 (brs, 2H), 8.40 (d, J=5.4 Hz, 1H), 7.81 (d, J=7.8 Hz, 1H), Compound 18: To a solution of 16 (500 mg, 3.28 mmol, 1.0 eq.) and 17 (464 mg, 3.28 mmol, 10 eq.) in DCM (20 mL) was added EDC-HCl (630 mg 3.28 mmol 1.0 eq) at 25° C. The reaction mixture was stirred at 25° C. for 18 h. Then the reaction mass was poured into 1N HCl (20 mL) to provide a solid. The solid was filtered, washed with water (20 mL) and it was dried to give 18 (400 mg, 45%) as a white solid. MS (ESI pos. ion) m/z: 521.4 ¹H NMR (300 MHz, CDCl₃): δ 9.56 (s, 1H), 8.87 (t, J=5.7 Hz, 1H), 7.46-7.43 (m, 1H), 7.32-7.27 (m, 4H), 7.15 (d, J=7.8 Hz, 1H), 4.49 (d, J=6.0 Hz, 2H), 2.15 (s, 3H).

Compound 19: To the solution of 18 (100 mg, 0.36 mmol, 1.0 eq.) in DMF (3 mL) was added Cs₂CO₃ (236 mg, 0.72 mmol, 2.0 eq.) and 9 (143 mg, 0.36 mmol, 1.0 eq.) at 25° C. The reaction mixture was then microwaved at 180° C. for 3 h. After 3 h, reaction mixture was poured into ice water (10 mL) and extracted with ethyl acetate (2×20 mL) The combined organic layers were washed with a brine solution (2×20 mL), dried over anhydrous Na₂SO₄, filtered and the solvent was removed in vacuo. The residue was purified by silica gel column chromatography (60-120 silica gel) using hexane/acetone as eluent (80:20) to afford 19 (90 mg, 39%) as a brown liquid. MS (ESI pos. ion) m/z: 635.5.

Compound 20: To the solution of 18 (100 mg, 0.36 mmol, 1.0 eq.) in DMF (3 mL) was added Cs₂CO₃ (236 mg, 0.72 mmol, 2.0 eq.) and 9 (143 mg, 0.36 mmol, 1.0 eq.) at 25° C. The reaction mixture was then microwaved at 180° C. for 3 h. After 3 h, reaction mixture was poured into ice water (10 mL) and extracted with ethyl acetate (2×20 mL) The combined organic layers were washed with a brine solution (2×20 mL), dried over anhydrous Na₂SO₄, filtered and the solvent was removed in vacuo. The residue was purified by silica gel column chromatography (60-120 silica gel) using hexane/acetone as eluent (80:20) to afford 19 (90 mg, 39%) as a brown liquid. MS (ESI pos. ion) m/z: 635.5.

Example 4. Synthesis of (S)-tert-butyl 3-(4-(4-(4-(2-chlorophenylsulfonamido)-3-fluorophenoxy)thiazol-5-yl)pyrimidin-2 ylamino)piperidine-1-carboxylate TFA salt (compound 25 (LBC-362))

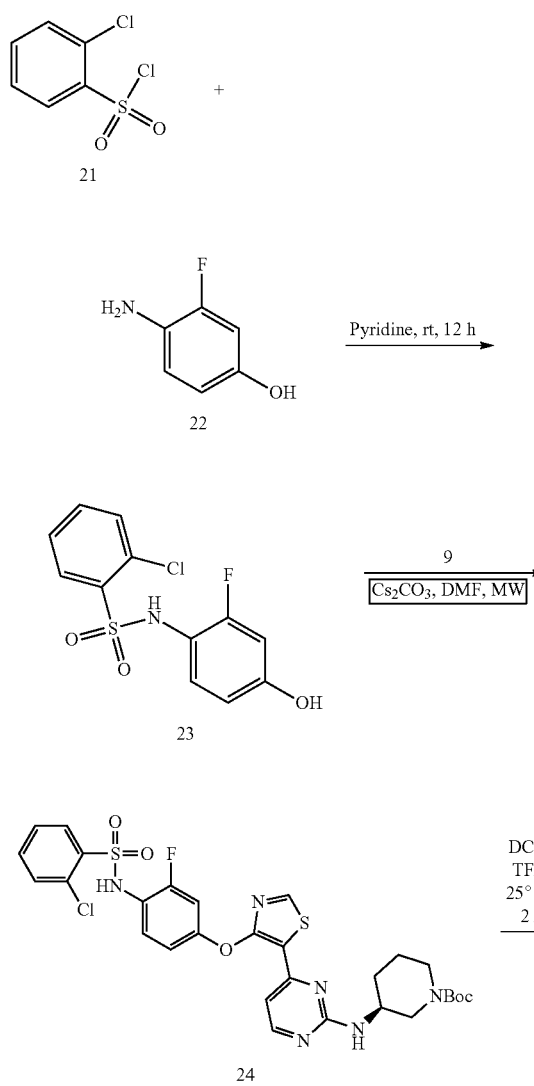

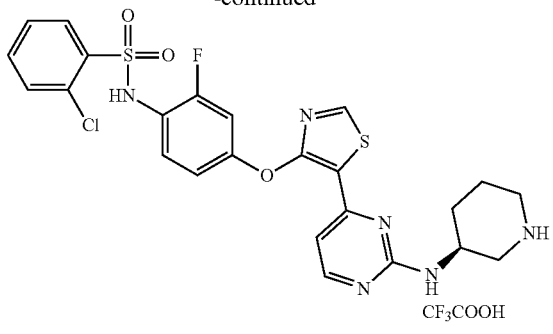

Compound 24: Compound 23 (100 mg, 0.30 mmol) in DMF (3 mL), compound 9 (131 mg, 0.33 mmol) and Cs₂CO₃ (395 mg, 0.99 mmol) were added to a 10 mL microwave tube and heated to 180° C. for 45 min. The reaction mixture was diluted with EtOAc (30 mL) and filtered. The solvent was evaporated in vacuo. The residue was purified by silica gel column chromatography (60-120 silica gel) using hexane/ethyl acetate as eluent (70:30) to afford 24 (60 mg, 55%) as a gummy material. MS (ESI pos. ion) m/z: 661.3.

Compound 25: To a stirred solution of 24 (60 mg, 0.09 mmol) in DCM (3 mL) was added TFA (0.3 mL) dropwise at 0° C. The mixture was stirred 2 h at room temperature, concentrated in vacuo and purified by prep-HPLC to afford 25 (15 mg, 30%) as a brown colored solid and TFA salt. MS (ESI pos. ion) m/z: 561.3. ¹HNMR (300 MHz, DMSO-d₆): δ 10.33 (s, 1H), 9.08 (s, 1H), 8.68 (bs, 2H), 8.35 (d, J=5.4 Hz, 1H), 7.88-7.85 (m, 1H), 7.71-7.62 (m, 2H), 7.50-7.45 (m, 2H), 7.22 (t, J=8.7 Hz, 1H), 7.14-7.10 (m, 2H), 6.93-6.90 (m, 1H), 4.09 (br, 1H), 3.35 (d, J=9.9 Hz, 1H), 3.18 (d, J=14.1 Hz, 1H), 2.88-2.85 (m, 2H), 1.92-1.87 (m, 2H), 1.70-1.55 (m, 2H).

Example 5. Synthesis of (S)-4-(4-(4-((1H-benzo[d]imidazol-2-yl)methyl)phenoxy)thiazol-5-yl)-N-(piperidin-3-yl)pyrimidin-2-amine (compound 30 (LBC-352))

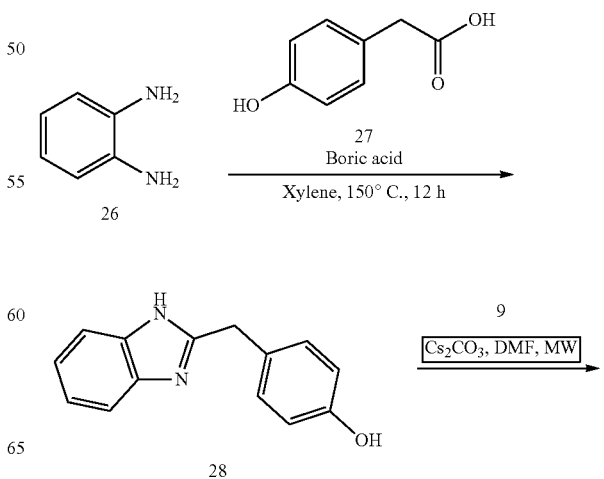

119

-continued

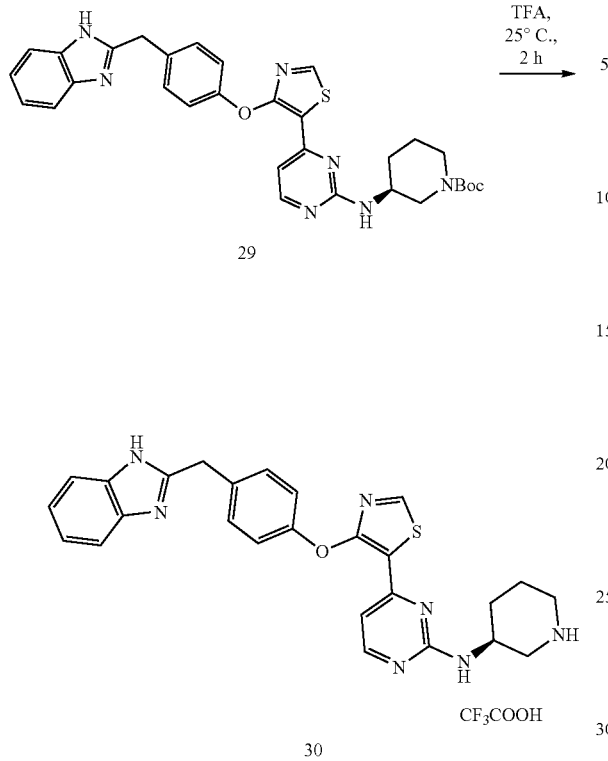

Compound 28: To a stirred solution of compound 26 (1 g, 9.2 mmol) in xylene (20 mL) were added compound 27 (2.1 g, 13.8 mmol) and boric acid (60 mg, 0.92 mmol) under $N_2$ atmosphere. The reaction mixture was stirred at 150° C. After 12 h, the reaction mixture was cooled to room temperature and the solvent was removed in vacuo. The residue was purified by silica gel column chromatography (60-120 silica gel) using hexane/ethyl acetate as eluent (50:50) to afford 28 (490 mg, 25%) as a purple solid. MS (ESI pos. ion) m/z: 225.3. $^1$H-NMR (300 MHz, DMSO-$d_6$): δ 12.33 (bs, 1H), 9.50 (bs, 1H), 7.46 (brs, 2H), 7.14-7.08 (m, 4H), 6.72 (d, J=8.4 Hz, 2H), 4.05 (s, 2H).

Compound 29: A solution of 28 (100 mg, 0.44 mmol) in DMF (3 mL), 9 (175 mg, 0.44 mmol) and $Cs_2CO_3$ (420 mg, 1.33 mmol) were added to a 10 mL microwave tube and heated to 180° C. for 45 min. The reaction mixture was then diluted with EtOAc (30 mL), filtered and evaporated in vacuo. The residue was purified by silica gel column chromatography (60-120 silica gel) using hexane/ethyl acetate as eluent (70:30) to afford 29 as a gummy material that was taken onto the next step. MS (ESI pos. ion) m/z: 584.4.

Compound 30: To a stirred solution of 29 (unpurified, 150 mg) in DCM (3 mL) at 0° C. was added TFA (0.3 mL) dropwise. After 2 h, the reaction mixture was concentrated in vacuo and purified by prep-HPLC to give 30 as a brown solid and TFA salt. MS (ESI pos. ion) m/z: 484.4. $^1$H NMR (300 MHz, DMSO-$d_6$): δ 9.07 (s, 1H), 8.71 (bs, 2H), 8.36 (d, J=5.1 Hz, 1H), 7.78-7.74 (m, 2H), 7.53-7.50 (m, 2H), 7.47-7.44 (m, 3H), 7.19-7.13 (m, 3H), 4.52 (s, 2H), 3.39-3.34 (m, 2H), 2.86 (m, 4H), 1.94-1.87 (m, 3H), 1.70-1.56 (m, 4H).

120

Example 6. Synthesis of (S)-4-(4-(3-((1H-benzo[d]imidazol-2-yl)methyl)phenoxy)thiazol-5-yl)-N-(piperidin-3-yl)pyrimidin-2-amine TFA salt (compound 35 (LBC-370)

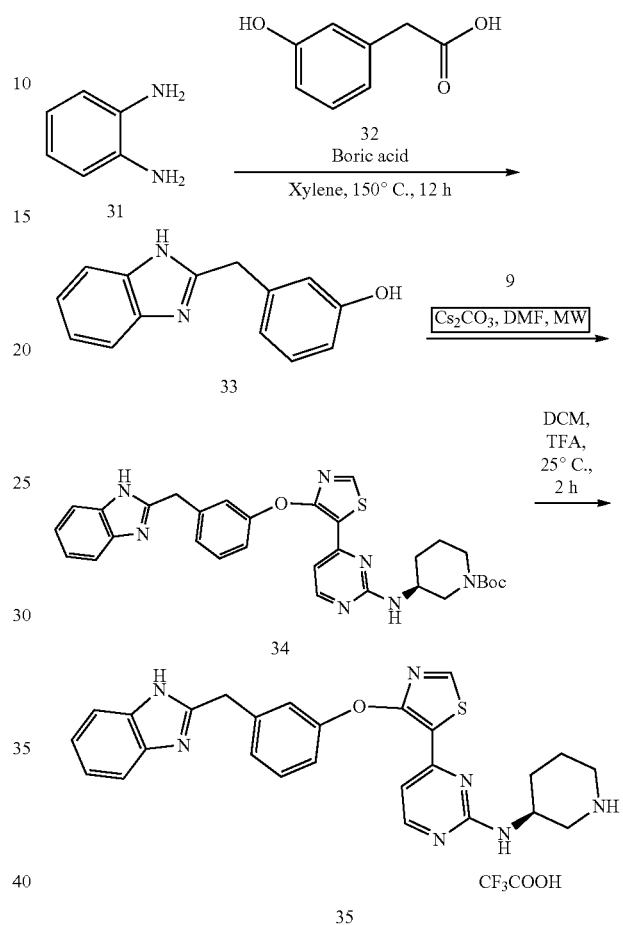

Compound 33: To a stirred solution of 31 (1 g, 9.2 mmol) in xylene (20 mL) under $N_2$ atmosphere was added compound 32 (2.1 g, 13.8 mmol) and boric acid (60 mg, 0.92 mmol). The reaction mixture was stirred at 150° C. After 12 h, the reaction mixture was cooled to room temperature and solvent was removed in vacuo. The residue was purified by silica gel column chromatography (60-120 silica gel) using hexane/ethyl acetate as eluent (50:50) to afford 33 (800 mg, 40%) as a purple solid. MS (ESI pos. ion) m/z: 225.3; $^1$H NMR (300 MHz, DMSO-$d_6$): δ 12.33 (bs, 1H), 9.34 (s, 1H), 7.48-7.45 (m, 2H), 7.14-7.10 (m, 2H), 7.07 (s, 1H), 6.75-6.70 (m, 1H), 6.63-6.60 (m, 2H), 4.07 (s, 1H).

Compound 34: To a stirred solution of 33 (100 mg, 0.44 mmol) in DMF (3 mL) in 10 mL microwave tube was added 9 (175 mg, 0.44 mmol) and $Cs_2CO_3$ (420 mg, 1.33 mmol). The reaction mixture was heated to 180° C. for 45 min then diluted with EtOAc (30 mL) and filtered. The solvent was evaporated in vacuo to provide 200 mg of unpurified 34 as a gummy material that was used in the next step. MS (ESI pos. ion) m/z: 584.5.

Compound 35: To a stirred solution of 34 (Crude, 200 mg) in DCM (3 mL) 0° C. was added TFA (0.3 mL) dropwise. The mixture was stirred room temperature for 2 h, concentrated in vacuo and purified by prep-HPLC to give 35 (14 mg) as a thick brown solid and TFA salt. MS (ESI pos. ion) m/z: 584.5; $^1$H NMR (300 MHz, DMSO-d6): δ 9.07 (s, 1H), 8.67 (br, 2H), 8.35 (d, J=5.4 Hz, 1H), 7.76-7.73 (m, 2H), 7.50-7.47 (m, 2H), 7.43 (t, J=5.7 Hz, 2H), 7.28 (d, J=2.1 Hz, 1H), 7.24-7.17 (m, 2H), 7.11-7.06 (m, 1H), 4.51 (s, 2H), 3.36 (d, J=10.2 Hz, 1H), 3.19 (m, 2H), 2.87 (d, J=6.3 Hz, 2H), 1.94-1.88 (m, 2H), 1.70-1.55 (m, 2H).

Example 7. Synthesis of (S)-2-chloro-N-(4-methyl-3-(5-piperidin-3-ylamino)pyrimidin-4-yl)thiazol-4-yloxy)phenyl)benzenesulfonamide TFA salt (compound 39 (LBC-371)

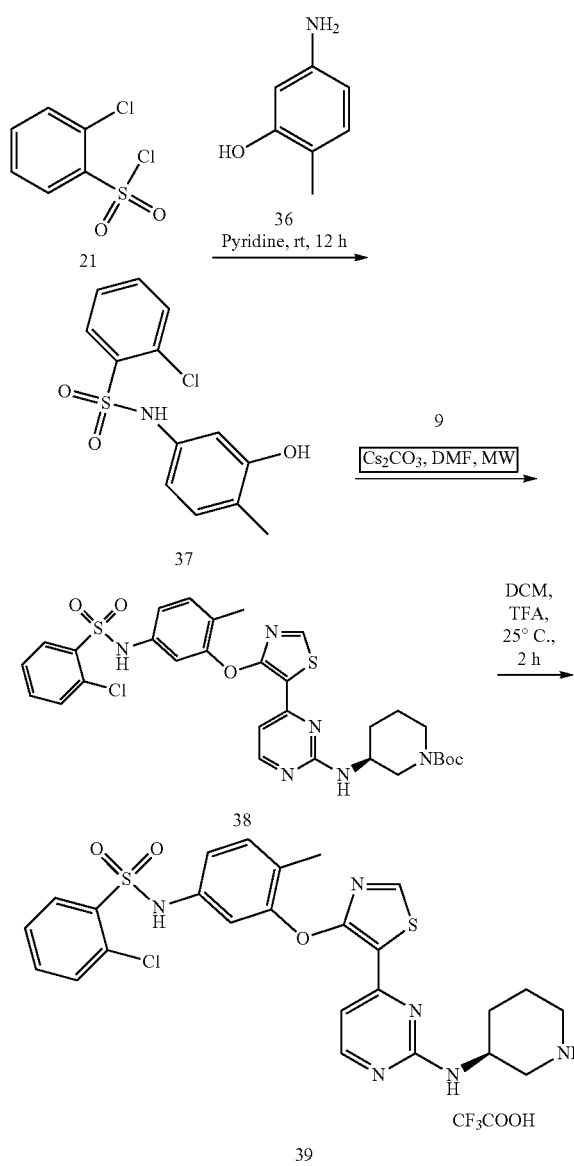

Compound 37: To a stirred solution of 36 (500 mg, 4.06 mmol) in pyridine (5 mL) was added 21 (0.5 mL, 3.77 mmol) at room temperature. The reaction mixture was stirred 12 h, quenched with 2N HCl (10 mL) and extracted with EtOAc (30 mL). The combined organic layers were washed with a brine solution (2×20 mL), dried over anhydrous Na$_2$SO$_4$, filtered and the solvent was removed in vacuo. The residue was purified by silica gel column chromatography (60-120 silica gel) using hexane/ethyl acetate as eluent (75:25) to give 37 (500 mg, 42%) as a red solid. MS (ESI pos. ion) m/z: 298.2; $^1$H NMR (300 MHz, DMSO-d$_6$): δ 10.32 (bs, 1H), 9.37 (s, 1H), 7.97 (d, J=7.5 Hz, 1H), 7.62-7.59 (m, 2H), 7.52-7.48 (m, 1H), 6.84 (t, J=8.1 Hz, 1H), 6.63 (d, J=2.1 Hz, 1H), 6.44 (dd, J=8.1, 2.1 Hz, 1H), 1.95 (s, 3H).

Compound 38: To 37 (100 mg, 0.33 mmol) in a 10 mL microwave tube was added in DMF (3 mL), 9 (200 mg, 0.50 mmol) and Cs$_2$CO$_3$ (267 mg, 0.67 mmol). The solution was heated to 180° C. for 45 min then diluted with EtOAc (30 mL) and filtered. The solvent was evaporated in vacuo to afford 175 mg of 38 as a gummy material that was taken to the next step without purification. MS (ESI pos. ion) m/z: 657.4.

Compound 39: To a stirred solution of 38 (175 mg) in DCM (3 mL) at 0° C. was added TFA (0.3 mL) dropwise. After stirring 2 h at room temperature, the reaction mixture was concentrated in vacuo and purified through prep-HPLC to afford 39 (10 mg) as a light brown solid and TFA salt. MS (ESI pos. ion) m/z: 557.4; $^1$H NMR (300 MHz, DMSO-d$_6$): δ 10.29 (s, 1H), 9.35 (s, 1H), 7.63 (brs, 1H), 7.94 (d, J=6.1 Hz, 1H), 7.67-7.60 (m, 1H), 7.51-7.45 (m, 1H), 7.15-7.08 (m, 1H), 7.26 (d, J=6.0 Hz, 1H), 7.09 (d J=2.7 Hz, 1H), 6.84 (d, J=7.8 Hz, 1H), 6.44 (d, J=2.1 Hz, 1H), 4.11 (brs, 1H), 3.41-3.34 (m, 1H), 2.93-2.86 (m, 1H), 2.09 (d, J=10.8 Hz, 1H), 1.94 (s, 3H), 1.64-1.62 (m, 2H), 1.11-1.06 (m, 2H).

Example 8. Synthesis of (S)-2-chloro-N-(3-(5-(2-(piperidin-3-ylamino)pyrimidin-4-yl)thiazol-4-yloxy)benzyl)benzenesulfonamide TFA salt (compound 43 (LBC-367))

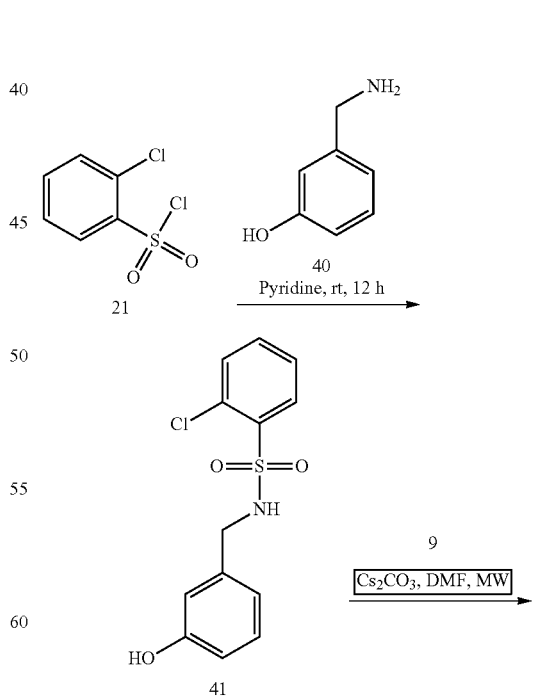

123

-continued

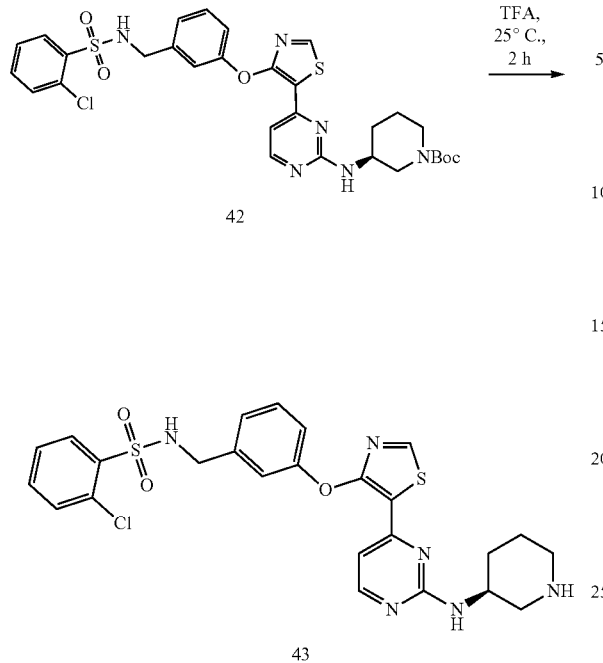

Compound 41: To a stirred solution of 0 (500 mg, 4.06 mmol) in pyridine (5 mL) was added 21 (0.5 mL, 3.77 mmol) at room temperature. After stirring 12 h, the reaction mixture was quenched with 2N HCl (10 mL) and extracted with EtOAc (30 mL). The combined organic layers were washed with a brine solution (2×20 mL), dried over anhydrous $Na_2SO_4$, filtered and the solvent was removed in vacuo. The residue was purified by silica gel column chromatography (60-120 silica gel) using hexane/ethyl acetate as eluent (75:25) to afford 41 (500 mg, 42%) as a purple solid. MS (ESI pos. ion) m/z: 298.2; $^1$H NMR (300 MHz, DMSO-$d_6$): δ 9.33 (s, 1H), 8.38 (t, J=6.0 Hz, 1H), 7.91 (d, J=7.51 Hz, 1H), 7.60-7.58 (m, 2H), 7.51-7.44 (m, 1H), 7.01 (t, J=7.8 Hz, 1H), 6.67-6.55 (m, 3H), 3.99 (d, J=6.3 Hz, 2H).

Compound 42: To 41 (100 mg, 0.33 mmol) in a 10 mL microwave tube was added DMF (3 mL), 9 (133 mg, 0.33 mmol) and $Cs_2CO_3$ (218 mg, 0.67 mmol). The mixture was heated to 180° C. for 45 min, then diluted with EtOAc (30 mL) and filtered. The solvent was evaporated in vacuo to afford 150 mg of 42 as a gummy material that was used in the next step without purification. MS (ESI pos. ion) m/z: 657.4

Compound 43: To a stirred solution of 42 (150 mg) in DCM (3 mL) at 0° C. was added TFA (0.3 mL) dropwise. After stirring 2 h at room temperature, the reaction mixture was concentrated in vacuo and purified by prep-HPLC to afford 43 (16 mg) as a light brown solid and TFA salt. MS (ESI pos. ion) m/z: 557.3. $^1$H NMR (300 MHz, DMSO-$d_6$): δ 9.08 (s, 1H), 8.86 (bs, 2H), 8.49 (t, J=6.3 Hz, 1H), 8.40 (d, J=5.1 Hz, 1H), 7.90 (d, J=1.2 Hz, 1H), 7.58-7.50 (m, 2H), 7.48-7.42 (m, 2H), 7.26 (t, J=9.0 Hz, 1H), 7.16 (d, J=5.1 Hz, 1H), 7.02 (d, J=7.5 Hz, 1H), 6.96-6.93 (m, 2H), 4.11 (d, J=6.3 Hz, 2H), 3.40-3.36 (m, 2H), 3.18-3.16 (m, 2H), 2.88-2.86 (m, 2H), 1.94-1.88 (m, 2H), 1.71-1.57 (m, 2H).

Example 9. Synthesis of (S)-2-chloro-N-(5-(5-(2-(piperidin-3-ylamino)pyrimidin-4-yl)thiazol-4-yloxy)naphthalen-1-yl)benzenesulfonamide TFA salt (compound 47 (LBC-348))

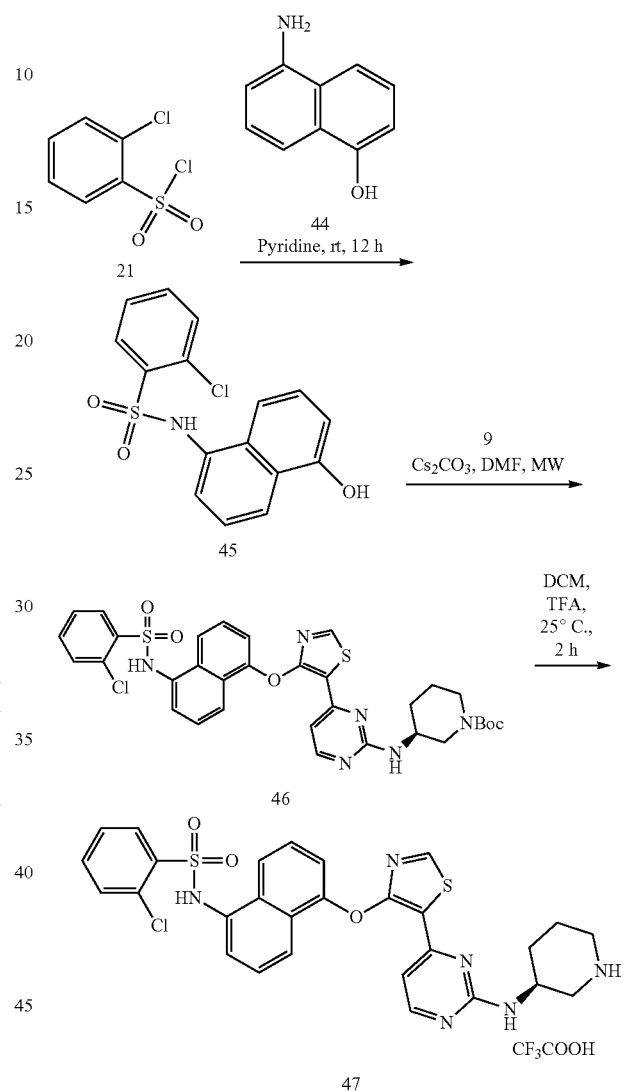

Compound 45: To a stirred solution of 44 (500 mg, 3.14 mmol) in pyridine (5 mL) was added 21 (0.5 mL, 3.77 mmol) at room temperature. The reaction mixture was stirred at room temperature for 12 h. After 12 h, the reaction mixture was quenched with 2N HCl (10 mL) and extracted with EtOAc (50 mL). The combined organic layers were washed with a brine solution (2×20 mL), dried over anhydrous $Na_2SO_4$, filtered and the solvent was removed in vacuo. The residue was purified by silica gel column chromatography (60-120 silica gel) using hexane/ethyl acetate as eluent (75:25) to afford 45 (350 mg, 35%) as a light violet solid. MS (ESI pos. ion) m/z: 334.0; $^1$HNMR (300 MHz, DMSO-$d_6$): δ 10.41 (bs, 1H), 10.21 (s, 1H), 7.99 (d, J=8.4 Hz, 1H), 7.82-7.79 (m, 1H), 7.67-7.55 (m, 3H), 7.42-7.39 (m, 1H), 7.31-7.15 (m, 3H), 6.84 (d, J=7.5 Hz, 1H).

Compound 46: To 10 mL microwave tube were added 45 (100 mg, 0.30 mmol), DMF (3 mL), 9 (118 mg, 0.30 mmol)

and Cs$_2$CO$_3$ (295 mg, 0.90 mmol). The tube and heated to 180° C. for 45 min, then the reaction mixture was diluted with EtOAc (30 mL), filtered and evaporated in vacuo. The residue was purified by silica gel column chromatography (60-120 silica gel) using hexane/ethyl acetate as eluent (70:30) to afford 46 (85 mg, 41%) as a gummy material. MS (ESI pos. ion) m/z: 693.4.

Compound 47: To a stirred solution of 46 (85 mg, 0.12 mmol) in DCM (3 mL) at 0° C. was added TFA (0.3 mL) dropwise. The mixture was stirred for 2 h at room temperature, concentrated in vacuo and purified by prep-HPLC to afford 47 (12 mg, 16%) a brown solid and TFA salt. MS (ESI pos. ion) m/z: 593.3; $^1$H NMR (300 MHz, DMSO-d$_6$): δ 10.7 (s, 1H), 9.02 (s, 1H), 8.69 (bs, 1H), 8.35 (d, J=5.4 Hz, 1H), 8.05 (d, J=8.7 Hz, 1H), 7.96 ((d, J=8.4 Hz, 1H), 7.84-7.83 (m, 1H), 7.71-7.59 (m, 2H), 7.48-7.41 (m, 4H), 7.29-7.26 (m, 2H), 7.11 (d, J=7.5 Hz, 1H), 4.11 (br, 1H), 3.37 (d, J=7.2 Hz, 1H), 3.18 (t, J=9.3 Hz, 1H), 2.93-2.87 (m, 2H), 1.98-1.88 (m, 2H), 1.71-1.57 (m, 2H).

Example 10. Synthesis of (S)—N-(2-chlorobenzyl)-3-(5-(2-(piperidin-3-ylamino)pyrimidin-4-yl)thiazol-4-yloxy)benzamide TFA salt (compound 51 (LBC-372)

Compound 49: to a solution of 48 (500 mg, 3.62 mmol, 1.0 eq.) and 17 (510 mg, 3.62 mmol, 1.0 eq.) in DCM (20 ml) at 25° C. was added EDC:HCL (694 mg, 3.62 mmol, 1.0 eq.). The reaction mixture was stirred at 25° C. for 18 h and then poured into 1N HCL (20 ml) to provide a solid. The solid was filtered, washed with water (20 ml) and dried to give 49 (430 mg, 45%) as a white solid. ms (esi pos. ion) m/z: 262.2; $^1$H-nmr [300 mhz, cdcl$_3$]: δ 9.70 (s, 1h), 8.95 (t, j=5.7 hz, 1h), 7.46-7.42 (m, 1h), 7.32-7.24 (m, 6h), 6.94-6.91 (m, 1h), 4.50 (d, j=5.7 hz, 2h).

Compound 50: To the solution of 49 (100 mg, 0.38 mmol, 1.0 eq.) in DMF (2 mL) was added Cs$_2$CO$_3$ (250 mg, 0.76 mmol, 2.0 eq.) and 9 (143 mg, 0.38 mmol, 1.0 eq.). The reaction mixture was microwaved at 180° C. for 3 h. After 3 h, reaction mixture was poured into ice water (10 mL) to provide a solid. The solid was filtered, washed with water (20 mL) and it was dried to get desired product 4 (crude, 230 mg) as a brown color solid that was taken onto the next step. MS (ESI pos. ion) m/z: 621.5.

Compound 51: To a solution of 50 (230 mg, 0.40 mmol) in DCM (10 mL) at 25° C. was added TFA (0.5 mL). The reaction mixture was stirred for 2 h, concentrated and purified by prep-HPLC to afford 51 (40 mg, 30%) as a brown solid and TFA salt. MS (ESI pos. ion) m/z: 521.4; $^1$H-NMR [500 MHz, DMSO-d$_6$]: δ 9.14 (d, J=4.0 Hz, 2H), 8.54 (brs, 2H), 8.38 (d, J=5.3 Hz, 1H), 7.78 (d, J=8.0 Hz, 1H), 7.64-7.63 (m, 1H), 7.55-7.53 (m, 2H), 7.35-7.31 (m, 5H), 7.23 (d, J=5.3 Hz, 1H), 4.53 (d, J=5.9 Hz, 2H), 2.89-2.84 (m, 2H), 1.98-1.90 (m, 2H), 1.68-1.58 (m, 1H), 1.24 (s, 1H).

Example 11. Synthesis of (S)—N-(2-chlorobenzyl)-N,4-dimethyl-3-(5-(2-(piperidin-3-ylamino) pyrimidin-4-yl)thiazol-4-yloxy)benzamide. TFA salt (compound 55 (LBC-373)

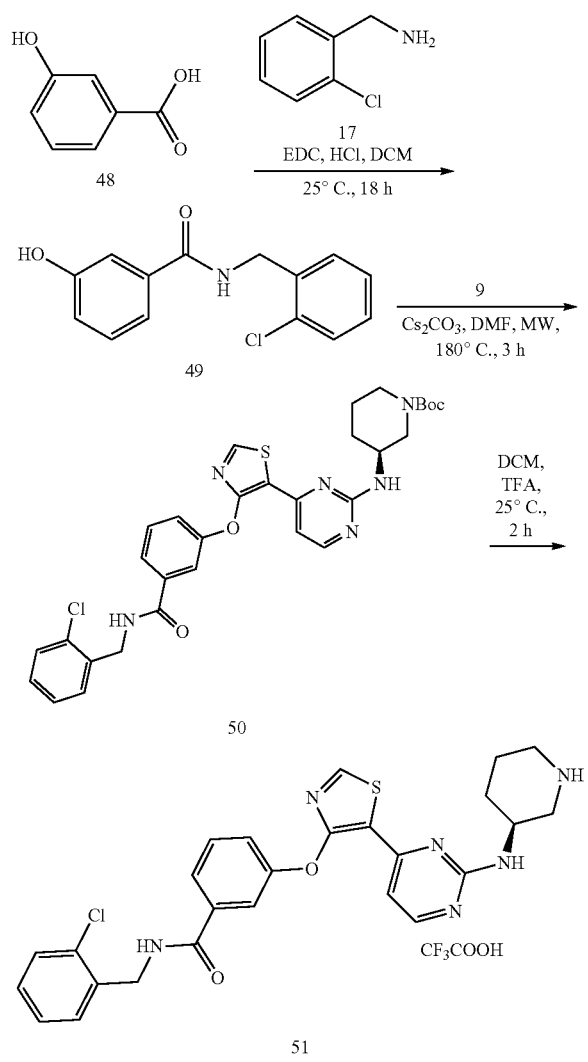

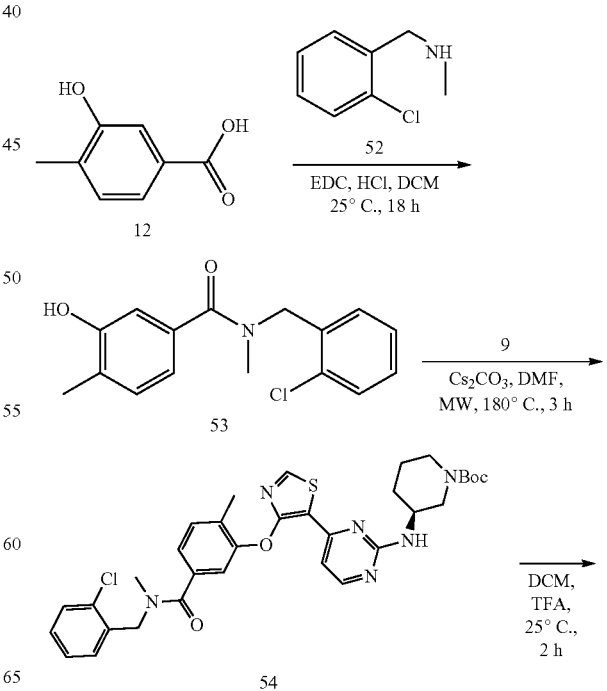

-continued

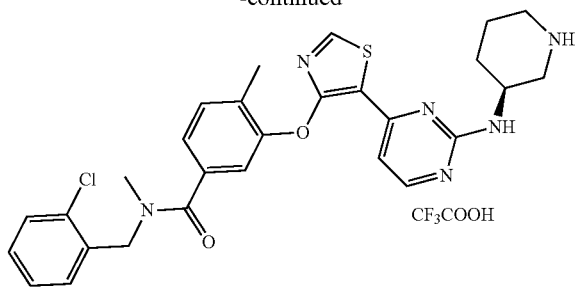

55

CF₃COOH

Compound 53: to the solution of 12 (392 mg, 2.58 mmol, 1.0 eq.) and 52 (400 mg, 2.58 mmol, 1.0 eq.) in dcm (20 ml) was added EDC:HCL (495 mg, 2.58 mmol, 1.0 eq.) at 25° C. The reaction mixture was stirred at 25° C. for 18 h, then poured into 1N HCL (20 ml) to get solid. The solid was filtered, washed with water (20 ml) to give 53 (600 mg, 80%) as a white gel. ms (esi pos. ion) m/z: 290.3; ¹h nmr [300 mhz, cdcl₃]: δ 9.57 (s, 1h), 7.47 (brs, 1h), 7.40-7.30 (m, 3h), 7.11-6.67 (m, 3h), 4.67 (s, 2h), 2.87 (s, 3h), 2.12 (s, 3h).

Compound 54: To a solution of 53 (100 mg, 0.34 mmol, 1.0 eq.) in DMF (3 mL) was added Cs₂CO₃ (225 mg, 0.69 mmol, 2.0 eq.) and 9 (137 mg, 0.34 mmol, 1.0 eq.) at 25° C. The reaction mixture was microwaved at 180° C. for 3 h, then poured into ice water (10 mL) and extracted with ethyl acetate (2×20 mL). The combined organic layers were washed with brine solution (2×20 mL), dried over anhydrous Na₂SO₄, filtered and the solvent was removed in vacuo. The residue was purified by silica gel column chromatography (60-120 silica gel) using hexane/ethyl acetate as eluent (75:25) to afford 54 (90 mg, 40%) as a brown liquid. MS (ESI pos. ion) m/z: 649.5.

Compound 55: To a solution of 54 (100 mg, 0.15 mmol) in DCM (5 mL) was added TFA (0.2 mL) at 25° C. Reaction mixture was stirred for 2 h, concentrated and purified by prep-HPLC to give 55 as a brown solid and TFA salt. MS (ESI pos. ion) m/z: 549.5; ¹H NMR [300 MHz, DMSO-d₆]: δ 9.03-8.93 (m, 1H), 8.67 (brs, 2H), 8.37 (s, 1H), 7.47-7.12 (m, 7H), 6.83 (s, 1H), 4.67-4.63 (m, 1H), 4.50-4.46 (m, 1H), 4.11 (s, 2H), 3.40-3.36 (m, 1H), 3.21-3.17 (m, 1H), 2.87 (s, 3H), 2.26 (s, 3H), 2.06 (s, 2H), 2.00-1.88 (m, 2H), 1.75-1.54 (m, 2H).

Example 12. Synthesis of (S)-2-chloro-N-(4-(2-methyl-5-(2-(piperidin-3-ylamino)pyrimidin-4-yl)thiazol-4-yloxy)naphthalen-1-yl)benzenesulfonamide. TFA salt (compound 67 (LBC-366))

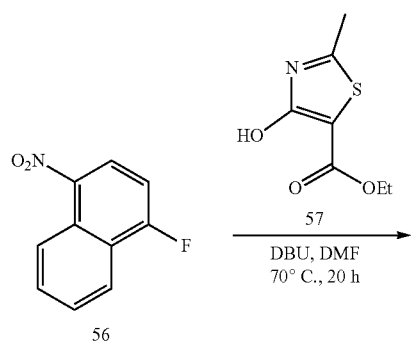

56 → 57
DBU, DMF
70° C., 20 h

-continued

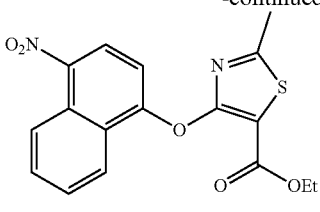

58

NaOH, 1,4-dioxane
H₂O, 25° C., 6 h

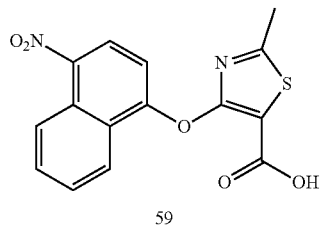

59

N,O-dimethyl hydroxyl amine hydrochloride

EDC, HCl, HOBt, N-methyl morpholine, DCM, 25° C., 18 h

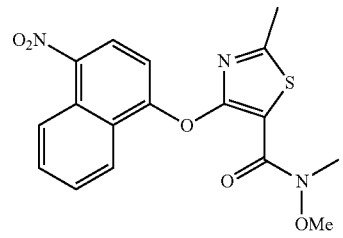

60

Fe, AcOH
25° C., 18 h

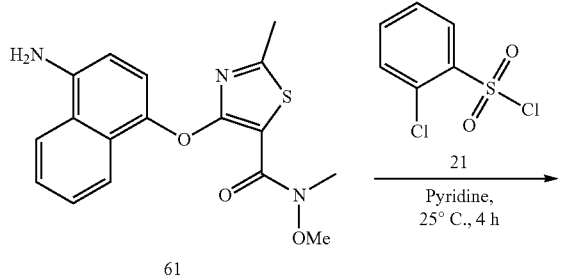

61 + 21
Pyridine, 25° C., 4 h

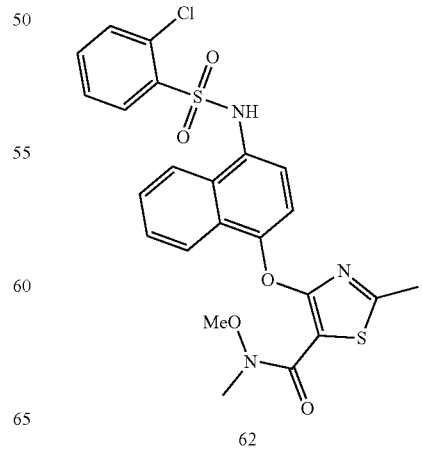

62

CH₃MgI
0° C., 30 min

129

-continued

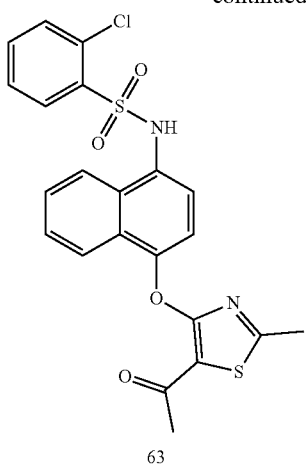

63

Et₃N, DMAP,
(Boc)₂O
───────────→
THF, 25° C., 4 h

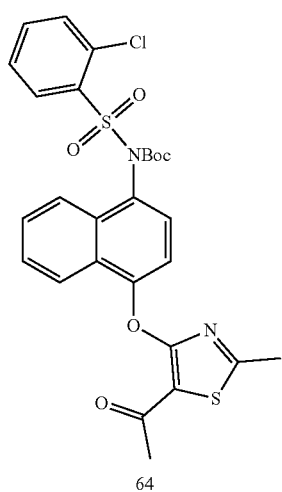

64

DMF-DMA,
60° C., 8 h
───────────→

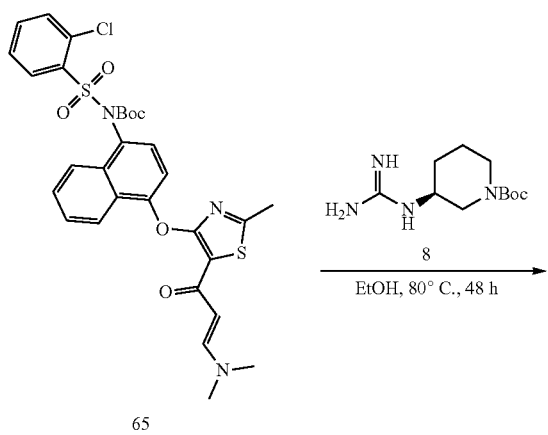

65

130

-continued

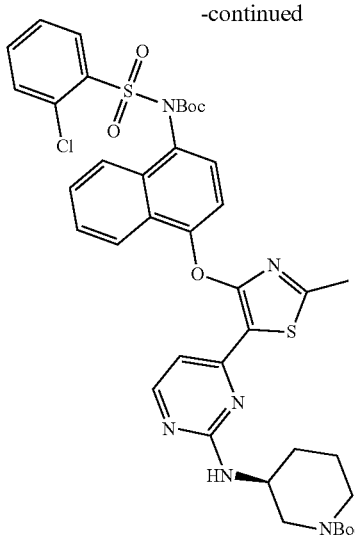

66

DCM,
TFA,
25° C.,
2 h
──────→

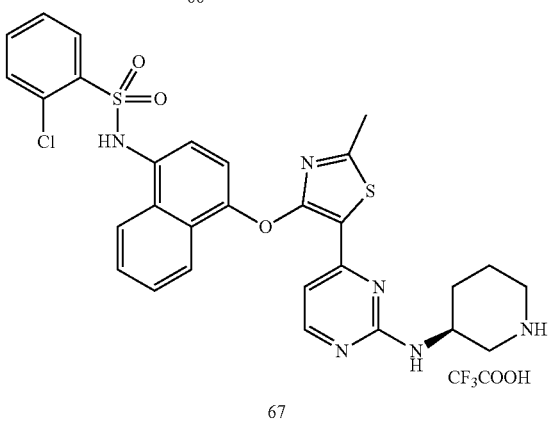

67

Compound 58: To the solution of 56 (1.02 g, 5.34 mmol, 1.0 eq.) in DMF (17 mL) was added DBU (0.8 mL, 5.34 mmol, 1.0 eq.) and 57 (1 g, 5.34 mmol, 1.0 eq.) at 25° C. The reaction mixture was heated at 70° C. for 20 h, then cooled to room temperature and quenched and with ice water. The aqueous layer was extracted with ethyl acetate (3×30 mL) and the combined organic layers were washed with a brine solution (2×30 mL), dried over anhydrous Na₂SO₄, filtered and the solvent was removed in vacuo. The residue was purified by basic silica gel column chromatography (60-120 basic silica gel) using hexane/ethyl acetate as eluent (93:7) to afford 58 (1.27 g, 33%) as a white solid. MS (ESI pos. ion) m/z: 359.2.

Compound 59: To the solution of 58 (1.25 g, 3.49 mmol, 1.0 eq.) in 1,4-dioxane (12 ml) was added sodium hydroxide (349 mg, 8.72 mmol, 2.5 eq.) and water (3.12 ml) at 25° C. The reaction mixture was stirred at 25° C. for 6 h, then concentrated, dissolved in water (50 ml) and acidified with 2N HCL (10 ml). The aqueous layer was extracted with ethyl acetate (3×150 ml). The combined organic layers were washed with a brine solution (2×50 ml), dried over anhydrous Na₂SO₄, filtered and the solvent was removed in vacuo to afford 59 (750 mg, 65%) as a yellow solid. MS (ESI pos. ion) m/z: 331.2.

Compound 60: To the solution of 59 (650 mg, 1.96 mmol, 1.0 eq.) in DCM (5 mL) was added N-methyl morpholine (0.65 mL, 1V), N,O-dimethyl hydroxyl amine hydrochloride (192 mg, 1.96 mmol, 1.0 eq.) and HOBt (266 mg, 1.96 mmol, 1.0 eq.) at 25° C. The reaction mixture was cooled to 0° C., and EDC:HCl (453 mg, 2.36 mmol, 1.2 eq.) was added. The reaction mixture was stirred at 25° C. for 18 h, quenched and with 1N HCl (30 mL) and neutralized with a sat. NaHCO₃ solution (30 mL). The aqueous layer was extracted with EtOAc (3×30 mL) and the combined organic layers were washed with brine solution (2×30 mL), dried over anhydrous Na₂SO₄, filtered and the solvent was removed in vacuo to afford 60 (644 mg, 47%) as a yellow oil.

Compound 61: To the solution of 60 (640 mg, 1.71 mmol, 1.0 eq) in AcOH (6.4 mL) was added Fe powder (325 mg, 5.83 mmol, 3.4 eq.) at 25° C. The reaction mixture was stirred at 25° C. for 18 h, then quenched with water (20 mL) and extracted with ethyl acetate (3×50 mL). The combined organic layers were washed with brine solution (2×20 mL), dried over anhydrous Na₂SO₄, filtered and the solvent was removed in vacuo to afford 61 (550 mg, 93%) as a brown solid. MS (ESI pos. ion) m/z: 344.2.

Compound 62: To a solution of 61 (550 mg, 1.60 mmol, 1.0 eq) in pyridine (5 mL) was added compound 21 (0.22 mL, 1.60 mmol, 1.0 eq) at 25° C. The reaction mixture was stirred at 25° C. for 4 h, concentrated to residue and dissolved in water (20 mL). The aqueous layer was extracted with ethyl acetate (3×30 mL) and the combined organic layers were washed with brine solution (2×30 mL), dried over anhydrous Na₂SO₄, filtered and the solvent was removed in vacuo. The residue was purified by silica gel column chromatography (60-120 silica gel) using hexane/ethyl acetate as eluent (50:50) to afford 62 (650 mg, 78%) as a brown liquid. MS (ESI pos. ion) m/z: 518.2.

Compound 63: To a solution of 62 (650 mg, 1.25 mmol, 1.0 eq.) in THF (10 mL) at 0° C. was added dropwise methyl magnesium iodide (3.0 M in ether, 0.83 mL, 2.50 mmol, 2.0 eq.). The reaction mixture was stirred at 25° C. for 30 min and then quenched with a sat. NH₄Cl solution (15 mL). The organic layer was separated and the aqueous layer was extracted with EtOAc (3×30 mL). The combined organic layers were then washed with a brine solution (2×20 mL), dried over anhydrous Na₂SO₄, filtered and the solvent was removed in vacuo. The residue was purified by silica gel column chromatography (60-120 silica gel) using hexane/ethyl acetate as eluent (60:40) to afford 63 (400 mg, 67%) as a brown solid. MS (ESI pos. ion) m/z: 473.3.

Compound 64: To a solution of 63 (150 mg, 0.31 mmol, 1.0 eq) in THF (10 mL) was added Et₃N (0.05 mL, 0.38 mmol, 1.2 eq.) and (Boc)₂O (0.07 mL, 0.31 mmol, 1.0 eq.), DMAP (8 mg, 0.06 mmol, 0.2 eq.) at 25° C. The reaction mixture was stirred at 25° C. for 4 h and then concentrated to a residue. The residue was purified by silica gel column chromatography (60-120 silica gel) using hexane/ethyl acetate as eluent (85:15) to afford 64 (160 mg, 88%) as a brown solid. MS (ESI pos. ion) m/z: 573.3.

Compound 65: The compound 64 (160 mg, 0.27 mmol, 1.0 eq) was dissolved in DMF-DMA (1 mL) at 25° C. The reaction mixture was stirred at 60° C. for 8 h, then poured into ice water to give a solid. The solid was filtered, washed with water (10 mL) and dried to give 65 (120 mg, 68%) as a yellow solid. MS (ESI pos. ion) m/z: 628.4.

Compound 66: a solution of 65 (106 mg, 0.38 mmol, 2.0 eq.) in EtOH (10 mL) was added K₂CO₃ (158 mg, 1.14 mmol, 6.0 eq.) and 8 (120 mg, 0.19 mmol, 1.0 eq.) at 25° C. The reaction mixture was stirred at 80° C. for 48 h, then cooled to room temperature and filtered. The solvent was concentrated, and the residue was purified by silica gel column chromatography (60-120 silica gel) using hexane/acetone as eluent (80:20) to afford 66 (70 mg, 51%) as a yellow solid. MS (ESI pos. ion) m/z: 707.4.

Compound 67: To a solution of compound 66 (70 mg, 0.09 mmol) in DCM (5 mL) was added TFA (0.3 mL) at 25° C. The reaction mixture was stirred for 2 h, concentrated and then purified by prep-HPLC to afford 67 (20 mg, 33%) as a yellow solid. MS (ESI pos. ion) m/z: 607.4; ¹H NMR [300 MHz, DMSO-d₆]: δ 10.52 (s, 1H), 8.64 (brs, 1H), 8.29 (d, J=5.1 Hz, 1H), 8.20-8.17 (m, 1H), 8.08-8.05 (m, 1H), 7.82 (dd, J=7.8.0, 1.2 Hz, 1H), 7.70-7.68 (m, 1H), 7.63-7.58 (m, 3H), 7.42 (t, J=7.2 Hz, 1H), 7.19-7.11 (m, 2H), 7.02 (d, J=8.1 Hz, 1H), 4.13-4.08 (m, 1H), 3.36 (d, J=11.1 Hz, 1H), 3.20 (d, J=10.5 Hz, 1H), 2.88-2.53 (m, 2H), 2.54 (s, 3H), 1.96-1.88 (m, 2H), 1.75-1.57 (m, 2H).

Example 13. Synthesis of (S)-1-(2-chlorophenyl)-N-(2-fluoro-4-(3-(2-(piperidin-3-ylamino)pyrimidin-4-yl)pyrazin-2-yloxy)phenyl) methane sulfonamide. TFA salt (compound 73 (LBC-363)

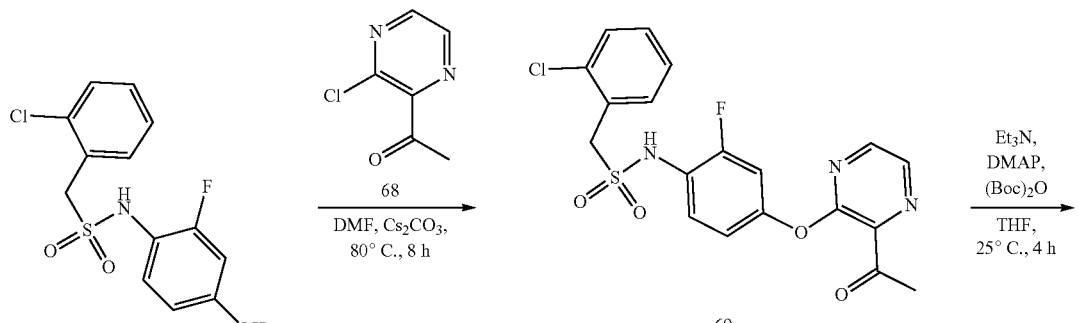

-continued

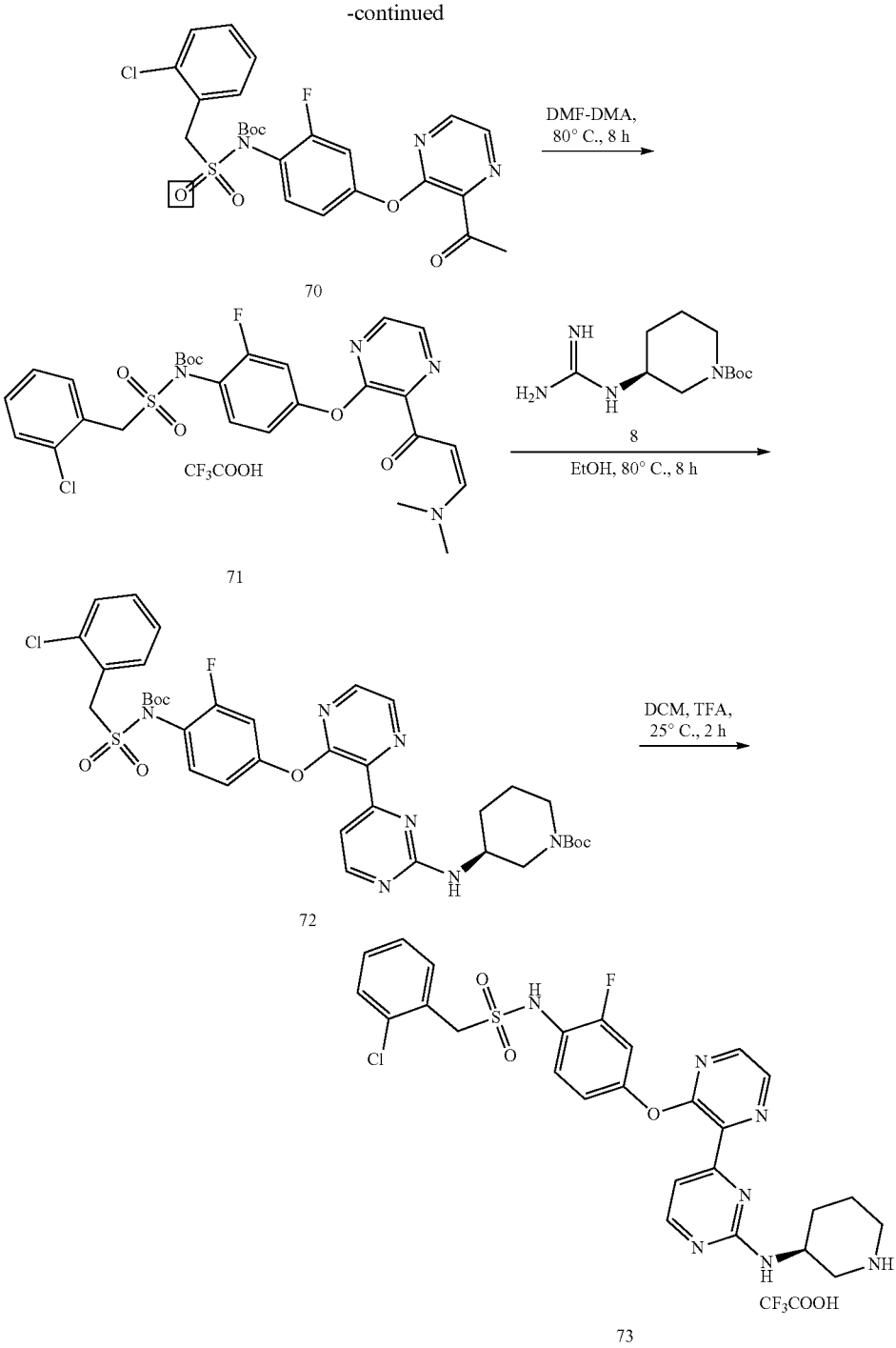

Compound 69: To a solution of 3 (180 mg, 0.57 mmol, 1.0 eq) in DMF (3 mL) was added Cs$_2$CO$_3$ (372 mg, 01.14 mmol, 2.0 eq) and 68 (89 mg, 0.57 mmol, 1.0 eq) at 25° C. The reaction mixture was heated at 80° C. for 8 h, then cooled to room temperature and quenched and with ice water (15 mL). The aqueous layer was extracted with EtOAc (3×15 mL), and the combined organic layers were washed with a brine solution (2×20 mL), dried over anhydrous Na$_2$SO$_4$, filtered and the solvent was removed in vacuo. The residue was purified by silica gel column chromatography (60-120 silica gel) using hexane/ethyl acetate as eluent (80.20) to give 69 (170 mg, 71%) as a pale yellow solid. MS (ESI pos. ion) m/z: 436.3.

Compound 70: To the solution of 69 (170 mg, 0.39 mmol, 1.0 eq) in THF (15 mL) was added Et$_3$N (0.06 mL, 0.46 mmol, 1.2 eq.), (Boc)$_2$O (0.09 mL, 0.39 mmol, 1.0 eq.) and DMAP (2.4 mg, 0.019 mmol, 0.2 eq.) at 25° C. Then the reaction mixture was stirred at 25° C. for 4 h and concentrated to residue. The residue was purified by silica gel column chromatography (60-120 silica gel) using hexane/ ethyl acetate as eluent (80:20) to give 70 (160 mg, 76%) as a white solid. MS (ESI pos. ion) m/z: 536.4.

Compound 71: The compound 70 (160 mg, 0.29 mmol, 1.0 eq) was dissolved in DMF-DMA (3 mL) at 25° C. The reaction mixture was stirred at 80° C. for 8 h, quenched with ice water (10 mL) and extracted with EtOAc (3×20 mL). The combined organic layers were washed with a brine solution (2×10 mL), dried over anhydrous $Na_2SO_4$, filtered and the solvent was removed in vacuo to give 71 (120 mg, 68%) as a yellow solid. MS (ESI pos. ion) m/z: 591.4.

Compound 72: To a solution of 71 (70 mg, 0.25 mmol, 2.0 eq.) in EtOH (5 mL) was added $K_2CO_3$ (104 mg, 0.75 mmol, 6.0 eq.) and 8 (120 mg, 0.12 mmol, 1.0 eq.) at 25° C. Then the reaction mixture was stirred at 80° C. for 8 h, cooled to room temperature and filtered. The solvent was concentrated to residue and the residue was purified by silica gel column chromatography (60-120 silica gel) using DCM/MeOH as eluent (98:2) to afford 72 (40 mg, 44%) as a yellow solid. MS (ESI pos. ion) m/z: 770.5.

Compound 73: To a solution of 72 (40 mg, 0.05 mmol) in DCM (5 mL) was added TFA (0.2 mL) at 25° C. Reaction mixture was stirred for 2 h, concentrated and purified by prep-HPLC to afford 73 (12 mg, 68%) as a green gel and TFA salt. MS (ESI pos. ion) m/z: 570.4; $^1$H NMR [300 MHz, DMSO-$d_6$]: δ 9.89 (s, 1H), 8.63 (brs, 2H), 8.53 (d, J=2.4 Hz, 1H), 8.51 (d, J=5.1 Hz, 1H), 8.35 (d, J=2.4 Hz, 1H), 7.55-7.49 (m, 3H), 7.41-7.37 (m, 3H), 7.30 (dd, J=11.1, 2.4 Hz, 1H), 7.21 (d, J=4.8 Hz, 1H), 7.03 (dd, J=8.4, 1.5 Hz, 1H), 4.67 (s, 2H), 4.13-4.09 (m, 1H), 3.17-3.13 (m, 2H), 2.89-2.83 (m, 2H), 1.98-1.93 (m, 2H), 1.58-1.54 (m, 2H).

Example 14. Synthesis of (S)-2-chloro-N-(2-fluoro-4-(3-(2-(piperidin-3-ylamino)pyrimidin-4-yl)pyrazin-2-yloxy)phenyl)benzenesulfonamide TFA salt (compound 77 (LBC-349)

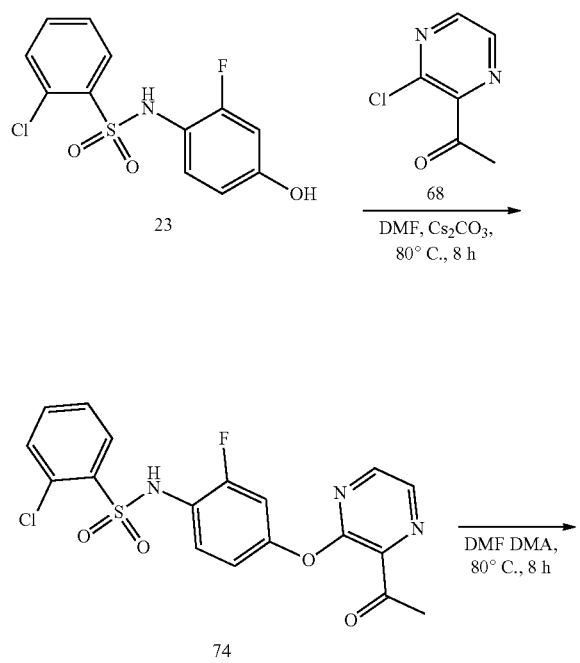

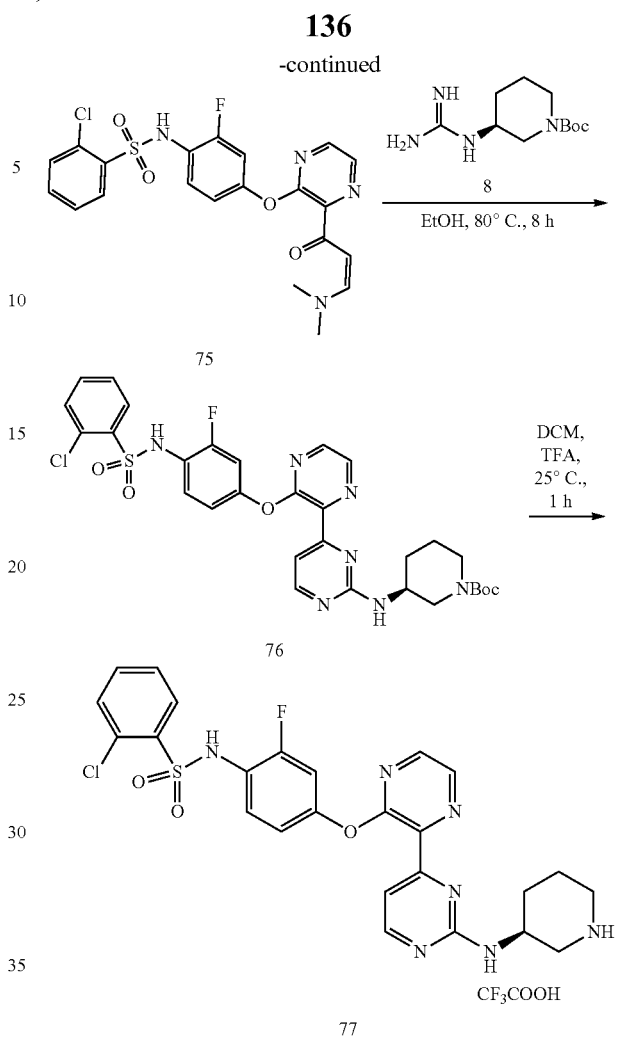

Compound 74: To the solution of 23 (100 mg, 0.33 mmol, 1.0 eq) in DMF (3 mL) was added $Cs_2CO_3$ (21.7 mg, 0.66 mmol, 2.0 eq) and 68 (52 mg, 0.33 mmol, 1.0 eq) at 25° C. The reaction mixture was stirred at 80° C. for 8 h, cooled to room temperature and quenched and with ice water (10 mL). The aqueous layer was extracted with ethyl acetate (3×15 mL) and the combined organic layers were washed with brine solution (2×20 mL), dried over anhydrous $Na_2SO_4$ and filtered. The solvent was removed in vacuo, and the residue was purified by silica gel column chromatography (60-120 silica gel) using hexane/ethyl acetate as eluent (80:20) to give 74 (100 mg, 71%) as a brown solid. MS (ESI pos. ion) m/z: 422.2; $^1$H-NMR [500 MHz, $CDCl_3$]: δ 8.36 (d, J=2.5 Hz, 1H), 8.20 (d, J=2.5 Hz, 1H), 8.01 (dd, J=8.0, 1.5 Hz, 1H), 7.59-7.50 (m, 3H), 7.37-7.36 (m, 1H), 7.23 (s, 1H), 6.88-6.86 (m, 2H), 2.72 (s, 3H).

Compound 75: Compound 74 (100 mg, 0.23 mmol, 1.0 eq) was dissolved in DMF-DMA (2 mL) at 25° C. The reaction mixture was stirred at 80° C. for 8 h, quenched with ice water (10 mL) and extracted with EtOAc (3×10 mL). The combined organic layers were washed with a brine solution (2×10 mL), dried over anhydrous $Na_2SO_4$, filtered and the solvent was removed in vacuo_to give 75 (50 mg, 44%) as a yellow solid. MS (ESI pos. ion) m/z: 477.3.

Compound 76: To a solution of 75 (58 mg, 0.21 mmol, 2.0 eq.) in EtOH (3 mL) was added $K_2CO_3$ (87 mg, 0.63 mmol, 6.0 eq.) and 8 (50 mg, 0.10 mmol, 1.0 eq.) at 25° C. The reaction mixture was stirred at 80° C. for 8 h, cooled to room temperature and filtered. The solvent was concentrated to a residue that was purified by silica gel column chromatography (60-120 silica gel) using DCM/MeOH as eluent (98:2) to give 76 (35 mg, 51%) as a pale yellow solid. MS (ESI pos. ion) m/z: 656.4.

Compound 77: To a solution of 76 (35 mg, 0.05 mmol) in DCM (3 mL) was added TFA (0.3 mL) at 25° C. Reaction mixture was stirred for 2 h, concentrated and purified by prep-HPLC to give 77 (20 mg, 68%) as a green gel and TFA salt. MS (ESI pos. ion) m/z: 556.4; $^1$H-NMR [300 MHz, DMSO-$d_6$]: δ 10.38 (s, 1H), 8.59 (brs, 2H), 8.53 (d, J=2.7 Hz, 1H), 8.48 (d, J=5.1 Hz, 1H), 7.89 (dd, J=7.8, 1.2 Hz, 1H), 7.72-7.63 (m, 2H), 7.53-7.47 (m, 2H), 7.27-7.16 (m, 3H), 6.98 (d, J=7.8 Hz, 1H), 4.09 (brs, 1H), 3.39-3.27 (m, 2H), 3.14-3.09 (m, 1H), 2.88-2.84 (m, 2H), 1.94-1.80 (m, 2H), 1.61-1.52 (m, 2H).

Example 15. Synthesis of (S)-2-chloro-N-(4-(3-(2-(piperidin-3-ylamino) pyrimidin-4-yl)pyrazin-2-yloxy)naphthalen-1-yl)benzenesulfonamide TFA salt (compound 84 (LBC-361)

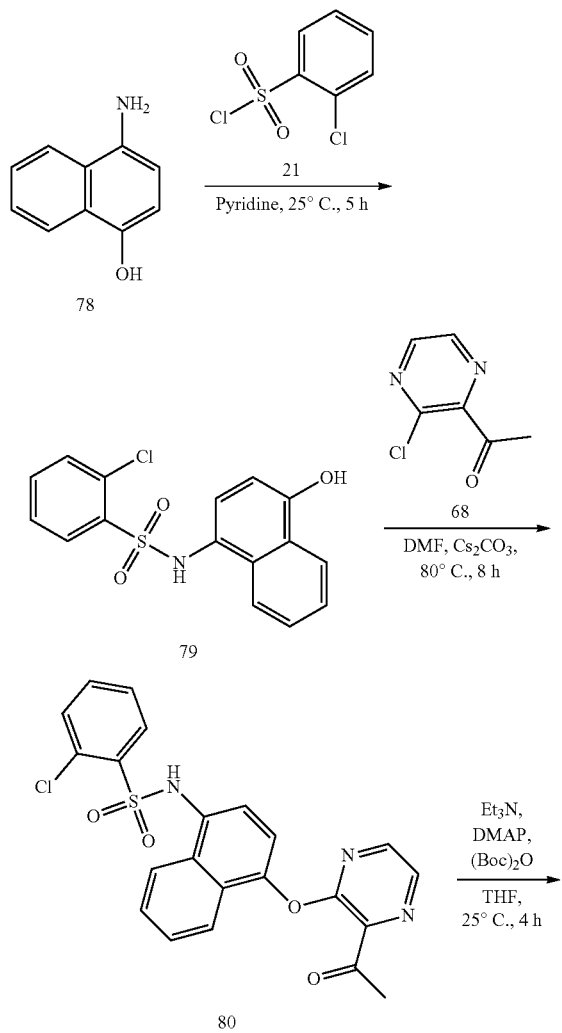

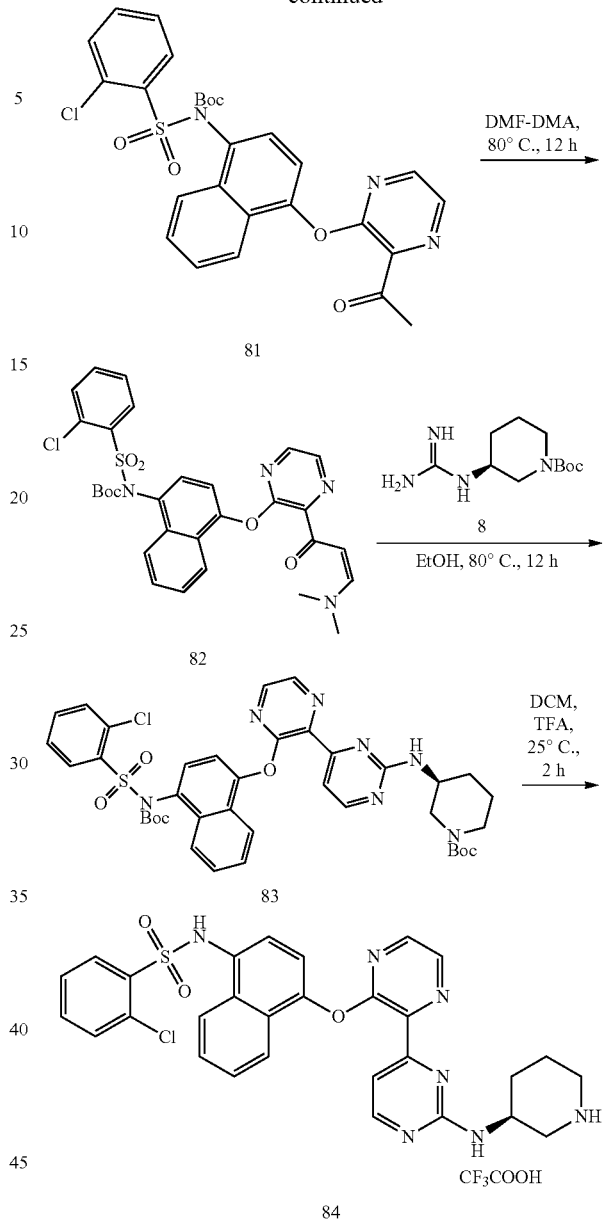

Compound 79: To the solution of 78 (500 mg, 2.55 mmol, 1.0 eq) in pyridine (5 mL) was added 21 (0.36 mL, 2.55 mmol, 1.0 eq) at 25° C. The reaction mixture was stirred at 25° C. for 5 h, concentrated to a residue and dissolved in water (3×30 mL). The aqueous layer was extracted with EtOAc (3×30 mL), and the combined organic layers were washed with a brine solution (2×30 mL), dried over anhydrous $Na_2SO_4$, filtered and the solvent was removed in vacuo. The residue was purified by silica gel column chromatography (60-120 silica gel) using hexane/ethyl acetate as eluent (80:20) to give 79 (400 mg, 47%) as a solid. MS (ESI neg. ion) m/z: 332.1; $^1$H NMR [500 MHz, DMSO-$d_6$]: δ 10.29 (s, 1H), 10.06 (s, 1H), 8.07 (d, J=7.5 Hz, 1H), 8.03 (d, J=8.0 Hz, 1H), 7.72-7.67 (m, 2H), 7.59 (td, J=7.8, 1.4 Hz, 1H), 7.46-7.40 (m, 2H), 7.38-7.35 (m, 1H), 6.89 (d, J=8.1 Hz, 1H), 6.68 (d, J=8.1 Hz, 1H).

Compound 80: To a solution of 79 (200 mg, 0.60 mmol, 1.0 eq.) in DMF (5 mL) was added $Cs_2CO_3$ (391 mg, 1.20 mmol, 2.0 eq.) followed by 68 (94 mg, 0.60 mmol, 1.0 eq.) at 25° C. The reaction mixture was stirred at 80° C. for 8 h, cooled to room temperature and quenched and with ice water. The aqueous layer was extracted with EtOAc (3×15 mL), and the combined organic layers washed with brine solution (2×20 mL), dried over anhydrous Na₂SO₄, filtered and the solvent was removed in vacuo. The residue was purified by silica gel column chromatography (60-120 silica gel) using hexane/ethyl acetate as eluent (75:25) to afford 80 (100 mg, 37%) as a brown solid. MS (ESI pos. ion) m/z: 454.3.

Compound 81: To the solution of 80 (45 mg, 0.09 mmol, 1.0 eq) in THF (5 mL) was added Et₃N (0.016 mL, 0.11 mmol, 1.2 eq.) and (Boc)₂O (0.023 mL, 0.09 mmol, 1.0 eq.), DMAP (2.4 mg, 0.019 mmol, 0.2 eq.) at 25° C. Then the reaction mixture was stirred at 25° C. for 4 h, then concentrated to residue. The residue was purified by silica gel column chromatography (60-120 silica gel) using hexane/ethyl acetate as eluent (85:15) to afford 81 (54 mg, 98) as a brown solid. MS (ESI pos. ion) m/z: 554.4.

Compound 82: The compound 81 (54 mg, 0.09 mmol, 1.0 eq) was dissolved in DMF-DMA (1 mL) at 25° C. and stirred at 80° C. for 12 h. The mixture was then poured into ice water to obtain a solid. The solid was filtered, washed with water (5 mL) and dried to give 82 (50 mg, 84%) as a yellow solid. MS (ESI pos. ion) m/z: 609.4.

Compound 83: To a solution of 82 (46 mg, 0.16 mmol, 2.0 eq.) in EtOH (5 mL) was added K₂CO₃ (68 mg, 0.49 mmol, 6.0 eq.) and 8 (50 mg, 0.08 mmol, 1.0 eq.) at 25° C. The reaction mixture was stirred at 80° C. for 12 h, cooled to room temperature and filtered. The solvent was concentrated to residue that was purified by silica gel column chromatography (60-120 silica gel) using DCM/MeOH as eluent (98:2) to afford 83 (35 mg, 53%) as a brown solid. MS (ESI pos. ion) m/z: 788.6.

Compound 84: To a solution of 83 (35 mg, 0.04 mmol) in DCM (5 mL) was added TFA (0.3 mL) at 25° C. Reaction mixture was stirred for 2 h, concentrated and purified by prep-HPLC to afford 84 (15 mg, 57%) as a yellow solid. MS (ESI pos. ion) m/z: 588.6; ¹H NMR [300 MHz, DMSO-d₆]: δ 10.59 (s, 1H), 8.59 (brs, 1H), 8.53 (d, J=4.8 Hz, 1H), 8.50 (d, J=2.4 Hz, 1H), 8.22 (s, 1H), 8.20 (d, J=2.4 Hz, 1H), 7.85-7.82 (m, 2H), 7.71-7.41 (m, 5H), 7.29-7.18 (m, 3H), 4.15-4.11 (m, 1H), 3.34-3.29 (m, 1H), 3.17-3.13 (m, 1H), 2.86-2.81 (m, 2H), 1.93-1.89 (m, 2H), 1.57-1.52 (m, 2H).

Example 16. Synthesis of (S)-4-(3-(4-((1H-benzo[d]imidazol-2-yl)methyl)phenoxy)pyrazin-2-yl)-N-(piperidin-3-yl)pyrimidin-2-amine TFA salt (compound 47 (LBC-348))

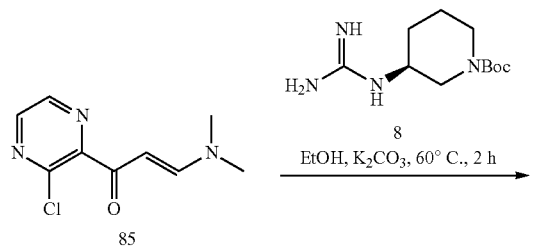

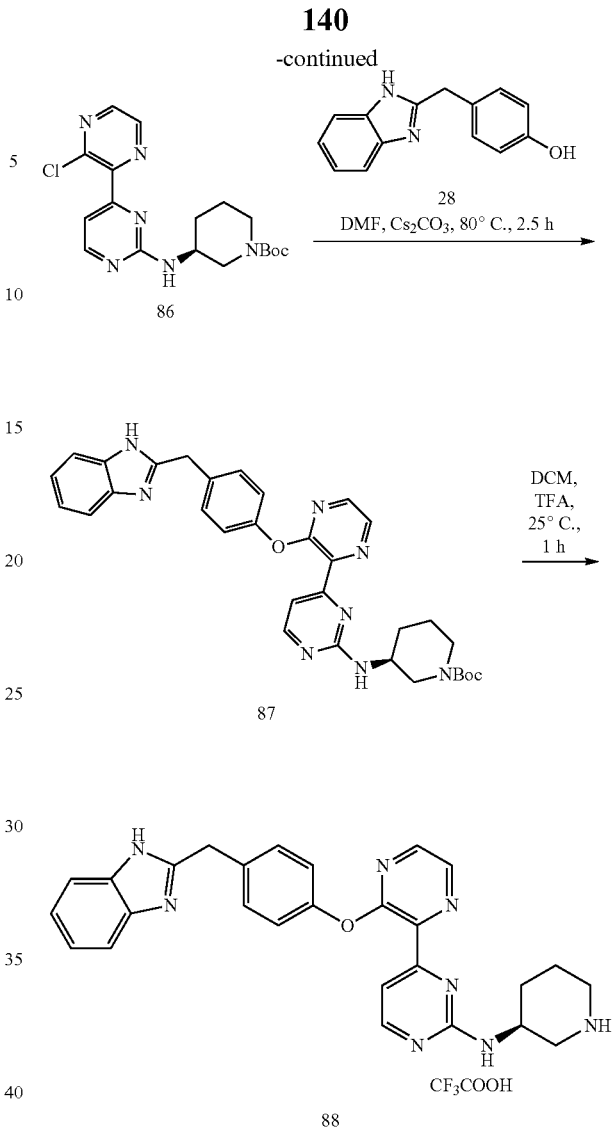

Compound 86: To a stirred solution of 85 (100 mg, 0.473 mmol) in EtOH (2 mL) was added K₂CO₃ (130 mg, 0.947 mmol, 1.0 eq) and compound 8 (114 mg, 0.473 mmol, 1.0 eq) at room temperature. The reaction mixture was heated at 60° C. for 2 h, cooled to room temperature and concentrated. The residue was purified by silica gel column chromatography (60-120 silica gel) using hexane/ethyl acetate as eluent (85:15) to afford 86 (75 mg, 46%) as a pale yellow semi-solid. MS (ESI pos. ion) m/z: 391.4.

Compound 87: To a stirred solution of 86 (50 mg, 0.1282 mmol, 1 eq) in DMF (5 mL) was added Cs₂CO₃ (83.3 mg, 0.256 mmol, 2 eq) and 28 (28 mg, 0.1282 mmol, 1.0 eq) and the reaction mixture was heated to 80° C. for 2.5 h. The mixture was cooled to room temperature, concentrated and purified by silica gel column chromatography (60-120 silica gel) using DCM/Methanol as eluent (99:1) to give 87 (90 mg) of a yellow liquid that was taken to the next step without purification. MS (ESI pos. ion) m/z: 579.5.

Compound 88: To a stirred solution of 87 (100 mg, 0.173 mmol) in DCM (4 mL) was added TFA (0.5 mL) dropwise at 25° C. After stirring for 0.5 h the reaction mixture was concentrated and the residue was purified by prep-HPLC to afford the 88 (21 mg, 25%) as a light yellow solid. MS (ESI pos. ion) m/z: 479.5.

Example 17. Synthesis of (S)-2-chloro-N-(6-methyl-5-((3-2-(piperidin-3-ylamino)pyrimidin-4-yl)pyrazine-2-yl)oxy)naphthalen-1-yl)benzenesulfonamide (compound 96 (LBC-292)
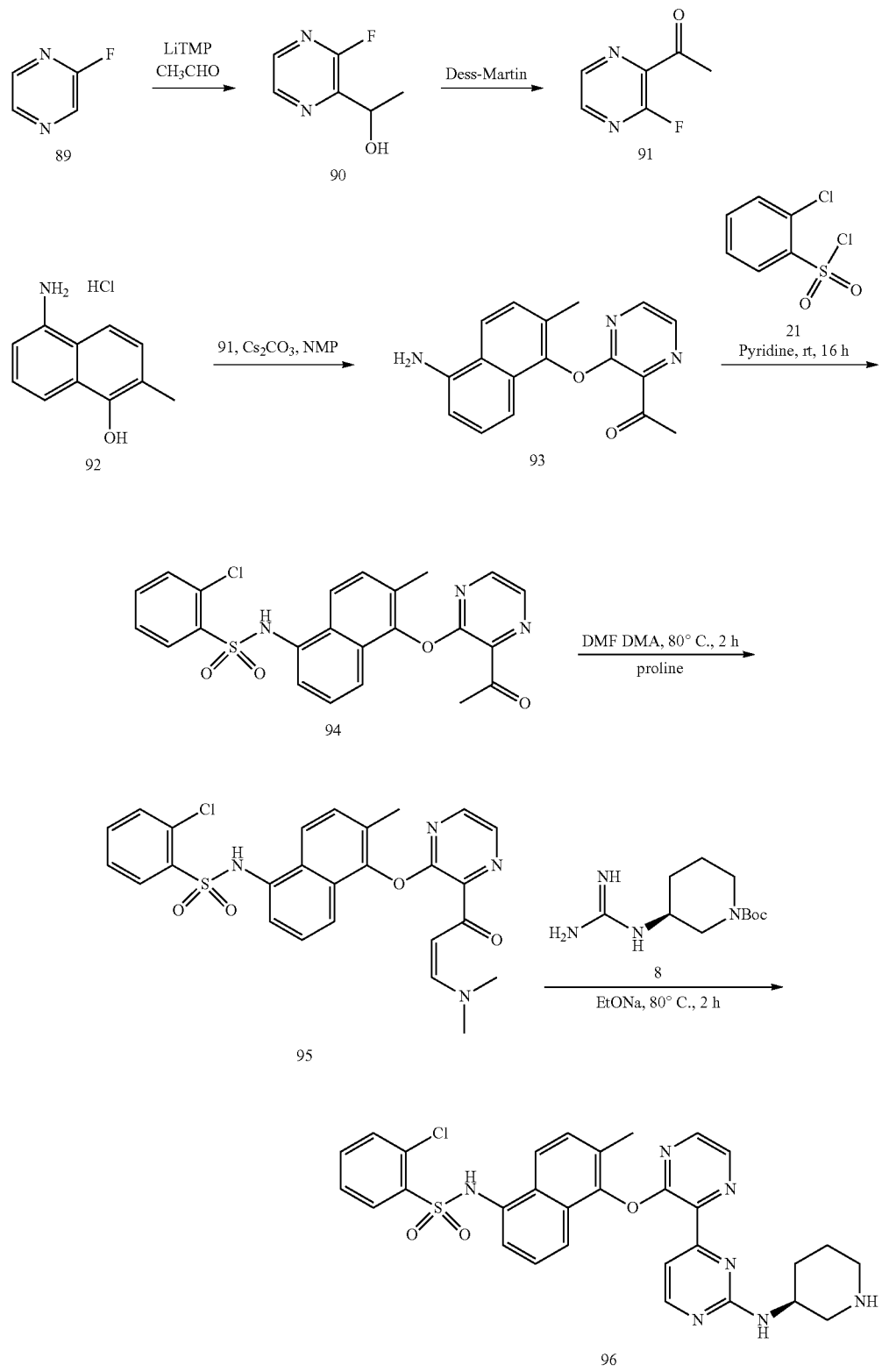

Compound 90: n-BuLi (2.4M, 25.5 mL, 2.2 mol) was added to a solution of TMPA (11 ml) in THF (100 ml) at −50° C. under nitrogen and the mixture was stirred at 0° C. for 20 min. A solution of 89 (4.0 g, 40.8 mmol) in THF (30 ml) was added dropwise at −78° C. and the mixture was stirred for 5 min. A solution of acetaldehyde (22.92 ml) in THF (20 ml) was added at −78° C. and the reaction mixture was stirred for 1 h at −78° C. Water was added to quench the reaction and then EtOAc (100 m L×2) was added. The organic layer was separated, washed with brine, dried over anhydrous Na$_2$SO$_4$ and concentrated. The residue was purified by flash column chromatography on silica gel (petroleum ether/EtOAc=10:1) to give 90 (2.56 g, 44% yield) as a pale yellow oil.

Compound 91: Dess-Martin reagent (9.17 g, 21.6 mmol) was added to a solution of 90 (2.56 g, 18 mmol) in DCM (50 mL) and the reaction mixture was stirred at room temperature for 2 h. Saturated aqueous Na$_2$S$_2$O$_3$ was added followed by addition of saturated aqueous NaHCO$_3$. The mixture was stirred for 30 min and then extracted with EtOAc (100 mL×3). The combined organic layers were washed with brine, dried over anhydrous Na$_2$SO$_4$ and concentrated to afford 92 (2.0 g, 79% yield).

Compound 93: A mixture of 92 (1.3 g, 9.28 mmol), 91 (1.94 g, 9.28 mmol) and cesium carbonate (6.35 g, 19.5 mmol) in NMP (20 mL) was heated at 120° C. for 90 min. The mixture was cooled to room temperature and then extracted with EtOAc (100 mL×2). The combined extracts were washed with water (150 mL) and brine (100 mL), dried over anhydrous MgSO4 and concentrated. The residue was purified by silica gel column chromatography (hexane/EtOAc=1:1) to afford 93 (1.05 g, 33% yield) as a tan solid.

Compound 94: A mixture of 93 (0.9 g, 3.07 mmol) and 21 (0.84 g, 3.99 mmol) in pyridine (20 mL) was stirred under nitrogen at room temperature for 16 h. The mixture was concentrated and diluted with EtOAc (50 mL×2). The organic solution was washed with brine (200 mL), dried over anhydrous MgSO4 and concentrated. The residue was purified by silica gel column chromatography (hexane/EtOAc=7:3 to 3:7) to afford 94 (1.39 g, 97%) as an off-white solid.

Compound 95: A mixture of 94 (1.39 g, 2.97 mmol), DMF-DMA (0.43 g, 3.56 mmol) and L-proline (34.2 mg, 0.297 mmol) was heated at 80° C. for 2 h. The mixture was cooled to room temperature and EtOAc (20 mL) was added. The resulting precipitate was collected by filtration to afford 95 (1.2 g, 77% yield) as a tan amorphous solid.

Compound 96: Compound 95 (522 mg, 1 mmol) was added to a solution of NaOEt (1.5 mmol) in ethanol (10 mL) at room temperature and the mixture was stirred for 5 min. Compound 8 (363 mg, 1.5 mmol) was added and the reaction mixture was heated at 80° C. for 2 h. Water (40 ml) was added, and the resulting mixture was extracted with DCM (20 mL×3). The combined organic layers were washed with brine, dried over anhydrous Na$_2$SO$_4$ and concentrated. The residue was purified by flash column chromatography on silica gel (DCM/MeOH=50:1) to afford 96 (69 mg, 11% yield) as a pale yellow solid. MS (ESI): m/z 602.4 [M+H]+; $^1$H NMR (400 MHz, DMSO-d6): δ 8.54 (d, J=4.8 Hz, 1H), 8.43 (d, J=2.8 Hz, 1H), 8.29 (d, J=4.8 Hz, 1H), 8.12 (d, J=2.8 Hz, 1H), 7.91 (d, J=7.2 Hz, 1H), 7.51 (d, J=7.2 Hz, 1H), 7.47 (d, J=7.2 Hz, 1H), 7.29-7.43 (m, 4H), 7.02-7.07 (m, 3H), 4.11 (br s, 1H), 3.35 (d, J=9.9 Hz, 1H), 3.02 (m, 1H), 2.67-2.77 (m, 2H), 2.17 (s, 3H), 1.99-2.09 (m, 1H), 1.54 (m, 1H), 1.23 (m, 2H).

Example 18. Synthesis of (S)-2-chloro-N-(5-((5-(2-((5,5-difluoropiperidin-3-yl) amino) pyrimidin-4-yl) thiazol-4-yl) oxy) naphthalen-1-yl) benzene sulfonamide (111), and N-(5-((5-(2-((1,4-oxazepan-6-yl) amino) pyrimidin-4-yl) thiazol-4-yl) oxy) naphthalen-1-yl)-2-chlorobenzenesulfonamide (112)

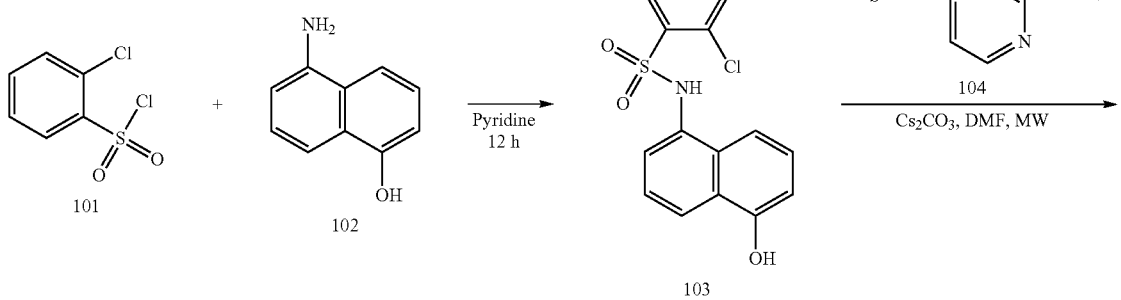

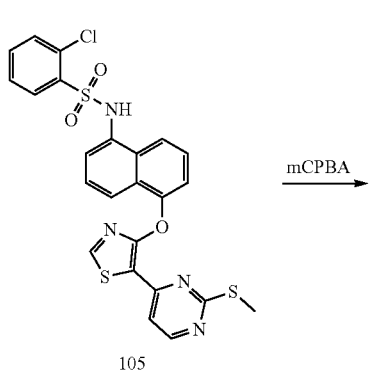
105

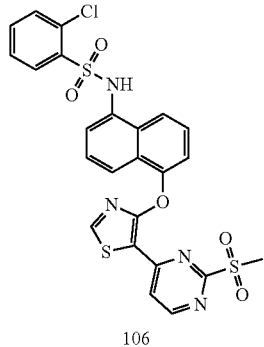
106

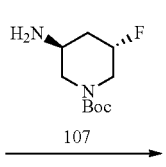
107

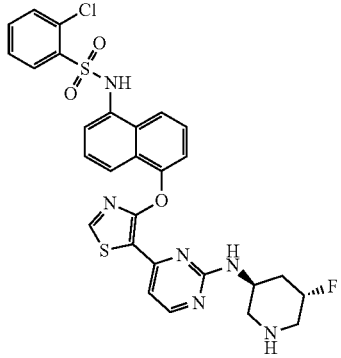
110

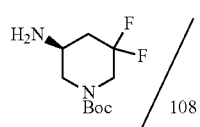
108

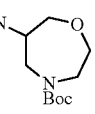
109

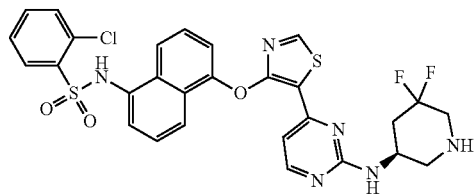
111

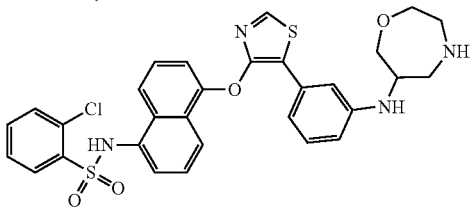
112

2-chloro-N-(5-hydroxynaphthalen-1-yl) benzene sulfonamide (compound 103): To a stirred solution of 102 (5.0 g, 31 mmol) in pyridine (50 mL) was added 2-chlorobenzene-1-sulfonyl chloride 101 (5.0 mL, 38 mmol) at room temperature. The reaction mixture was stirred for 12 h, quenched with 2N HCl (100 mL) and extracted with EtOAc (500 mL). The combined organic layer was washed with brine solution (100 mL), dried over anhydrous Na$_2$SO$_4$, filtered and the solvent was removed in vacuum. The residue was purified through silica gel column chromatography (60-120 silica gel) using hexane/ethyl acetate as eluent (75:25) to afford 103 as a tan colored solid.

% Yield: 3 g (48.3%); Mass [m/z]: 334.1 [M+H]$^+$; TLC Rf EtOAc/Hexane [20:80]=0.5; $^1$H NMR (400 MHz, DMSO-d6): δ 10.41 (bs, 1H), 10.21 (s, 1H), 7.99 (d, J=8.4 Hz, 1H), 7.82-7.79 (m, 1H), 7.67-7.55 (m, 3H), 7.42-7.39 (m, 1H), 7.31-7.15 (m, 3H), 6.84 (d, J=7.5 Hz, 1H).

2-chloro-N-(5-((5-(2-(methylthio) pyrimidin-4-yl) thiazol-4-yl) oxy) naphthalen-1-yl) benzene sulfonamide (compound 105): A mixture of 103 (1.4 g, 4.1 mmol), 104 (500 mg, 2.1 mmol) and Cs$_2$CO$_3$ (2.0 g, 6.18 mol) in N-Methyl pyrrolidinone (15 mL) was degassed, backfilled with nitrogen and heated to 120° C. for 6 h. Then the reaction mixture was cooled to room temperature, diluted with ethyl acetate, washed with water and brine solution and dried over Na$_2$SO$_4$. The residue was purified by column chromatography (silica gel, 0-50% Ethyl acetate in hexane) to afford 105 as a yellow solid. % Yield: 170 mg (15%); Mass (m/z): 541.2 (M+H)+; TLC Rf: EtOAc/Hexane [30:70]=0.3; $^1$H NMR (400 MHz, CDCl$_3$): δ 8.6 (s, 1H), 8.45 (d, J=5.2 Hz, 1H), 7.99 (d, J=8.4 Hz, 1H), 7.82-7.79 (m, 1H), 7.67-7.55 (m, 3H), 7.42-7.39 (m, 1H), 7.31-7.15 (m, 3H), 6.84 (d, J=7.5 Hz, 1H), 2.6 (s, 3H).

2-chloro-N-(5-((5-(2-(methyl sulfonyl) pyrimidin-4-yl) thiazol-4-yl) oxy) naphthalen-1-yl) benzene sulfonamide (106): To a stirred solution of 105 (170 mg, 0.31 mmol) in DCM (5 mL) under nitrogen was added mCPBA (81 mg, 0.47 mmol) at 0° C. After being stirred for another 1 h (0° C.-RT) the reaction mixture was quenched with 2N Na$_2$CO$_3$, extracted with DCM and concentrated. The residue was purified by column chromatography (silica gel, 10-50% Ethyl acetate in Hexane) to afford the 106 as yellow solid. % of Yield: 80 mg (44.4%); Mass (m/z): 573.1 (M+H)+; TLC Rf: Ethyl acetate:Hexane (50:50)=0.2; $^1$H NMR (400 MHz, CDCl$_3$): 8.6 (s, 1H), 8.45 (d, J=5.2 Hz, 1H), 7.99 (d, J=8.4 Hz, 1H), 7.82-7.79 (m, 1H), 7.67-7.55 (m, 3H), 7.42-7.39 (m, 1H), 7.31-7.15 (m, 3H), 6.84 (d, J=7.5 Hz, 1H), 2.04 (s, 3H).

2-chloro-N-(5-((5-(2-(((3S,5R)-5-fluoropiperidin-3-yl) amino) pyrimidin-4-yl) thiazol-4-yl) oxy) naphthalen-1-yl) benzene sulfonamide (110): A mixture of 106 (75 mg, 0.13 mmol), 7 (85.4 mg, 0.39 mmol) and TEA (1 mL) in 1,4-dioxane (2 mL) was degassed and backfilled with nitrogen. The reaction was heated to 100° C. for 72 h. Then, the solution was cooled to room temperature and concentrated. The crude material was directly used in the next step without any further purification. To a stirred solution of this crude material (220 mg) in methanol (1 mL) was added HCl in methanol (1 mL) dropwise at 0° C. The reaction mixture was stirred for 2 h at room temperature then concentrated in vacuo. The residue was purified by PREP-HPLC to afford 110 as a dark yellow solid, % Yield: 19.5 mg; Mass (m/z): 611.4 (M+H)$^+$; TLC Rf: Methanol:DCM (10:90)=0.1; $^1$H NMR (400 MHz, DMSO-d6): δ 8.98 (s, 1H), 8.30 (d, J=4.8 Hz, 1H), 7.99 (d, J=6.4 Hz, 1H), 7.82-7.79 (m, 1H), 7.67-7.55 (m, 3H), 7.42-7.39 (m, 1H), 7.31-7.15 (m, 3H), 6.84 (d, J=7.5 Hz, 1H), 4.94 (s, 1H), 4.82 (s, 1H), 3.11-3.07 (m, 2H), 2.86-2.44 (m, 2H), 1.97-1.78 (m, 2H).

(S)-2-chloro-N-(5-((5-(2-((5,5-difluoropiperidin-3-yl) amino) pyrimidin-4-yl) thiazol-4-yl) oxy) naphthalen-1-yl) benzene sulfonamide (111): A mixture of 106 (75 mg, 0.13 mmol), 108 (92 mg, 0.39 mmol) and TEA (1 mL) in DMSO (2 mL) was degassed and backfilled with nitrogen. The reaction mixture was heated to 180° C. under microwave conditions for 4 h. The solution was cooled to room temperature, diluted with ethyl acetate, washed with water and brine, dried over Na$_2$SO$_4$ and concentrated. The crude material was directly used in the next step without any further purification. To a stirred solution of this material (120 mg) in methanol (1 mL) was added HCl in methanol (1 mL) dropwise at 0° C. The mixture was stirred for 2 h at room temperature, concentrated in vacuo and purified by PREP HPLC to afford 111 as a white solid. % of Yield: 7.5 mg; Mass (m/z): 629.2 (M+H)+; TLC Rf: Methanol:DCM (10:90)=0.1; 1H NMR (400 MHz, DMSO-d6): δ 8.98 (s, 1H), 8.31 (d, J=5.2 Hz, 1H), 8.06 (s, 1H), 7.87 (d, J=7.6 Hz, 1H), 7.82-7.79 (m, 1H), 7.66-7.60 (m, 3H), 7.43 (s, 2H), 7.26-7.21 (m, 2H), 7.09 (s, 1H), 4.03 (m, 2H), 3.02 (m, 3H), 2.0 (m, 2H).

N-(5-((5-(2-((1,4-oxazepan-6-yl) amino) pyrimidin-4-yl) thiazol-4-yl) oxy) naphthalen-1-yl)-2-chlorobenzenesulfonamide (112): A mixture of 106 (75 mg, 0.13 mmol), 109 (85 mg, 0.39 mmol) and TEA (1 mL) in 1,4-dioxane (2 mL) was degassed and backfilled with nitrogen. The reaction was heated to 100° C. for 72 h. Then the solution was cooled to room temperature, concentrated and the crude material was directly used in the next step without any further purification. To a stirred solution of this material (180 mg) in methanol (1 mL) was added HCl in methanol (1 mL) dropwise at 0° C. The reaction mixture was stirred for 2 h at room temperature, concentrated in vacuo and purified by PREP HPLC to afford 112 as a dark yellow solid. % of Yield: 19.7 mg; Mass (m/z): 609.4 (M+H); TLC Rf: Methanol: DCM (10:90)=0.1; $^1$H NMR (400 MHz, DMSO-d6): δ 8.97 (s, 1H), 8.30 (d, J=4.8 Hz, 1H), 7.91 (d, J=8 Hz, 1H), 7.82-7.79 (m, 1H), 7.67-7.55 (m, 3H), 7.42-7.39 (m, 1H), 7.31-7.15 (m, 3H), 6.84 (d, J=7.5 Hz, 1H), 4.2 (brs, 1H, NH), 3.87 (m, 2H), 3.67 (m, 2H), 3.3-2.98 (m, 5H).

IRE1α kinase IC$_{50}$, IRE1α RNase IC$_{50}$, and IRE1β kinase IC$_{50}$ activities for compounds described herein are provided in Table 1.

TABLE 1

| Compound | IRE1α kinase IC$_{50}$ | IRE1α RNase IC$_{50}$ | IRE1β kinase IC$_{50}$ |
|---|---|---|---|
|  | 98 nM | 117 nM (HF) | 120 nM |

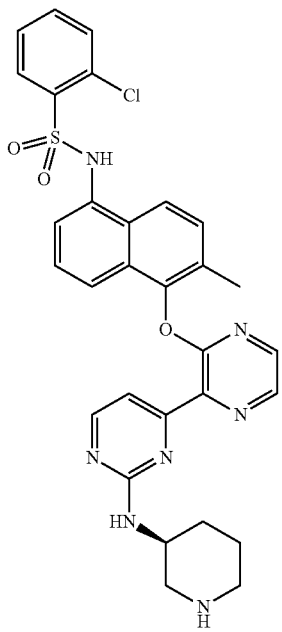 [SMILES: Cc1ccc2c(NS(=O)(=O)c3ccccc3Cl)cccc2c1Oc1nccnc1-c1ccnc(N[C@H]2CCCNC2)n1]

compound 96

TABLE 1-continued
| Compound | IRE1α kinase IC$_{50}$ | IRE1α RNase IC$_{50}$ | IRE1β kinase IC$_{50}$ |
|---|---|---|---|
| 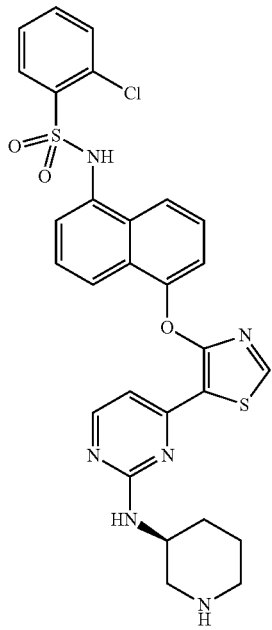 [SMILES: O=S(=O)(Nc1cccc2c(Oc3ncsc3-c3ccnc(N[C@H]4CCCNC4)n3)cccc12)c1ccccc1Cl] compound 47 | 10 nM | 8.3 nM (HF) | 181 nM |
| 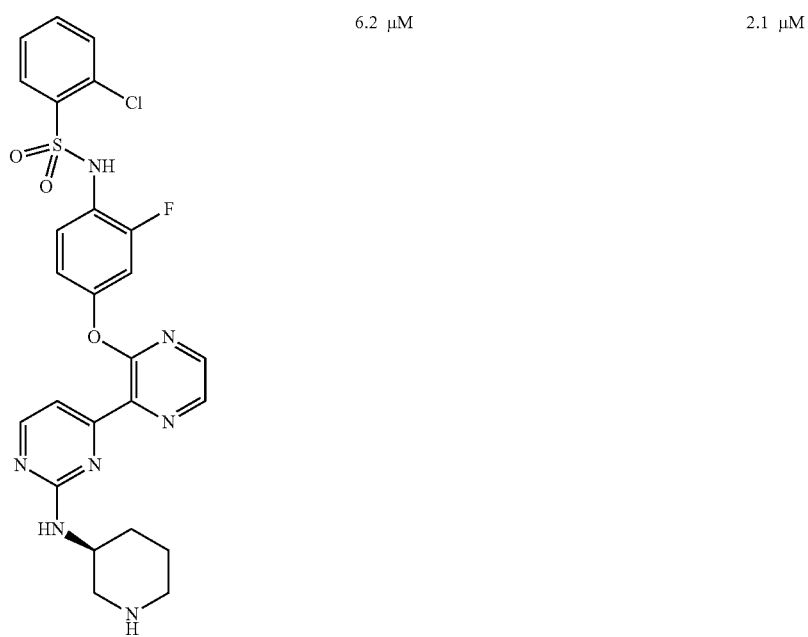 compound 77 | 6.2 μM | | 2.1 μM |

TABLE 1-continued
| Compound | IRE1α kinase IC$_{50}$ | IRE1α RNase IC$_{50}$ | IRE1β kinase IC$_{50}$ |
|---|---|---|---|
| 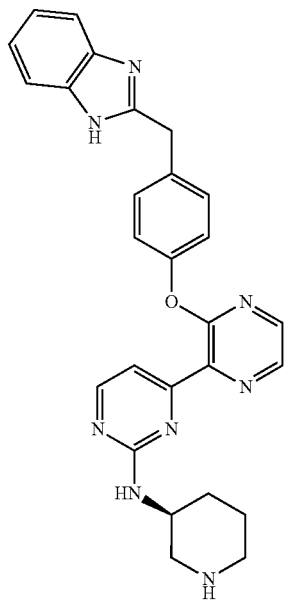 [SMILES: c1ccc2[nH]c(Cc3ccc(Oc4nccnc4-c4ccnc(N[C@H]5CCCNC5)n4)cc3)nc2c1] compound 88 | 7.3 μM | | >10 μM |
| 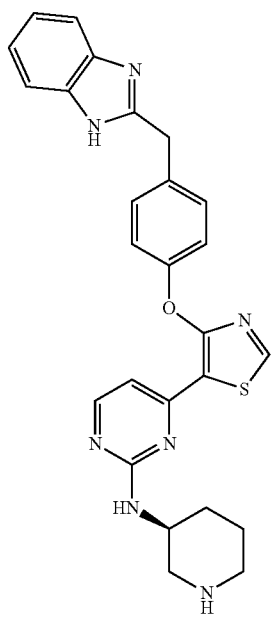 [SMILES: c1ccc2[nH]c(Cc3ccc(Oc4ncsc4-c4ccnc(N[C@H]5CCCNC5)n4)cc3)nc2c1] compound 30 | 439 nM | 118 nM | 8.4 μM |

TABLE 1-continued
| Compound | IRE1α kinase IC$_{50}$ | IRE1α RNase IC$_{50}$ | IRE1β kinase IC$_{50}$ |
|---|---|---|---|
| 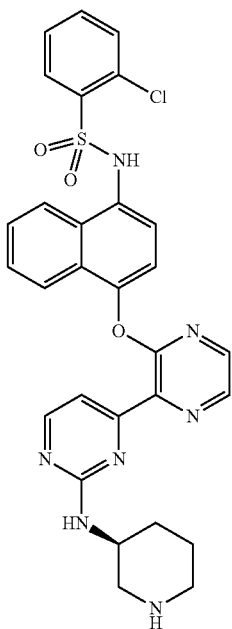 [SMILES: O=S(=O)(Nc1ccc(Oc2nccnc2-c2ccnc(N[C@H]3CCCNC3)n2)c2ccccc12)c1ccccc1Cl]\ncompound 84 | 296 nM | | 1.98 μM |
| 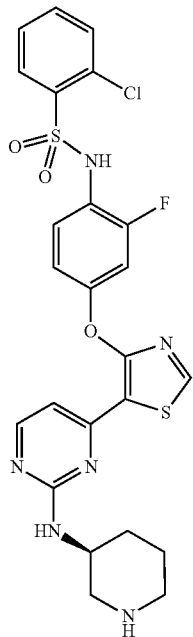 [SMILES: O=S(=O)(Nc1ccc(Oc2ncsc2-c2ccnc(N[C@H]3CCCNC3)n2)cc1F)c1ccccc1Cl]\ncompound 25 | 117 nM | 46 nM (HF) | 32 nM |

TABLE 1-continued
| Compound | IRE1α kinase IC$_{50}$ | IRE1α RNase IC$_{50}$ | IRE1β kinase IC$_{50}$ |
|---|---|---|---|
| 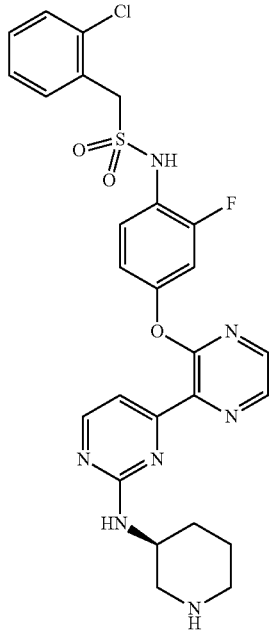 [SMILES: O=S(=O)(Cc1ccccc1Cl)Nc1ccc(Oc2nccnc2-c2ccnc(N[C@H]3CCCNC3)n2)cc1F] compound 73 | 961 nM | | 1.57 μM |
| 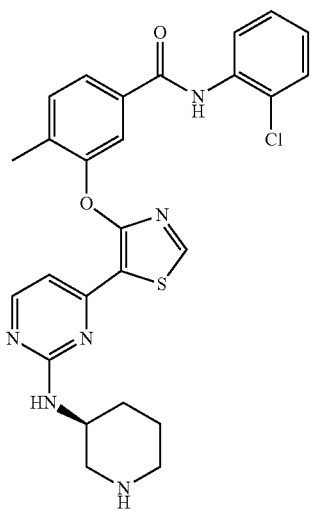 [SMILES: Cc1ccc(C(=O)Nc2ccccc2Cl)cc1Oc1ncsc1-c1ccnc(N[C@H]2CCCNC2)n1] compound 16 | 228 nM (RB) 307 nM (HF) | | >10 μM |

TABLE 1-continued
| Compound | IRE1α kinase IC$_{50}$ | IRE1α RNase IC$_{50}$ | IRE1β kinase IC$_{50}$ |
|---|---|---|---|
| 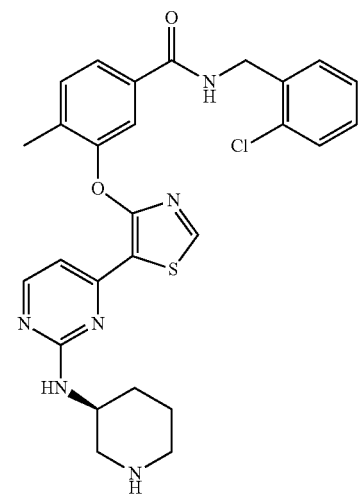 [SMILES: Cc1ccc(C(=O)NCc2ccccc2Cl)cc1Oc1ncsc1-c1ccnc(N[C@H]2CCCNC2)n1]<br>compound 20 | 52 nM (RB)<br>55 nM (HF) | No inhibition of pIRE1α | >10 μM |
| 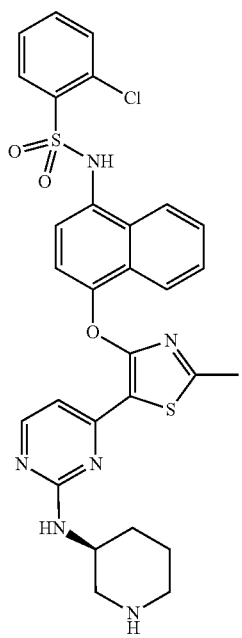 [SMILES: Cc1nc(Oc2ccc(NS(=O)(=O)c3ccccc3Cl)c3ccccc23)c(-c2ccnc(N[C@H]3CCCNC3)n2)s1]<br>compound 67 | 63 nM (HF) | 19 nM (HF) | |

TABLE 1-continued
| Compound | IRE1α kinase IC$_{50}$ | IRE1α RNase IC$_{50}$ | IRE1β kinase IC$_{50}$ |
|---|---|---|---|
| 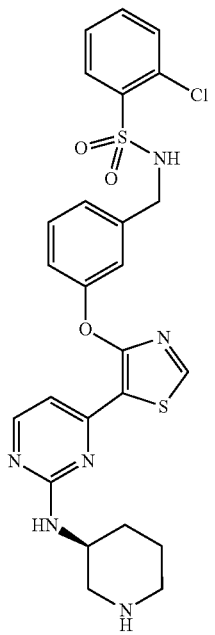 [SMILES: O=S(=O)(NCc1cccc(Oc2ncsc2-c2ccnc(N[C@H]3CCCNC3)n2)c1)c1ccccc1Cl] compound 43 | 1595 nM (HF) | | |
| 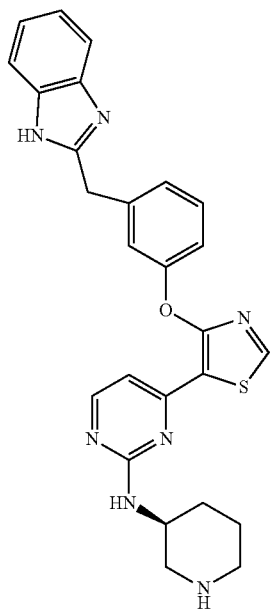 [SMILES: c1cc(Cc2nc3ccccc3[nH]2)cc(Oc2ncsc2-c2ccnc(N[C@H]3CCCNC3)n2)c1] compound 35 | 443 n (HF) | 153 nM (HF) | |

TABLE 1-continued
| Compound | IRE1α kinase IC$_{50}$ | IRE1α RNase IC$_{50}$ | IRE1β kinase IC$_{50}$ |
|---|---|---|---|
| 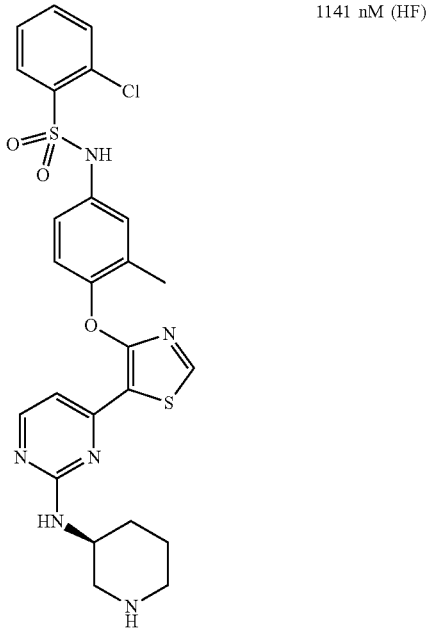<br>compound 39 | | 1141 nM (HF) | |
| 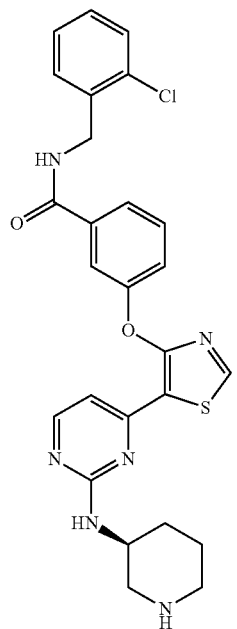 [SMILES: O=C(NCc1ccccc1Cl)c1cccc(Oc2ncsc2-c2ccnc(N[C@H]3CCCNC3)n2)c1]<br>compound 51 | | 524 nM (HF) | |

TABLE 1-continued
| Compound | IRE1α kinase IC$_{50}$ | IRE1α RNase IC$_{50}$ | IRE1β kinase IC$_{50}$ |
|---|---|---|---|
| 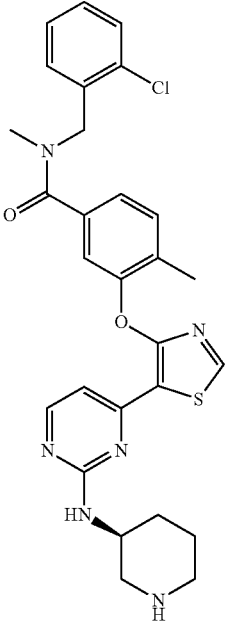 [SMILES: Cc1ccc(C(=O)N(C)Cc2ccccc2Cl)cc1Oc1ncsc1-c1ccnc(N[C@H]2CCCNC2)n1] compound 55 | 3185 nM (HF) | | |
| 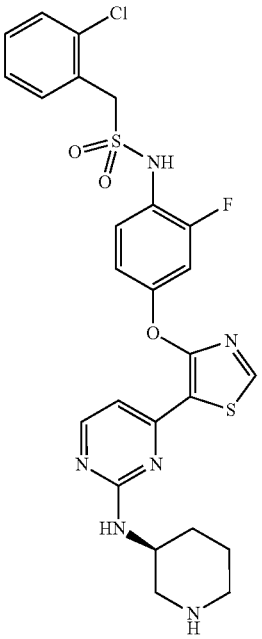 [SMILES: O=S(=O)(Cc1ccccc1Cl)Nc1ccc(Oc2ncsc2-c2ccnc(N[C@H]3CCCNC3)n2)cc1F] compound 11 | 119 nM (HF) | 24 nM (HF) | |

It is understood that the examples described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of formula (Ia) or formula (Ib):

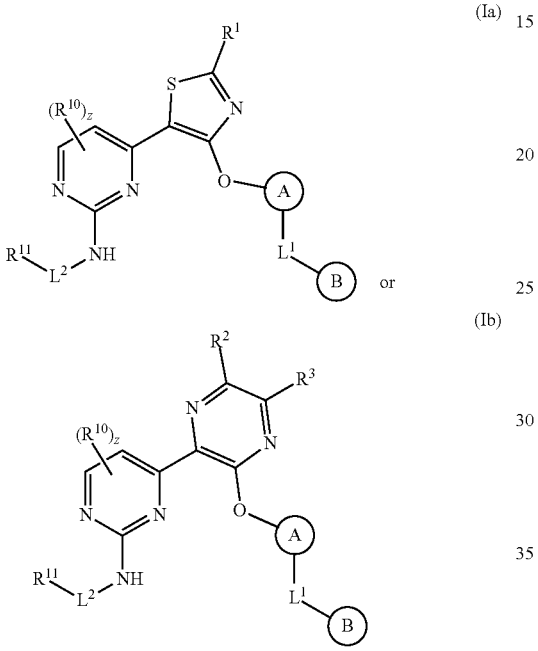

or a pharmaceutically acceptable salt, stereoisomer, or tautomer thereof,
wherein:
  $R^{11}$ is $NR^{14}R^{14}$ or a nitrogen-containing heterocycloalkyl, wherein the nitrogen-containing heterocycloalkyl is substituted with n independently selected $R^5$ substituents;
  each $R^{14}$ is independently hydrogen, alkyl, heteroalkyl, $CH_2X^{14}$, $CH(X^{14})_2$, $C(X^{14})_3$, $C(O)R^{14A}$, $C(O)NR^{14A}R^{14B}$, $C(O)NHNR^{14A}R^{14B}$, $C(O)OR^{14A}$, $NR^{14A}R^{14B}$, $NR^{14A}C(O)R^{14B}$, $NHC(O)NR^{14A}R^{14B}$, $NR^{14A}C(O)OR^{14B}$, $NHNR^{14A}R^{14B}$, $NR^{14A}OR^{14B}$, $NR^{14A}S(O)_2R^{14B}$, $OR^{14A}$, $OCH_2X^{14}$, $OCH(X^{14})_2$, $OC(X^{14})_3$, $SR^{14A}$, $S(O)R^{14A}$, $S(O)_2R^{14A}$, $S(O)_2NR^{14A}R^{14B}$, cycloalkyl, heterocycloalkyl, aryl, or heteroaryl;
  each $R^{14A}$ is independently hydrogen, alkyl, heteroalkyl, $CH_2X$, $CH(X)_2$, $C(X)_3$, $C(O)NH_2$, $C(O)OH$, $NH_2$, $NHC(O)H$, $NHC(O)NH_2$, $NHC(O)NHNH_2$, $NHC(O)OH$, $NHNH_2$, $NHOH$, $NHS(O)_2H$, $OH$, $OS(O)_2OH$, $OCH_2X$, $OCH(X)_2$, $OC(X)_3$, $ONH_2$, $SH$, $S(O)_2NH_2$, $S(O)_2OH$, cycloalkyl, heterocycloalkyl, aryl, or heteroaryl;
  each $R^{14B}$ is independently hydrogen, alkyl, heteroalkyl, $CH_2X$, $CH(X)_2$, $C(X)_3$, $C(O)NH_2$, $C(O)OH$, $NH_2$, $NHC(O)H$, $NHC(O)NH_2$, $NHC(O)NHNH_2$, $NHC(O)OH$, $NHNH_2$, $NHOH$, $NHS(O)_2H$, $OH$, $OS(O)_2OH$, $OCH_2X$, $OCH(X)_2$, $OC(X)_3$, $ONH_2$, $SH$, $S(O)_2NH_2$, $S(O)_2OH$, cycloalkyl, heterocycloalkyl, aryl, or heteroaryl; or
  any $R^{14A}$ and $R^{14B}$, together with the nitrogen atom to which they are bonded, independently forms a heterocycloalkyl or heteroaryl;
  each $X^{14}$ is independently halogen;
  each $R^5$ is independently halogen, CN, $NO_2$, alkyl, heteroalkyl, $CH_2X^5$, $CH(X^5)_2$, $C(X^5)_3$, $C(O)R^{5A}$, $C(O)NR^{5A}R^{5B}$, $C(O)NHNR^{5A}R^{5B}$, $C(O)OR^{5A}$, $NR^{5A}R^{5B}$, $NR^{5A}C(O)R^{5B}$, $NHC(O)NR^{5A}R^{5B}$, $NR^{5A}C(O)OR^{5B}$, $NHNR^{5A}R^{5B}$, $N_3$, $NR^{5A}OR^{5B}$, $NR^{5A}S(O)_2R^{5B}$, $OR^{5A}$, $OCH_2X^5$, $OCH(X^5)_2$, $OC(X^5)_3$, $SR^{5A}$, $S(O)R^{5A}$, $S(O)_2R^{5A}$, $S(O)_2NR^{5A}R^{5B}$, cycloalkyl, heterocycloalkyl, aryl, or heteroaryl;
  each $R^{5A}$ is independently hydrogen, alkyl, heteroalkyl, $CH_2X^5$, $CH(X^5)_2$, $C(X^5)_3$, $C(O)NH_2$, $C(O)OH$, $NH_2$, $NHC(O)H$, $NHC(O)NH_2$, $NHC(O)NHNH_2$, $NHC(O)OH$, $NHNH_2$, $NHOH$, $NHS(O)_2H$, $OH$, $OS(O)_2OH$, $OCH_2X^5$, $OCH(X^5)_2$, $OC(X^5)_3$, $ONH_2$, $SH$, $S(O)_2NH_2$, $S(O)_2OH$, cycloalkyl, heterocycloalkyl, aryl, or heteroaryl;
  each $R^{5B}$ is independently hydrogen, alkyl, heteroalkyl, $CH_2X^5$, $CH(X^5)_2$, $C(X^5)_3$, $C(O)NH_2$, $C(O)OH$, $NH_2$, $NHC(O)H$, $NHC(O)NH_2$, $NHC(O)NHNH_2$, $NHC(O)OH$, $NHNH_2$, $NHOH$, $NHS(O)_2H$, $OH$, $OS(O)_2OH$, $OCH_2X^5$, $OCH(X^5)_2$, $OC(X^5)_3$, $ONH_2$, $SH$, $S(O)_2NH_2$, $S(O)_2OH$, cycloalkyl, heterocycloalkyl, aryl, or heteroaryl; or
  any $R^{5A}$ and $R^{5B}$, together with the nitrogen atom to which they are bonded, independently forms a heterocycloalkyl or heteroaryl;
  each $X^5$ is independently halogen;
  $L^2$ is a bond;
  $R^{10}$ is alkyl, heteroalkyl, $CH_2X^{10}$, $CH(X^{10})_2$, $C(X^{10})_3$, $C(O)R^{10A}$, $C(O)NR^{10A}R^{10B}$, $C(O)NHNR^{10A}R^{10B}$ $C(O)OR^{10A}$, $NR^{10A}R^{10B}$, $NR^{10A}C(O)R^{10B}$, $NHC(O)NR^{10A}R^{10B}$, $NR^{10A}C(O)OR^{10B}$, $NHNR^{10A}R^{10B}$, $NR^{10A}OR^{10B}$, $NR^{10A}S(O)_2R^{10B}$, $OR^{10A}$, $OCH_2X^{10}$, $OCH(X^{10})_2$, $OC(X^{10})_3$, $SR^{10A}$, $S(O)R^{10A}$, $S(O)_2R^{10A}$, $S(O)_2NR^{10A}R^{10B}$, cycloalkyl, heterocycloalkyl, aryl, or heteroaryl;
  $R^{10A}$ is hydrogen, alkyl, heteroalkyl, $CH_2X$, $CH(X)_2$, $C(X)_3$, $C(O)NH_2$, $C(O)OH$, $NH_2$, $NHC(O)H$, $NHC(O)NH_2$, $NHC(O)NHNH_2$, $NHC(O)OH$, $NHNH_2$, $NHOH$, $NHS(O)_2H$, $OH$, $OS(O)_2OH$, $OCH_2X$, $OCH(X)_2$, $OC(X)_3$, $ONH_2$, $SH$, $S(O)_2NH_2$, $S(O)_2OH$, cycloalkyl, heterocycloalkyl, aryl, or heteroaryl;
  $R^{10B}$ is hydrogen, alkyl, heteroalkyl, $CH_2X$, $CH(X)_2$, $C(X)_3$, $C(O)NH_2$, $C(O)OH$, $NH_2$, $NHC(O)H$, $NHC(O)NH_2$, $NHC(O)NHNH_2$, $NHC(O)OH$, $NHNH_2$, $NHOH$, $NHS(O)_2H$, $OH$, $OS(O)_2OH$, $OCH_2X$, $OCH(X)_2$, $OC(X)_3$, $ONH_2$, $SH$, $S(O)_2NH_2$, $S(O)_2OH$, cycloalkyl, heterocycloalkyl, aryl, or heteroaryl; or
  $R^{10A}$ and $R^{10B}$, together with the nitrogen atom to which they are bonded, form a heterocycloalkyl or heteroaryl;
  each $X^{10}$ is independently halogen;
  $R^1$ is hydrogen, halogen, CN, $NO_2$, alkyl, heteroalkyl, $CH_2X^1$, $CH(X^1)_2$, $C(X^1)_3$, $C(O)R^{1A}$, $C(O)NR^{1A}R^{1B}$, $C(O)NHNR^{1A}R^{1B}C(O)OR^{1A}$, $NR^{1A}R^{1B}$, $NR^{1A}C(O)R^{1B}$, $NHC(O)NR^{1A}R^{1B}$, $NR^{1A}C(O)OR^{1B}$, $NHNR^{1A}R^{1B}$, $N_3$, $NR^{1A}OR^{1B}$, $NR^{1A}S(O)_2R^{1B}$, $OR^{1A}$, $OCH_2X^1$, $OCH(X^1)_2$, $OC(X^1)_3$, $SR^{1A}$, $S(O)R^{1A}$, $S(O)_2R^{1A}$, $S(O)_2NR^{1A}R^{1B}$, cycloalkyl, heterocycloalkyl, aryl, or heteroaryl;
  $R^{1A}$ is hydrogen, alkyl, heteroalkyl, $CH_2X$, $CH(X)_2$, $C(X)_3$, $C(O)NH_2$, $C(O)OH$, $NH_2$, $NHC(O)H$, $NHC(O)$

167

NH$_2$, NHC(O)NHNH$_2$, NHC(O)OH, NHNH$_2$, NHOH, NHS(O)$_2$H, OH, OS(O)$_2$OH, OCH$_2$X, OCH(X)$_2$, OC(X)$_3$, ONH$_2$, SH, S(O)$_2$NH$_2$, S(O)$_2$OH, cycloalkyl, heterocycloalkyl, aryl, or heteroaryl;

R$^{1B}$ is hydrogen, alkyl, heteroalkyl, CH$_2$X, CH(X)$_2$, C(X)$_3$, C(O)NH$_2$, C(O)OH, NH$_2$, NHC(O)H, NHC(O)NH$_2$, NHC(O)NHNH$_2$, NHC(O)OH, NHNH$_2$, NHOH, NHS(O)$_2$H, OH, OS(O)$_2$OH, OCH$_2$X, OCH(X)$_2$, OC(X)$_3$, ONH$_2$, SH, S(O)$_2$NH$_2$, S(O)$_2$OH, cycloalkyl, heterocycloalkyl, aryl, or heteroaryl; or R$^{1A}$ and R$^{1B}$, together with the nitrogen atom to which they are bonded, form a heterocycloalkyl or heteroaryl;

each X$^1$ is independently halogen;

R$^2$ is hydrogen, halogen, CN, NO$_2$, alkyl, heteroalkyl, CH$_2$X$^2$, CH(X$^2$)$_2$, C(X$^2$)$_3$, C(O)R$^{2A}$, C(O)NR$^{2A}$R$^{2B}$, C(O)NHNR$^{2A}$R$^{2B}$, C(O)OR$^{2A}$, NR$^{2A}$R$^{2B}$, NR$^{2A}$C(O)R$^{2B}$, NHC(O)NR$^{2A}$R$^{2B}$, NR$^{2A}$C(O)OR$^{2B}$, NHNR$^{2A}$R$^{2B}$, N$_3$, NR$^{2A}$OR$^{2B}$, NR$^{2A}$S(O)$_2$R$^{2B}$, OR$^{2A}$, OCH$_2$X$^2$, OCH(X$^2$)$_2$, OC(X$^2$)$_3$, SR$^{2A}$, S(O)R$^{2A}$, S(O)$_2$R$^{2A}$, S(O)$_2$NR$^{2A}$R$^{2B}$, cycloalkyl, heterocycloalkyl, aryl, or heteroaryl;

R$^{2A}$ is hydrogen, alkyl, heteroalkyl, CH$_2$X, CH(X)$_2$, C(X)$_3$, C(O)NH$_2$, C(O)OH, NH$_2$, NHC(O)H, NHC(O)NH$_2$, NHC(O)NHNH$_2$, NHC(O)OH, NHNH$_2$, NHOH, NHS(O)$_2$H, OH, OS(O)$_2$OH, OCH$_2$X, OCH(X)$_2$, OC(X)$_3$, ONH$_2$, SH, S(O)$_2$NH$_2$, S(O)$_2$OH, cycloalkyl, heterocycloalkyl, aryl, or heteroaryl;

R$^{2B}$ is hydrogen, alkyl, heteroalkyl, CH$_2$X, CH(X)$_2$, C(X)$_3$, C(O)NH$_2$, C(O)OH, NH$_2$, NHC(O)H, NHC(O)NH$_2$, NHC(O)NHNH$_2$, NHC(O)OH, NHNH$_2$, NHOH, NHS(O)$_2$H, OH, OS(O)$_2$OH, OCH$_2$X, OCH(X)$_2$, OC(X)$_3$, ONH$_2$, SH, S(O)$_2$NH$_2$, S(O)$_2$OH, cycloalkyl, heterocycloalkyl, aryl, or heteroaryl; or R$^{2A}$ and R$^{2B}$, together with the nitrogen atom to which they are bonded, form a heterocycloalkyl or heteroaryl;

each X$^2$ is independently halogen;

R$^3$ is hydrogen, halogen, CN, NO$_2$, alkyl, heteroalkyl, CH$_2$X$^3$, CH(X$^3$)$_2$, C(X$^3$)$_3$, C(O)R$^{3A}$, C(O)NR$^{3A}$R$^{3B}$C(O)NHNR$^{3A}$R$^{3B}$, C(O)OR$^{3A}$, NR$^{3A}$R$^{3B}$, NR$^{3A}$C(O)R$^{3B}$, NHC(O)NR$^{3A}$R$^{3B}$, NR$^{3A}$C(O)OR$^{3B}$, NHNR$^{3A}$R$^{3B}$N$_3$, NR$^{3A}$OR$^{3B}$, NR$^{3A}$S(O)$_2$R$^{3B}$, OR$^{3A}$, OCH$_2$X$^3$, OCH(X$^3$)$_2$, OC(X$^3$)$_3$, SR$^{3A}$, S(O)R$^{3A}$, S(O)$_2$R$^{3A}$, S(O)$_2$NR$^{3A}$R$^{3B}$, cycloalkyl, heterocycloalkyl, aryl, or heteroaryl;

R$^{3A}$ is hydrogen, alkyl, heteroalkyl, CH$_2$X, CH(X)$_2$, C(X)$_3$, C(O)NH$_2$, C(O)OH, NH$_2$, NHC(O)H, NHC(O)NH$_2$, NHC(O)NHNH$_2$, NHC(O)OH, NHNH$_2$, NHOH, NHS(O)$_2$H, OH, OS(O)$_2$OH, OCH$_2$X, OCH(X)$_2$, OC(X)$_3$, ONH$_2$, SH, S(O)$_2$NH$_2$, S(O)$_2$OH, cycloalkyl, heterocycloalkyl, aryl, or heteroaryl;

R$^{3B}$ is hydrogen, alkyl, heteroalkyl, CH$_2$X, CH(X)$_2$, C(X)$_3$, C(O)NH$_2$, C(O)OH, NH$_2$, NHC(O)H, NHC(O)NH$_2$, NHC(O)NHNH$_2$, NHC(O)OH, NHNH$_2$, NHOH, NHS(O)$_2$H, OH, OS(O)$_2$OH, OCH$_2$X, OCH(X)$_2$, OC(X)$_3$, ONH$_2$, SH, S(O)$_2$NH$_2$, S(O)$_2$OH, cycloalkyl, heterocycloalkyl, aryl, or heteroaryl; or R$^{3A}$ and R$^{3B}$, together with the nitrogen atom to which they are bonded, form a heterocycloalkyl or heteroaryl;

each X$^3$ is independently halogen;

ring A is aryl or heteroaryl, wherein the aryl or heteroaryl is substituted with n independently selected R$^8$ substituents;

each R$^8$ is independently halogen, CN, NO$_2$, alkyl, heteroalkyl, CH$_2$X$^8$, CH(X$^8$)$_2$, C(X$^8$)$_3$, C(O)R$^{8A}$, C(O)NR$^{8A}$R$^{8B}$, C(O)NHNR$^{8A}$R$^{8B}$, C(O)OR$^{8A}$, NR$^{8A}$R$^{8B}$, NR$^{8A}$C(O)R$^{8B}$, NHC(O)NR$^{8A}$R$^{8B}$, NR$^{8A}$C(O)OR$^{8B}$, NHNR$^{8A}$R$^{8B}$, N$_3$, NR$^{8A}$OR$^{8B}$, NR$^{8A}$S(O)$_2$R$^{8B}$, OR$^{8A}$,

168

OCH$_2$X$^8$, OCH(X$^8$)$_2$, OC(X$^8$)$_3$, SR$^{8A}$, S(O)R$^{8A}$, S(O)$_2$R$^{8A}$, S(O)$_2$NR$^{8A}$R$^{8B}$, cycloalkyl, heterocycloalkyl, aryl, or heteroaryl, wherein each cycloalkyl, heterocycloalkyl, aryl, and heteroaryl is optionally and independently substituted with 1, 2, 3, 4, 5, 6, 7, 8, or 9 substituents independently selected from the group consisting of halogen, NO$_2$, alkyl, heteroalkyl, CF$_3$, CCl$_3$, CBr$_3$, CI$_3$, C(O)NH$_2$, C(O)OH, NH$_2$, NHC(O)H, NHC(O)NHNH$_2$, NHC(O)OH, NHNH$_2$, N$_3$, NHOH, NHS(O)$_2$H, OH, OCH$_2$F, OCH$_2$Cl, OCH$_2$Br, OCH$_2$I, OCHF$_2$, OCHCl$_2$, OCHBr$_2$, OCHI$_2$, OCF$_3$, OCCl$_3$, OCBr$_3$, OCI$_3$, ONH$_2$, OS(O)$_2$OH, SH, S(O)$_2$NH$_2$, S(O)$_2$OH, cycloalkyl, heterocycloalkyl, aryl, and heteroaryl;

each R$^{8A}$ is independently hydrogen, alkyl, heteroalkyl, CH$_2$X$^8$, CH(X$^8$)$_2$, C(X$^8$)$_3$, C(O)NH$_2$, C(O)OH, NH$_2$, NHC(O)H, NHC(O)NH$_2$, NHC(O)NHNH$_2$, NHC(O)OH, NHNH$_2$, NHOH, NHS(O)$_2$H, OH, OS(O)$_2$OH, OCH$_2$X$^8$, OCH(X$^8$)$_2$, OC(X$^8$)$_3$, ONH$_2$, SH, S(O)$_2$NH$_2$, S(O)$_2$OH, cycloalkyl, heterocycloalkyl, aryl, or heteroaryl;

each R$^{8B}$ is independently hydrogen, alkyl, heteroalkyl, CH$_2$X$^8$, CH(X$^8$)$_2$, C(X$^8$)$_3$, C(O)NH$_2$, C(O)OH, NH$_2$, NHC(O)H, NHC(O)NH$_2$, NHC(O)NHNH$_2$, NHC(O)OH, NHNH$_2$, NHOH, NHS(O)$_2$H, OH, OS(O)$_2$OH, OCH$_2$X$^8$, OCH(X$^8$)$_2$, OC(X$^8$)$_3$, ONH$_2$, SH, S(O)$_2$NH$_2$, S(O)$_2$OH, cycloalkyl, heterocycloalkyl, aryl, or heteroaryl; or any R$^{8A}$ and R$^{8B}$, together with the nitrogen atom to which they are bonded, independently forms a heterocycloalkyl or heteroaryl;

each X$^8$ is independently halogen;

L$^1$ is alkylene, —CH$_2$NR$^{12}$S(O)$_2$—, —CH$_2$S(O)$_2$NR$^{12}$—, —C(O)—, —C(O)NR$^{12}$—, —C(O)NR$^{12}$CH$_2$—, —C(O)O—, —NR$^{12}$—, —NR$^{12}$C(O)—, —NR$^{12}$C(O)O—, —NR$^{12}$S(O)$_2$—, —NR$^{12}$S(O)$_2$CH$_2$—, —O—, —OC(O)—, —OC(O)NR$^{12}$—, —S—, —S(O)—, —S(O)$_2$—, —S(O)$_2$NR$^{12}$—, or —S(O)$_2$NR$^{12}$CH$_2$—;

R$^{12}$ is hydrogen, alkyl, heteroalkyl, CH$_2$X$^{12}$, CH(X$^1$$_2$)$_2$, C(X$^1$$_2$)$_3$, C(O)R$^{12A}$, C(O)NR$^{12A}$R$^{12B}$C(O)NHNR$^{12A}$R$^{12B}$, C(O)OR$^{12A}$, NR$^{12A}$R$^{12B}$, NR$^{12A}$C(O)R$^{12B}$, NHC(O)NR$^{12A}$R$^{12B}$, NR$^{12A}$C(O)OR$^{12B}$, NHNR$^{12A}$R$^{12B}$, NR$^{12A}$OR$^{12B}$, NR$^{12A}$S(O)$_2$R$^{12B}$, OR$^{12A}$, OCH$_2$X$^{12}$, OCH(X$^{12}$)$_2$, OC(X$^{12}$)$_3$, SR$^{12A}$, S(O)R$^{12A}$ S(O)$_2$R$^{12A}$, S(O)$_2$NR$^{12A}$R$^{12B}$, cycloalkyl, heterocycloalkyl, aryl, or heteroaryl;

R$^{12A}$ is hydrogen, alkyl, heteroalkyl, CH$_2$X, CH(X)$_2$, C(X)$_3$, C(O)NH$_2$, C(O)OH, NH$_2$, NHC(O)H, NHC(O)NH$_2$, NHC(O)NHNH$_2$, NHC(O)OH, NHNH$_2$, NHOH, NHS(O)$_2$H, OH, OS(O)$_2$OH, OCH$_2$X, OCH(X)$_2$, OC(X)$_3$, ONH$_2$, SH, S(O)$_2$NH$_2$, S(O)$_2$OH, cycloalkyl, heterocycloalkyl, aryl, or heteroaryl;

R$^{12B}$ is hydrogen, alkyl, heteroalkyl, CH$_2$X, CH(X)$_2$, C(X)$_3$, C(O)NH$_2$, C(O)OH, NH$_2$, NHC(O)H, NHC(O)NH$_2$, NHC(O)NHNH$_2$, NHC(O)OH, NHNH$_2$, NHOH, NHS(O)$_2$H, OH, OS(O)$_2$OH, OCH$_2$X, OCH(X)$_2$, OC(X)$_3$, ONH$_2$, SH, S(O)$_2$NH$_2$, S(O)$_2$OH, cycloalkyl, heterocycloalkyl, aryl, or heteroaryl; or R$^{12A}$ and R$^{12B}$, together with the nitrogen atom to which they are bonded, form a heterocycloalkyl or heteroaryl;

each $X^{12}$ is independently halogen;

each X is independently halogen;

ring B is cycloalkyl, heterocycloalkyl, aryl, or heteroaryl, wherein the cycloalkyl, heterocycloalkyl, aryl, or heteroaryl is substituted with n independently selected $R^6$ substituents;

each $R^6$ is independently halogen, CN, $NO_2$, alkyl, heteroalkyl, $CH_2X^6$, $CH(X^6)_2$, $C(X^6)_3$, $C(O)R^{6A}$, $C(O)NR^{6A}R^{6B}$, $C(O)NHNR^{6A}R^{6B}$, $C(O)OR^{6A}$, $NR^{6A}R^{6B}$, $NR^{6A}C(O)R^{6B}$, $NHC(O)NR^{6A}R^{6B}$, $NR^{6A}C(O)OR^{6B}$, $NHNR^{6A}R^{6B}$, $N_3$, $NR^{6A}OR^{6B}$, $NR^{6A}S(O)_2R^{6B}$, $OR^{6A}$, $OCH_2X^6$, $OCH(X^6)_2$, $OC(X^6)_3$, $SR^{6A}$, $S(O)R^{6A}$, $S(O)_2R^{6A}$, $S(O)_2NR^{6A}R^{6B}$, cycloalkyl, heterocycloalkyl, aryl, or heteroaryl, wherein each cycloalkyl, heterocycloalkyl, aryl, and heteroaryl is optionally and independently substituted with 1, 2, 3, 4, 5, 6, 7, 8, or 9 substituents independently selected from the group consisting of halogen, $NO_2$, alkyl, heteroalkyl, $CF_3$, $CCl_3$, $CBr_3$, $CI_3$, $C(O)NH_2$, $C(O)OH$, $NH_2$, $NHC(O)H$, $NHC(O)NHNH_2$, $NHC(O)OH$, $NHNH_2$, $N_3$, $NHOH$, $NHS(O)_2H$, $OH$, $OCH_2F$, $OCH_2Cl$, $OCH_2Br$, $OCH_2I$, $OCHF_2$, $OCHCl_2$, $OCHBr_2$, $OCHI_2$, $OCF_3$, $OCCl_3$, $OCBr_3$, $OCI_3$, $ONH_2$, $OS(O)_2OH$, $SH$, $S(O)_2NH_2$, $S(O)_2OH$, cycloalkyl, heterocycloalkyl, aryl, and heteroaryl;

each $R^{6A}$ is independently hydrogen, alkyl, heteroalkyl, $CH_2X^6$, $CH(X^6)_2$, $C(X^6)_3$, $C(O)NH_2$, $C(O)OH$, $NH_2$, $NHC(O)H$, $NHC(O)NH_2$, $NHC(O)NHNH_2$, $NHC(O)OH$, $NHNH_2$, $NHOH$, $NHS(O)_2H$, $OH$, $OS(O)_2OH$, $OCH_2X^6$, $OCH(X^6)_2$, $OC(X^6)_3$, $ONH_2$, $SH$, $S(O)_2NH_2$, $S(O)_2OH$, cycloalkyl, heterocycloalkyl, aryl, or heteroaryl;

each $R^{6B}$ is independently hydrogen, alkyl, heteroalkyl, $CH_2X^6$, $CH(X^6)_2$, $C(X^6)_3$, $C(O)NH_2$, $C(O)OH$, $NH_2$, $NHC(O)H$, $NHC(O)NH_2$, $NHC(O)NHNH_2$, $NHC(O)OH$, $NHNH_2$, $NHOH$, $NHS(O)_2H$, $OH$, $OS(O)_2OH$, $OCH_2X^6$, $OCH(X^6)_2$, $OC(X^6)_3$, $ONH_2$, $SH$, $S(O)_2NH_2$, $S(O)_2OH$, cycloalkyl, heterocycloalkyl, aryl, or heteroaryl; or any $R^{6A}$ and $R^{6B}$, together with the nitrogen atom to which they are bonded, independently forms a heterocycloalkyl or heteroaryl;

each $X^6$ is independently halogen;

each n is independently 0, 1, 2, 3, 4, 5, 6, 7, 8, or 9; and z is 0, 1, or 2.

2. The compound of claim 1, or a pharmaceutically acceptable salt, stereoisomer, or tautomer thereof, wherein $R^{11}$ is a 3- to 7-membered nitrogen-containing heterocycloalkyl, wherein the 3- to 7-membered nitrogen-containing heterocycloalkyl is optionally substituted with n independently selected $R^5$ substituents.

3. The compound of claim 2, or a pharmaceutically acceptable salt, stereoisomer, or tautomer thereof, wherein $R^{11}$ is aziridinyl, azetidinyl, pyrrolidinyl, piperidinyl, piperazinyl, morpholinyl, 1,2-oxazepanyl, 1,3-oxazepanyl, 1,4-oxazepanyl, or 1,2,3,6-tetrahydropyridinyl, wherein the aziridinyl, azetidinyl, pyrrolidinyl, piperidinyl, piperazinyl, morpholinyl, 1,2-oxazepanyl, 1,3-oxazepanyl, 1,4-oxazepanyl, or 1,2,3,6-tetrahydropyridinyl is optionally substituted with n independently selected $R^5$ substituents.

4. The compound of claim 2, wherein the compound is of formula (IIa) or formula (IIb):

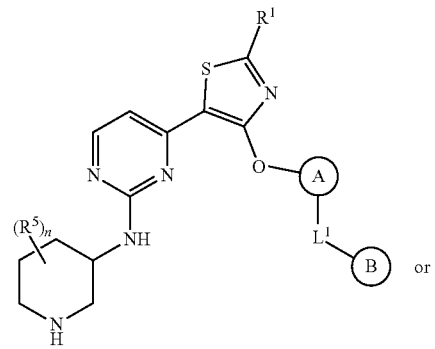

(IIa)

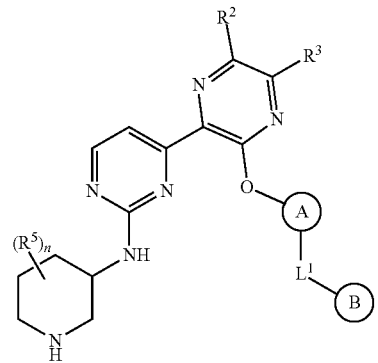

(IIb)

or a pharmaceutically acceptable salt, stereoisomer, or tautomer thereof.

5. The compound of claim 4, or a pharmaceutically acceptable salt, stereoisomer, or tautomer thereof, wherein n is 0, 1, or 2.

6. The compound of claim 4, or a pharmaceutically acceptable salt, stereoisomer, or tautomer thereof, wherein:
$R^5$ is halogen; and
n is 1.

7. The compound of claim 1, or a pharmaceutically acceptable salt, stereoisomer, or tautomer thereof, wherein $R^1$ is hydrogen or $C_1$-$C_3$ alkyl.

8. The compound of claim 1, or a pharmaceutically acceptable salt, stereoisomer, or tautomer thereof, wherein:
$R^2$ is hydrogen; and
$R^3$ is hydrogen.

9. The compound of claim 1, or a pharmaceutically acceptable salt, stereoisomer, or tautomer thereof, wherein:
ring A is a $C_6$-$C_{10}$ aryl, wherein the $C_6$-$C_{10}$ aryl is substituted with n independently selected $R^8$ substituents; and
each $R^8$ is independently halogen, $NO_2$, $C_1$-$C_6$ alkyl, 2- to 6-membered heteroalkyl, $CF_3$, $CCl_3$, $CBr_3$, $CI_3$, $C(O)NH_2$, $C(O)OH$, $NH_2$, $NHC(O)H$, $NHC(O)NHNH_2$, $NHC(O)OH$, $NHNH_2$, $N_3$, $NHOH$, $NHS(O)_2H$, $OH$, $OCH_2F$, $OCH_2Cl$, $OCH_2Br$, $OCH_2I$, $OCHF_2$, $OCHCl_2$, $OCHBr_2$, $OCHI_2$, $OCF_3$, $OCCl_3$, $OCBr_3$, $OCI_3$, $ONH_2$, $OS(O)_2OH$, $SH$, $S(O)_2NH_2$, $S(O)_2OH$, $C_3$-$C_6$ cycloalkyl, 3- to 6-membered heterocycloalkyl, $C_6$-$C_{10}$ aryl, or 5- or 6-membered heteroaryl, wherein each $C_3$-$C_6$ cycloalkyl, 3- to 6-membered heterocycloalkyl, $C_6$-$C_{10}$ aryl, and 5- or 6-membered heteroaryl is optionally and independently substituted with 1, 2, 3, 4, 5, 6, 7, 8, or 9 substituents independently selected from the group consisting of halogen, $NO_2$, $C_1$-$C_6$ alkyl, 2- to 6-membered heteroalkyl, $CF_3$, $CCl_3$, $CBr_3$, $CI_3$, $C(O)NH_2$, C(O)OH, NH$_2$, NHC(O)H, NHC(O)NHNH$_2$, NHC(O)OH, NHNH$_2$, NHOH, NHS(O)$_2$H, OH, OCH$_2$F, OCH$_2$Cl, OCH$_2$Br, OCH$_2$I, OCHF$_2$, OCHCl$_2$, OCHBr$_2$, OCHI$_2$, OCF$_3$, OCCl$_3$, OCBr$_3$, OCI$_3$, ONH$_2$, OS(O)$_2$OH, SH, S(O)$_2$NH$_2$, S(O)$_2$OH, C$_3$-C$_6$ cycloalkyl, 3- to 6-membered heterocycloalkyl, C$_6$-C$_{10}$ aryl, and 5- or 6-membered heteroaryl.

10. The compound of claim 9, or a pharmaceutically acceptable salt, stereoisomer, or tautomer thereof, wherein:

ring A is phenyl, wherein the phenyl is substituted with n independently selected R$^8$ substituents; and each R$^8$ is independently halogen or C$_1$-C$_6$ alkyl.

11. The compound of claim 1, or a pharmaceutically acceptable salt, stereoisomer, or tautomer thereof, wherein L$^1$ is alkylene.

12. The compound of claim 11, or a pharmaceutically acceptable salt, stereoisomer, or tautomer thereof, wherein L$^1$ is —CH$_2$—, —CH(CH$_3$)—, or —CH$_2$CH$_2$—.

13. The compound of claim 1, or a pharmaceutically acceptable salt, stereoisomer, or tautomer thereof, wherein L$^1$ is —C(O)—, —C(O)NR$^{12}$—, —C(O)O—, —NR$^{12}$—, —NR$^{12}$C(O)—, —NR$^{12}$C(O)O—, —NR$^{12}$S(O)$_2$—, —O—, —OC(O)—, —OC(O)NR$^{12}$—, —S—, —S(O)—, —S(O)$_2$—, or —S(O)$_2$NR$^{12}$.

14. The compound of claim 1, or a pharmaceutically acceptable salt, stereoisomer, or tautomer thereof, wherein L$^1$ is —CH$_2$NHS(O)$_2$—, —C(O)NH—, —C(O)NHCH$_2$—, —C(O)N(CH$_3$)CH$_2$—, —NHS(O)$_2$—, or —NHS(O)$_2$CH$_2$—.

15. The compound of claim 1, or a pharmaceutically acceptable salt, stereoisomer, or tautomer thereof, wherein:

ring B is a 3- to 6-membered heterocycloalkyl, C$_6$-C$_{10}$ aryl, or 5- or 6-membered heteroaryl, wherein the 3- to 6-membered heterocycloalkyl, C$_6$-C$_{10}$ aryl, or 5- or 6-membered heteroaryl is substituted with n independently selected R$^6$ substituents; and each R$^6$ is independently halogen, NO$_2$, C$_1$-C$_6$ alkyl, 2- to 6-membered heteroalkyl, CF$_3$, CCl$_3$, CBr$_3$, CI$_3$, C(O)NH$_2$, C(O)OH, NH$_2$, NHC(O)H, NHC(O)NHNH$_2$, NHC(O)OH, NHNH$_2$, N$_3$, NHOH, NHS(O)$_2$H, OH, OCH$_2$F, OCH$_2$Cl, OCH$_2$Br, OCH$_2$I, OCHF$_2$, OCHCl$_2$, OCHBr$_2$, OCHI$_2$, OCF$_3$, OCCl$_3$, OCBr$_3$, OCI$_3$, ONH$_2$, OS(O)$_2$OH, SH, S(O)$_2$NH$_2$, S(O)$_2$OH, C$_3$-C$_6$ cycloalkyl, 3- to 6-membered heterocycloalkyl, C$_6$-C$_{10}$ aryl, or 5- or 6-membered heteroaryl, wherein each C$_3$-C$_6$ cycloalkyl, 3- to 6-membered heterocycloalkyl, C$_6$-C$_{10}$ aryl, and 5- or 6-membered heteroaryl is optionally and independently substituted with 1, 2, 3, 4, 5, 6, 7, 8, or 9 substituents independently selected from the group consisting of halogen, NO$_2$, C$_1$-C$_6$ alkyl, 2- to 6-membered heteroalkyl, CF$_3$, CCl$_3$, CBr$_3$, CI$_3$, C(O)NH$_2$, C(O)OH, NH$_2$, NHC(O)H, NHC(O)NHNH$_2$, NHC(O)OH, NHNH$_2$, NHOH, NHS(O)$_2$H, OH, OCH$_2$F, OCH$_2$Cl, OCH$_2$Br, OCH$_2$I, OCHF$_2$, OCHCl$_2$, OCHBr$_2$, OCHI$_2$, OCF$_3$, OCCl$_3$, OCBr$_3$, OCI$_3$, ONH$_2$, OS(O)$_2$OH, SH, S(O)$_2$NH$_2$, S(O)$_2$OH, C$_3$-C$_6$ cycloalkyl, 3- to 6-membered heterocycloalkyl, C$_6$-C$_{10}$ aryl, and 5- or 6-membered heteroaryl.

16. The compound of claim 1, or a pharmaceutically acceptable salt, stereoisomer, or tautomer thereof, wherein z is 0.

17. The compound of claim 1, wherein the compound is selected from the group consisting of:

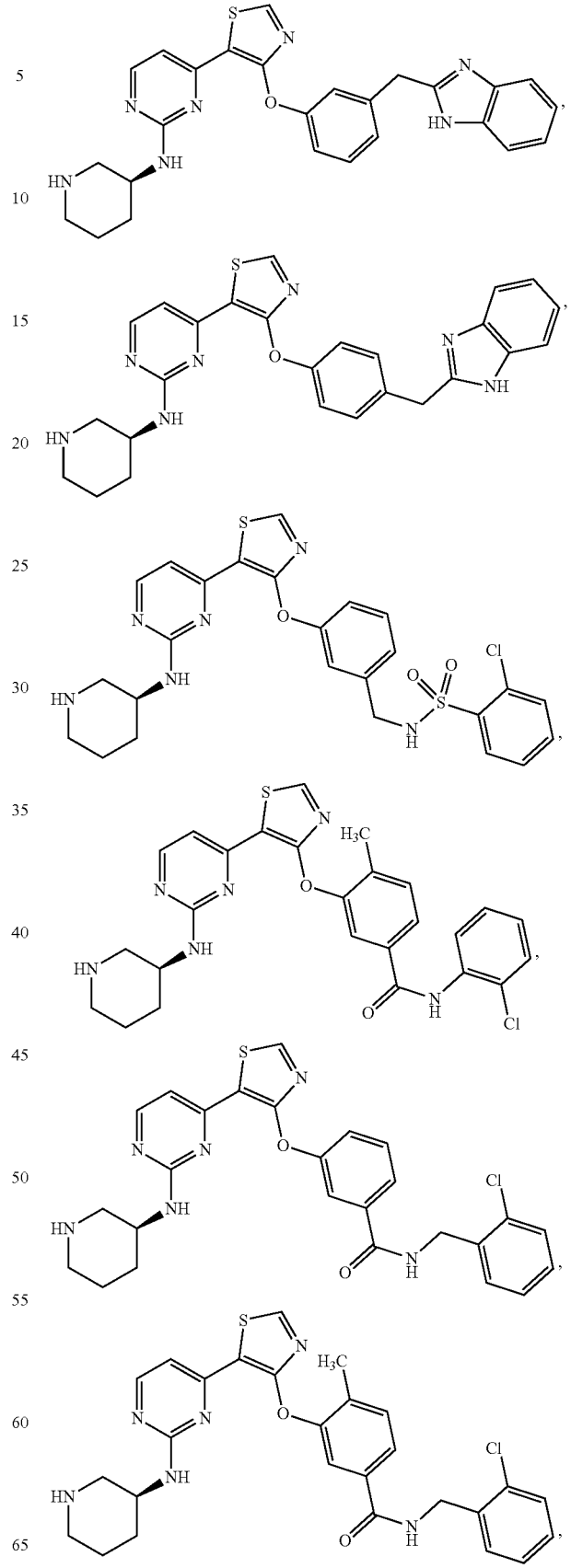

-continued
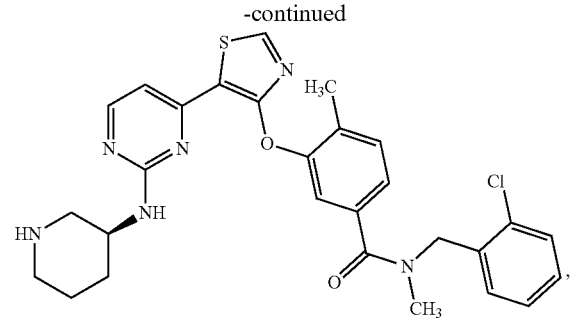
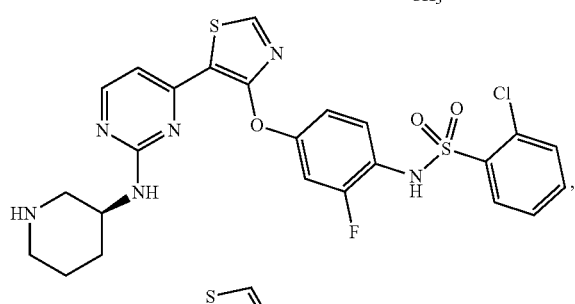
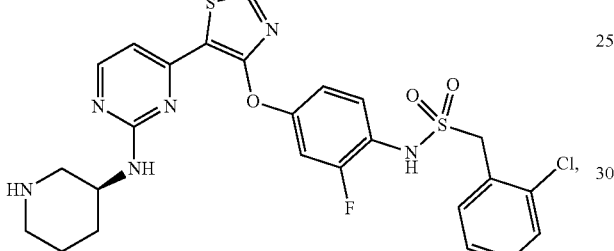
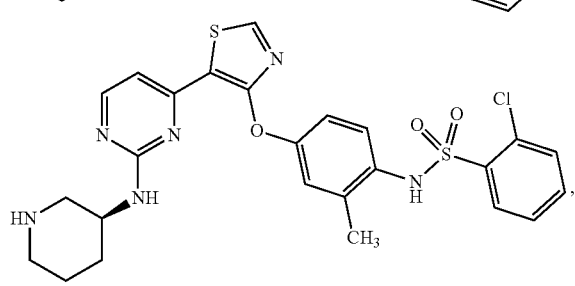
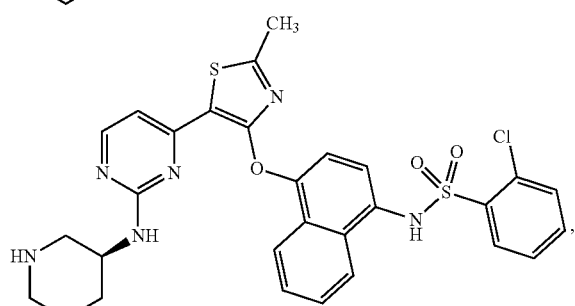
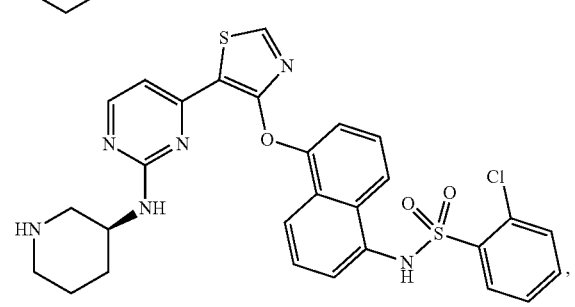
-continued
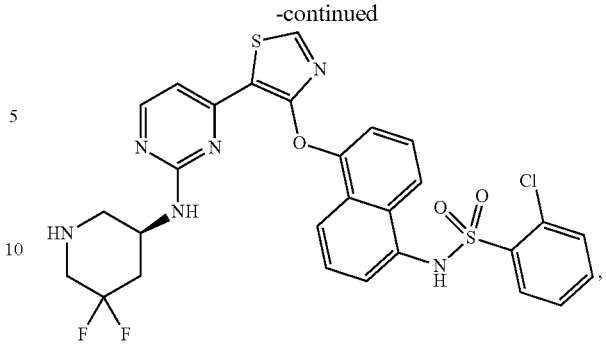
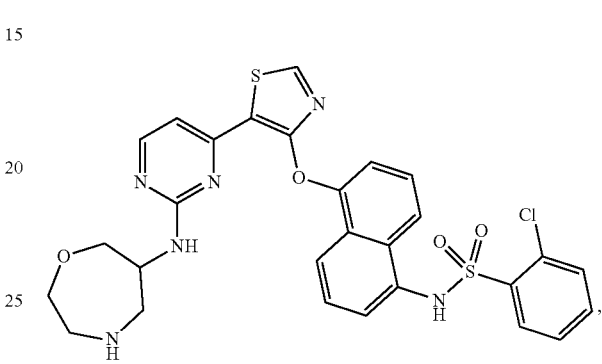
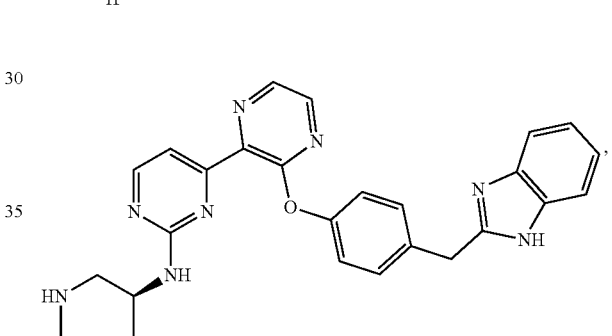
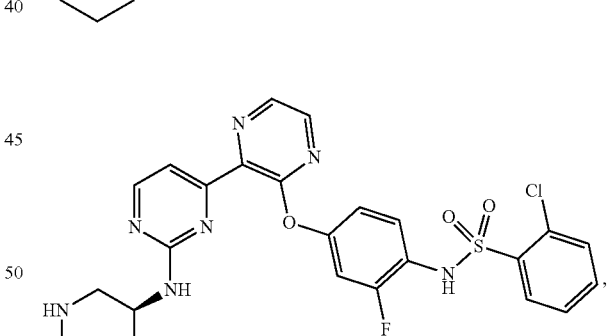
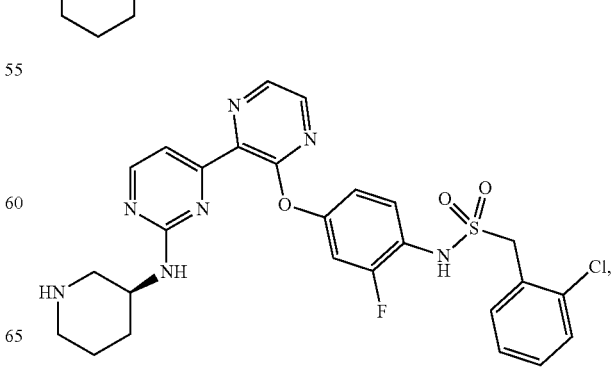

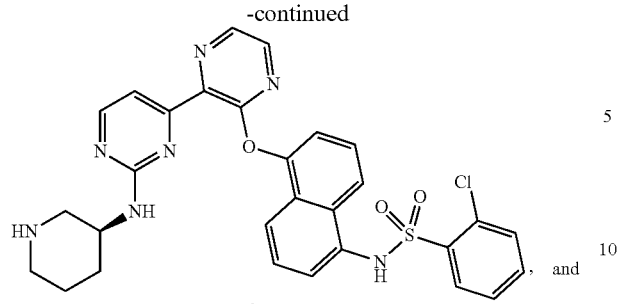
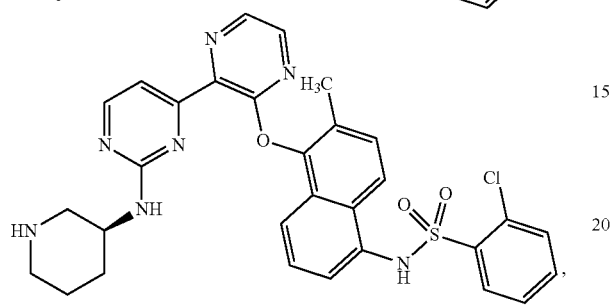
or a pharmaceutically acceptable salt or tautomer thereof.
18. A pharmaceutical composition comprising a pharmaceutically acceptable carrier and a compound of claim 1, or a pharmaceutically acceptable salt, stereoisomer, or tautomer thereof.
* * * * *